United States Patent
Fischer et al.

(10) Patent No.: US 11,142,558 B2
(45) Date of Patent: Oct. 12, 2021

(54) TUMOR NECROSIS FACTOR RECEPTOR (TNFR) BINDING PROTEIN COMPLEX WITH IMPROVED BINDING AND BIOACTIVITY

(71) Applicant: UNIVERSITÄT STUTTGART, Stuttgart (DE)

(72) Inventors: Roman Fischer, Nuremberg (DE); Roland Kontermann, Nuremberg (DE); Klaus Pfizenmaier, Tiefenbronn (DE); Martin Siegemund, Stuttgart (DE)

(73) Assignee: UNIVERSITÄT STUTTGART

( * ) Notice: Subject to any disclaimer, the term of this patent is extended or adjusted under 35 U.S.C. 154(b) by 0 days.

(21) Appl. No.: 16/500,849

(22) PCT Filed: Apr. 5, 2018

(86) PCT No.: PCT/EP2018/058786
§ 371 (c)(1),
(2) Date: Oct. 4, 2019

(87) PCT Pub. No.: WO2018/185247
PCT Pub. Date: Oct. 11, 2018

(65) Prior Publication Data
US 2020/0102362 A1    Apr. 2, 2020

(30) Foreign Application Priority Data
Apr. 6, 2017 (EP) .................... 17165279

(51) Int. Cl.
*C07K 14/525* (2006.01)
*A61K 38/00* (2006.01)

(52) U.S. Cl.
CPC ............ *C07K 14/525* (2013.01); *A61K 38/00* (2013.01); *C07K 2319/30* (2013.01)

(58) Field of Classification Search
CPC .............. C07K 14/525; C07K 2319/30; C07K 14/70578; A61K 38/00; G01N 33/6863
See application file for complete search history.

(56) References Cited

U.S. PATENT DOCUMENTS

| | | |
|---|---|---|
| 2004/0018170 A1 | 1/2004 | Shirwan |
| 2013/0224145 A1 | 8/2013 | Wang |

FOREIGN PATENT DOCUMENTS

| | | |
|---|---|---|
| DE | 10 2004 014983 A1 | 10/2005 |
| WO | 2001/042298 A1 | 6/2001 |
| WO | 2004/035794 A1 | 4/2004 |
| WO | 2009/007120 A2 | 1/2009 |
| WO | 2016/029043 A1 | 2/2016 |
| WO | 2016/112983 A1 | 7/2016 |
| WO | 2016/118641 A1 | 7/2016 |
| WO | 2016/146818 A1 | 9/2016 |
| WO | 2017/040312 A1 | 3/2017 |

OTHER PUBLICATIONS

The International Search Report (ISR) with Written Opinion for PCT/EP2018/058786 dated May 3, 2018, pp. 1-14.
Stone, Geoffrey W. et al. "Multimeric Soluble CD40 Ligand and GITR Ligand as Adjuvants for Human Immunodeficiency Virus DNA Vaccines" Journal of Virology (2006) vol. 80(4), pp. 1762-1772.
Wajant, H. et al. "Principles of antibody-mediated TNF receptor activation" Cell Death and Differentiation (2015) vol. 22(11), pp. 1727-1741.
Fu, Qingshan et al. "Structural Basis and Functional Role of Intramembrane Trimerization of the Fas/CD95 Death Receptor" Molecular Cell (2016) vol. 61, pates 602-613.

*Primary Examiner* — Robert S Landsman
(74) *Attorney, Agent, or Firm* — McDonnell Boehnen Hulbert & Berghoff LLP

(57) ABSTRACT

The present invention relates to a tumor necrosis factor receptor (TNFR) binding protein complex comprising 12 or more protein ligands (PLs) that specifically bind to the extracellular part of the same TNFR. Preferably, the TNFR binding protein complex binds to the extracellular part of TNFR2. Preferably, the TNFR binding protein complex of the present invention further comprises two or more polymerization domains (PD).

19 Claims, 21 Drawing Sheets

Figure 1:
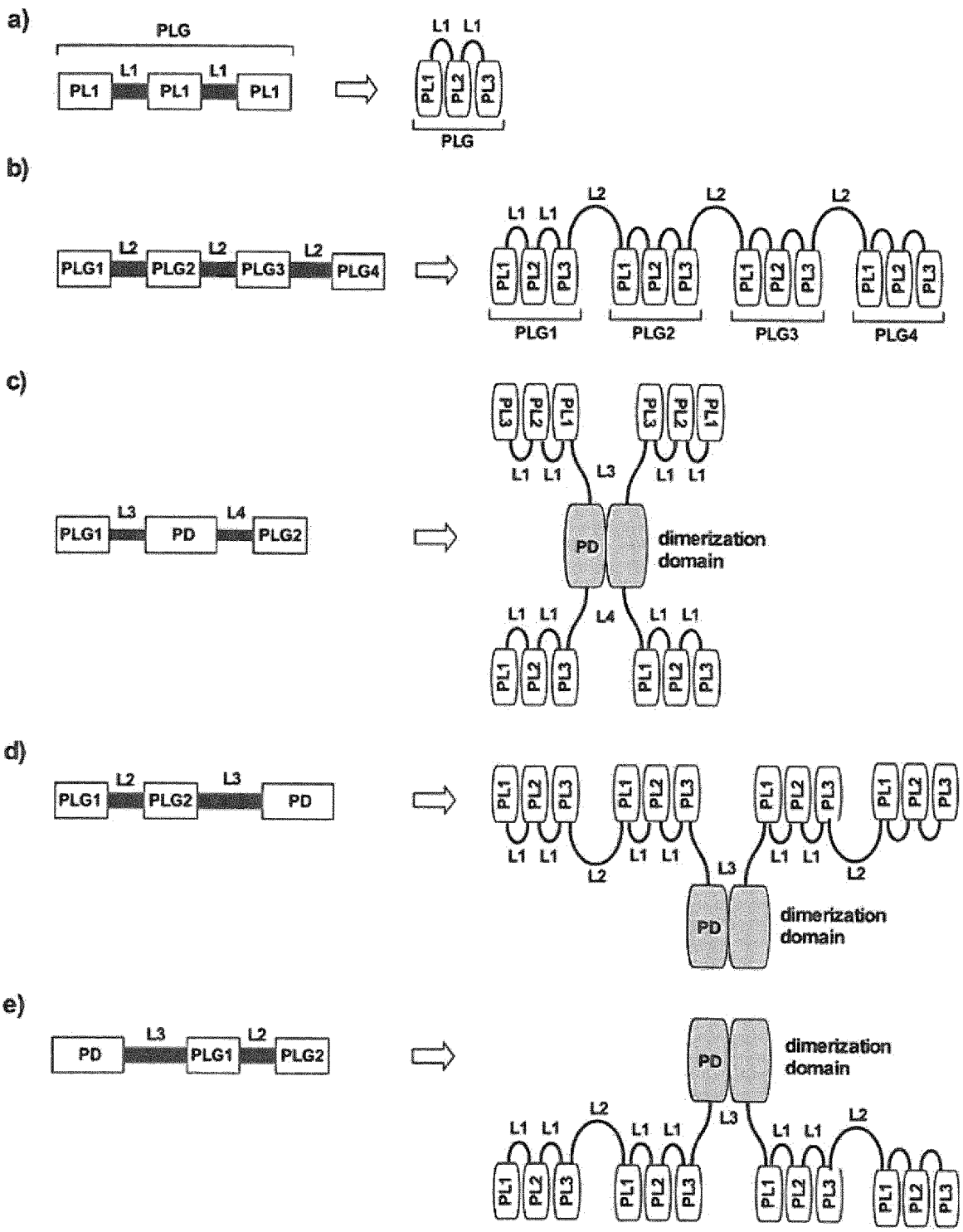
Figure 1:
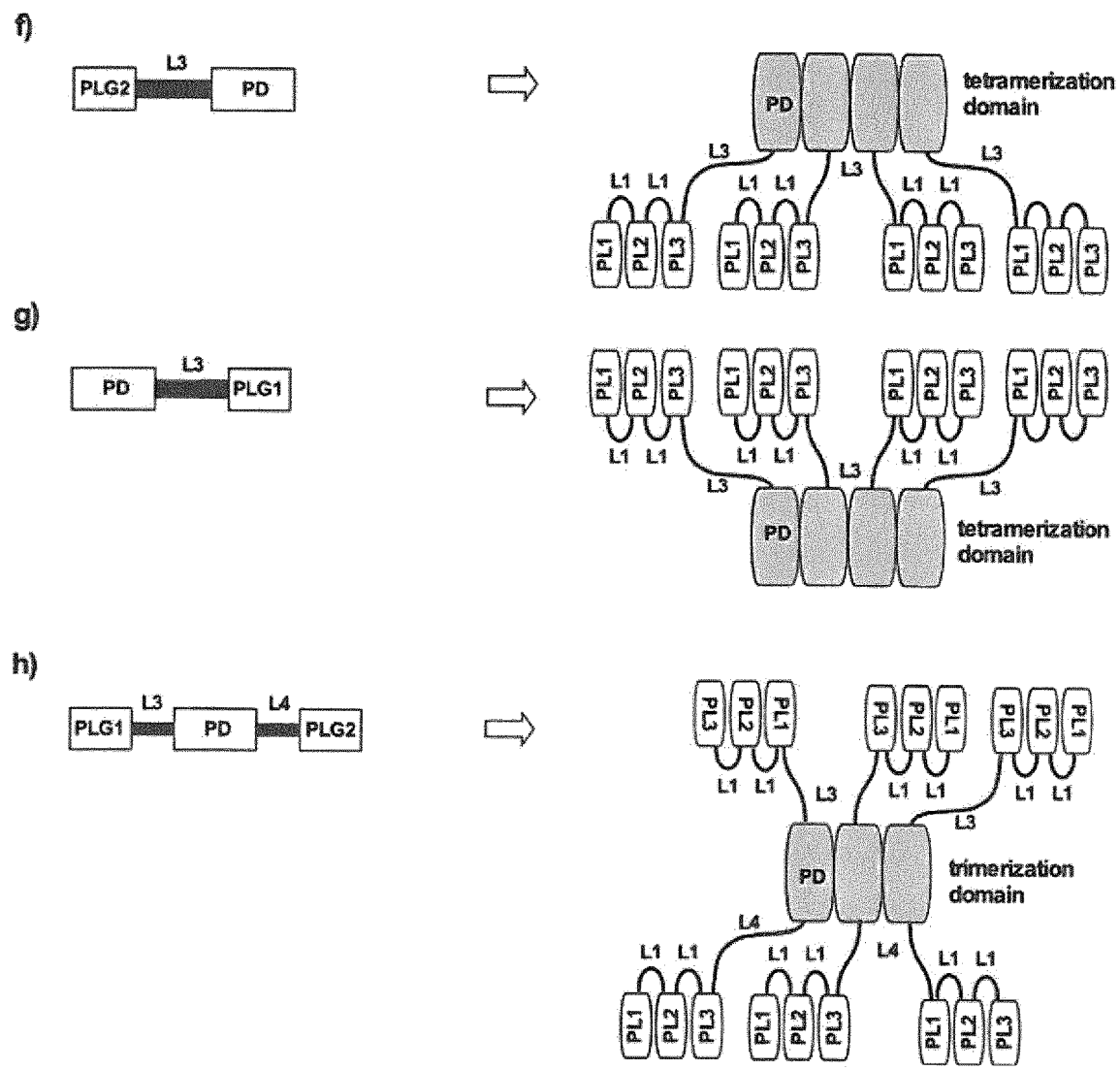

Specification includes a Sequence Listing.

B

A sc-mTNF$_{R2}$

EHD2-sc-mTNF$_{R2}$ p53-sc-mTNF$_{R2}$

GCN4-sc-mTNF$_{R2}$

A scTNF<sub>R2</sub>-Fc-scTNF<sub>R2</sub>

VASP-scTNF<sub>R2</sub>

TUMOR NECROSIS FACTOR RECEPTOR (TNFR) BINDING PROTEIN COMPLEX WITH IMPROVED BINDING AND BIOACTIVITY

CROSS-REFERENCE TO RELATED APPLICATION

This application is a U.S. national phase of International Application No. PCT/EP2018/058786, filed on Apr. 5, 2018, which claims priority to European Patent Application No. 17165279.5, filed Apr. 6, 2017, both of which are incorporated by reference herein in their entirety.

The present invention relates to a tumor necrosis factor receptor (TNFR) binding protein complex comprising 12 or more protein ligands (PLs) that specifically bind to the extracellular part of the same TNFR. Preferably, the TNFR binding protein complex binds to the extracellular part of TNFR2.

BACKGROUND OF THE INVENTION

The TNFR superfamily (TNFR-SF) is a protein superfamily of 27 known cytokine receptors. The TNFRs are typically expressed as trimeric type I transmembrane proteins. As a common feature, they contain up to six cysteine-rich domains (CDRs) in their extracellular domains.

A biological function is exerted by the binding of tumor necrosis factor (TNF) ligands and activation of the TNFRs. The TNF superfamily is comprised of 19 known ligands, which all share an extracellular TNF homology domain (THD). The THD triggers formation of non-covalent homotrimers. The homotrimeric structure represents the active form and is conserved among the members of the TNF ligand family. TNF ligands are typically expressed as type II transmembrane proteins, whereby in most ligands the extracellular domain can be subject to proteolytic cleavage into a soluble ligand.

TNF ligands and TNFRs are involved in diverse biological processes such as the selective induction of cell death in potentially dangerous and superfluous cells or the provision of costimulatory signals, thereby eliciting an effective immune response. These diverse and important regulatory roles in immunity make them of great interest in the development of TNFR-targeted immune-therapeutics.

It is therefore an object of the present invention to provide a protein complex capable of effectively modulating the activity of a TNFR.

SUMMARY OF THE INVENTION

In a first aspect, the present invention provides a dodecavalent tumor necrosis factor receptor (TNFR) binding protein complex comprising 12 or more protein ligands (PLs) that specifically bind to the extracellular part of the same TNFR, preferably to TNFR2.

In a second aspect, the present invention provides a nucleic acid molecule encoding the protein complex according to the first aspect of the present invention or a PLG (protein ligand group) or provides a PLG comprised in the protein complex according to the first aspect of the present invention.

In a third aspect, the present invention provides a vector comprising the nucleic acid molecule according to the second aspect of the present invention.

In a forth aspect, the present invention provides a complex according to the first aspect of the invention, a nucleic acid molecule according to the second aspect of the present invention and a vector according to the third aspect of the present invention for use as a medicament.

In a fifth aspect, the present invention provides a pharmaceutical composition comprising as an active agent a complex according to the first aspect of the present invention or a nucleic acid molecule according to the second aspect of the present invention or a vector according to the third aspect of the present invention.

In a sixth aspect, the present invention provides a complex according to the first aspect of the present invention or a nucleic acid molecule according to the second aspect of the present invention or a pharmaceutical composition according to the fifth aspect of the present invention for use in the diagnosis, prophylaxis or treatment of hyperproliferative disorders or inflammatory disorders or degenerative disorders.

FIGURES

FIG. 1: Schematic representation of TNFR-binding protein complexes of the present invention. (a) a protein ligand group (PLG) comprising three PLs (PL1 to PL3), which are connected via linker L1 to form a trivalent structure; (b) a dodecavalent complex including four trivalent PLGs of (a) (PLG1 to PLG4), which are connected via linker L2; (c) an oligomerized dodecavalent complex comprised of four trivalent PLGs of (a) (2×PLG1 and 2×PLG2) and two dimerization domains, wherein the PLG1s are fused to the N-terminus of each dimerization domain via linker L3 and the PLG2s are fused to the C-terminus of each dimerization domain via linker L4; (d) an oligomerized dodecavalent complex comprised of four PLGs of (a) (2×PLG1 and 2'PLG2) and two dimerization domains, wherein the PLG1s and PLG2s are connected via linker L2 and each PLG2 is fused to the N-terminus of each dimerization domain via linker L3; (e) an oligomerized dodecavalent complex comprised of four PLGs of (a) (2×PLG1 and 2×PLG2) and two dimerization domains, wherein the PLG1s and PLG2s are connected via linker L2 and each PLG2 is fused to the C-terminus of each dimerization domain via linker L3; (f) an oligomerized dodedecavalent complex comprised of four trivalent PLGs (4×PLG1) and four tetramerization domains, wherein each PLG1 is fused to the C-terminus of each dimerization domain via linker L3; (g) oligomerized dodecavalent complex comprised of four trivalent PLGs (4×PLG1) and four tetramerization domains, wherein each PLG1 is fused to the N-terminus of each dimerization domain via linker L3; (h) an oligomerized octadecavalent complex comprised of six trivalent PLGs of (a) (3×PLG1 and 3×PLG2) and three trimerization domains, wherein the PLG1s are fused to the N-terminus of each trimerization domain via linker L3 and the PLG2s are fused to the C-terminus of each trimerization domain via linker L4.

Figure 2:
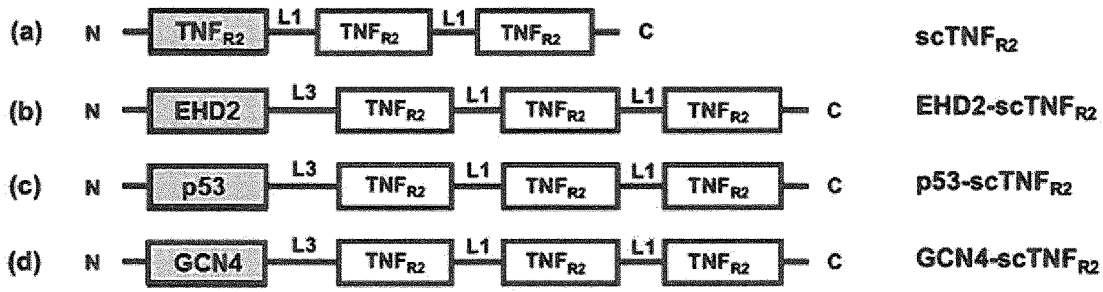
Figure 2:
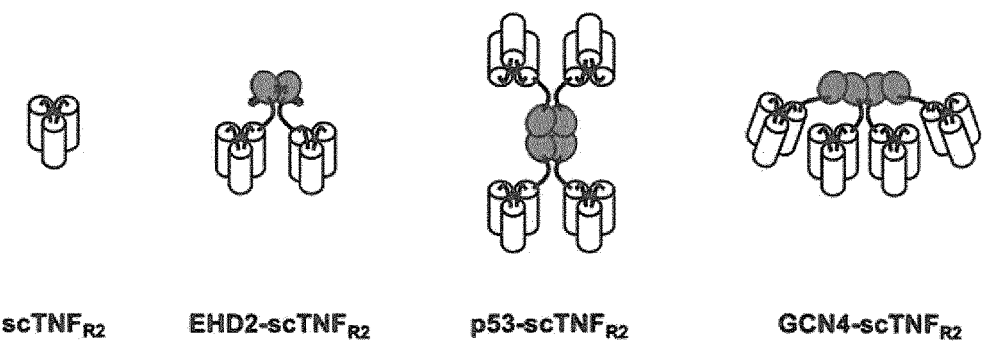
Figure 2:
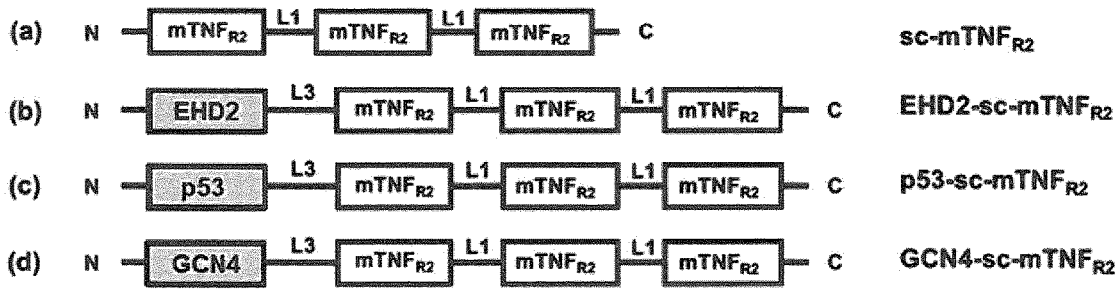
Figure 2:
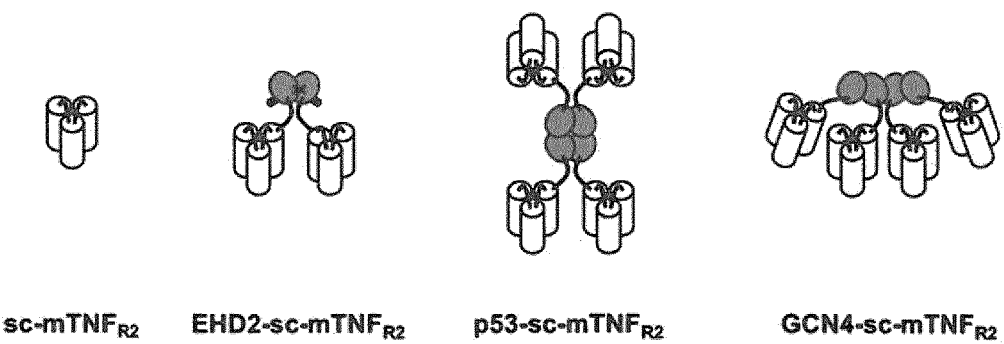

FIG. 2: Schematic representation of TNFR-binding protein complexes comprising human TNF (A) and mouse TNF (B) as PL. (a) a trivalent protein ligand group (PLG) comprising three PLs connected by linker L1; the PL is a TNFR2-binding mutant (D143N/A145R for human TNF (A), (D221N/A223R) for mouse TNF (B) of single-chain TNF (scTNF$_{R2}$ (human) and sc-mTNF$_{R2}$ (mouse)); (b) an oligomerized hexavalent complex comprised of two trivalent PLGs of (a) and two dimerization domains EHD2 from IgE CH$_2$, wherein each trivalent PLG is fused to the C-terminus of a dimerization domain (EHD2-sc-TNF$_{R2}$ (human) and EHD2-sc-mTNF$_{R2}$ (mouse)); (c) an oligomerized dodecavalent complex comprised of four trivalent PLGs of (a)

and four tetramerization domains from p53, wherein each trivalent PLG is fused to the C-terminus of the tetramerization domain (p53-sc-TNF$_{R2}$ (human) and p53-sc-mTNFR2 (mouse)); (d) an oligomerized dodecavalent complex comprised of four trivalent PLGs of (a) and four tetramerization domains from GCN4, wherein each trivalent PLG is fused to the C-terminus of a tetramerization domain (GCN4-sc-TNF$_{R2}$ (human), GCN4-sc-mTNF$_{R2}$ (mouse)).

Figure 3:
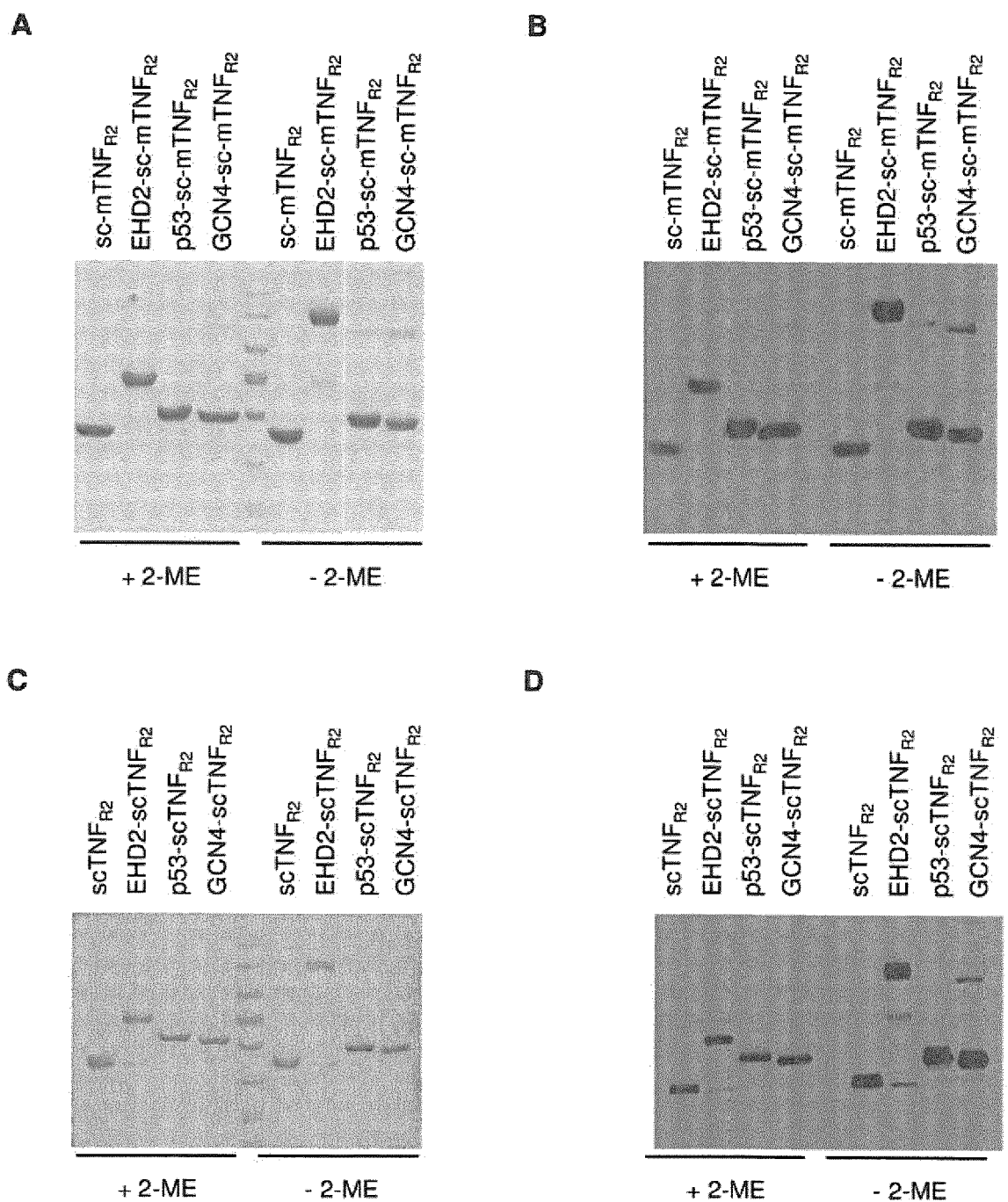

FIG. 3: SDS PAGE analysis of TNFR-binding protein complexes. TNFR-binding protein complexes were produced in HEK293-6E cells and purified by affinity chromatography followed by size exclusion chromatography. Analysis of mouse protein derived (A, B) and human protein derived (C, D) complexes by Coomassie staining (A, C) and immunoblot staining (B, D) under reducing (in the presence of 2-mercapto ethanol, +2-ME) and non-reducing conditions (in the absence of 2-mercapto ethanol, −2-ME).

Figure 4:
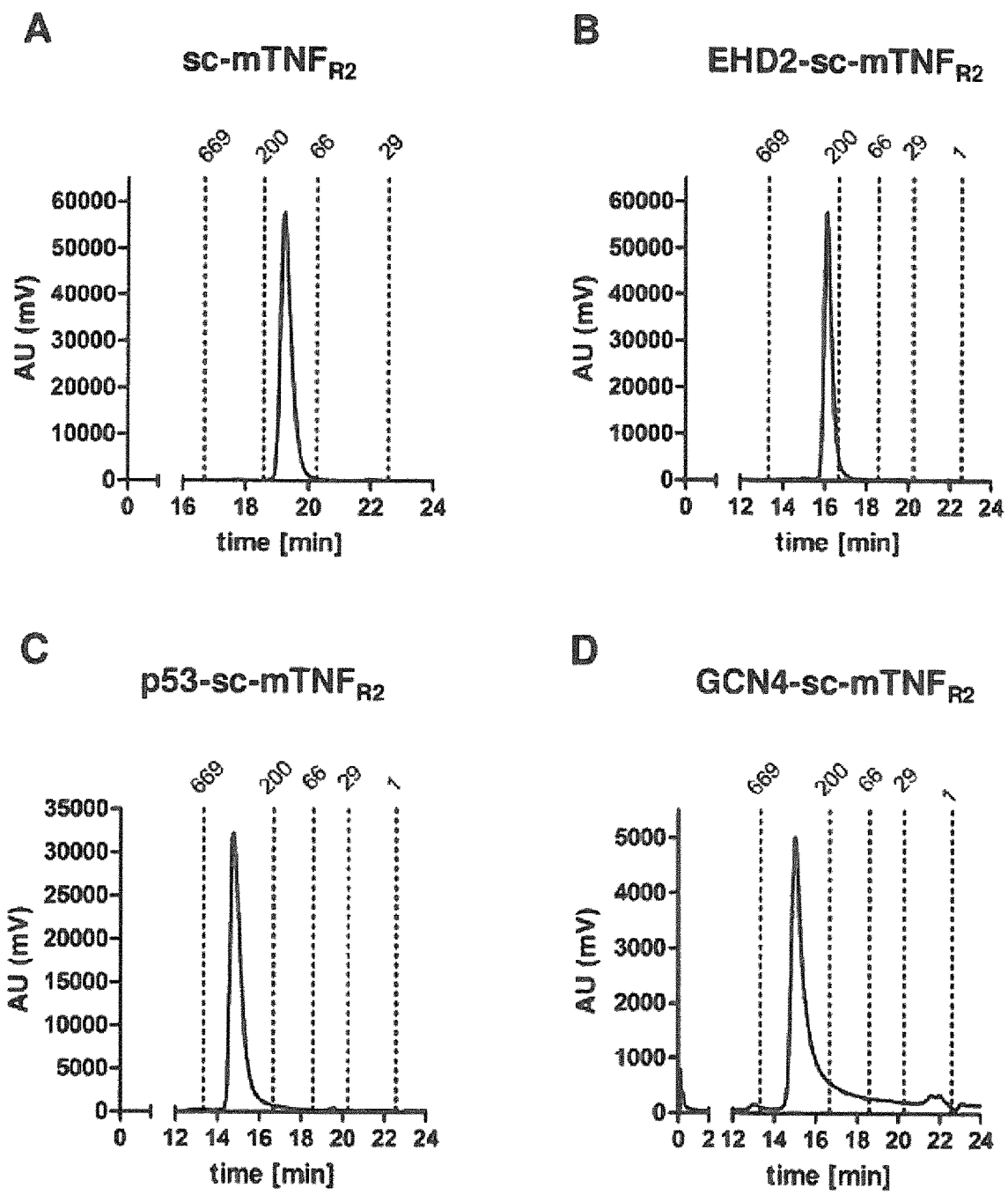
Figure 4:
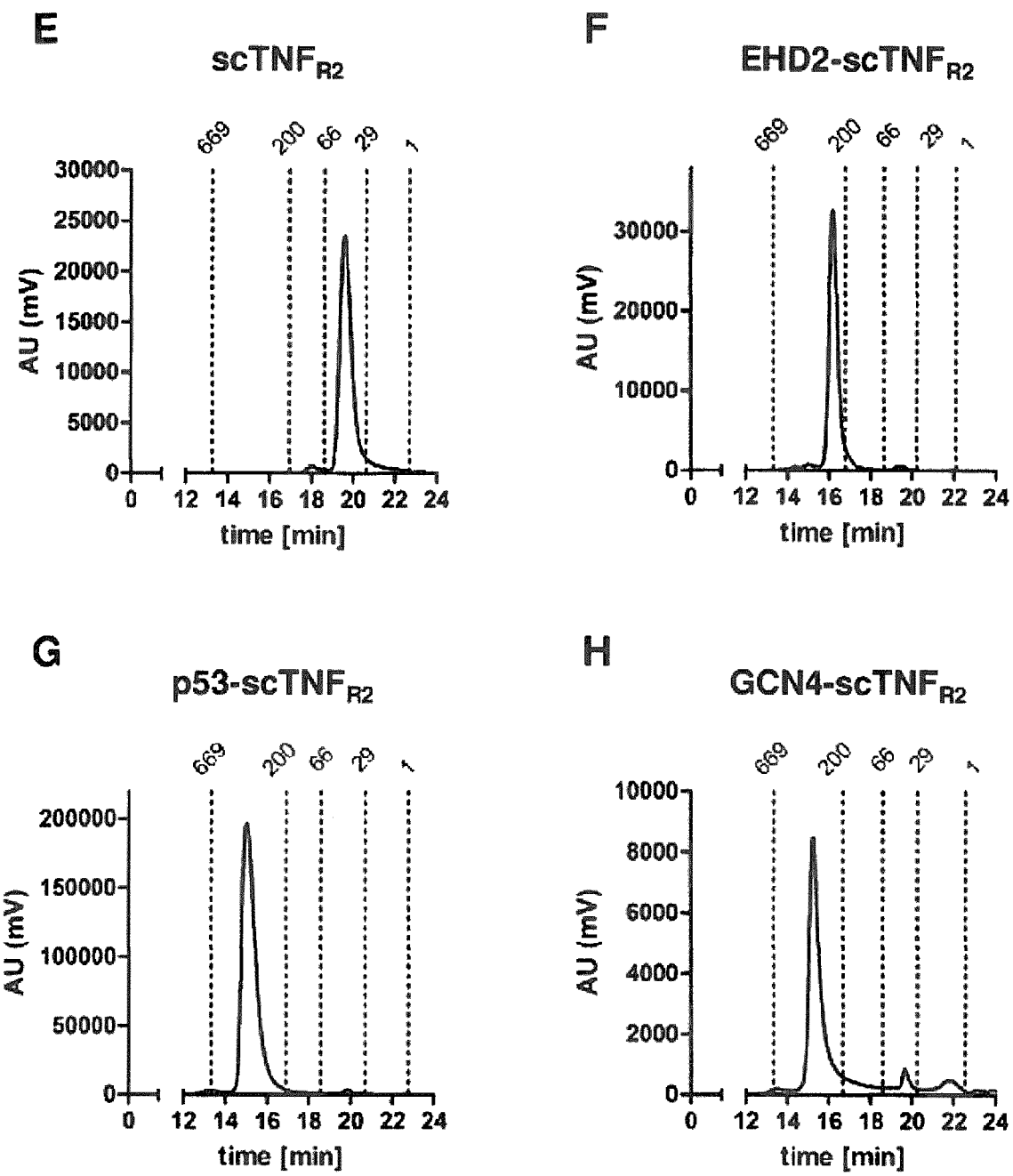

FIG. 4: Native structure of TNFR-binding protein complexes. Complexes where analyzed by size exclusion chromatography using a BioSep-Sec-2000 column. Positions of used standard proteins are indicated.

Figure 5:
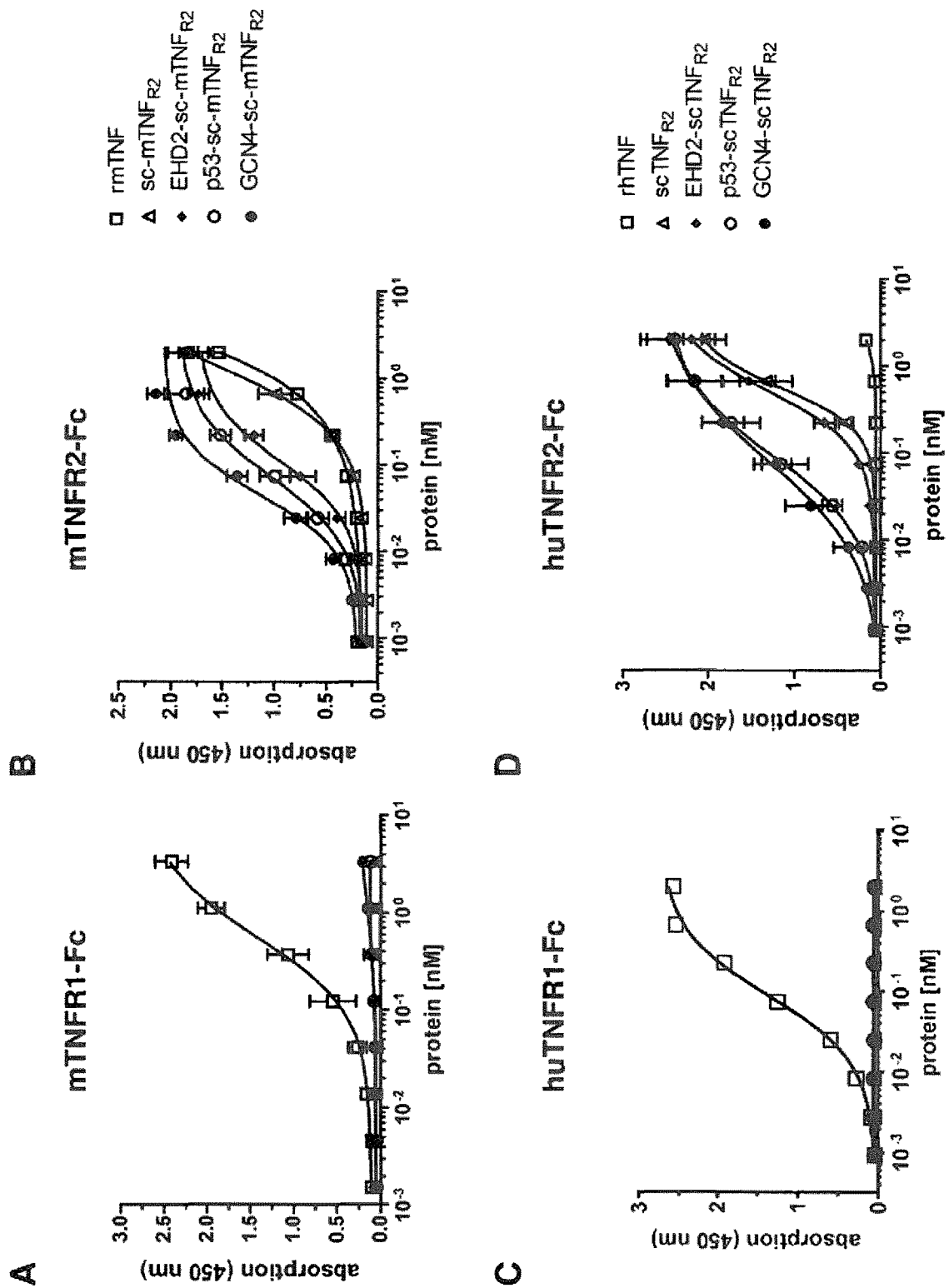

FIG. 5: Specific binding of TNFR-binding protein complexes. Binding of recombinant mouse TNF (rmTNF) and mouse TNF derived TNFR-binding protein complexes (A, B) and recombinant human TNF (rhTNF) and human TNF derived TNFR-binding protein complexes (C, D) to mouse TNFR1-Fc (A), human TNFR1-Fc (C), mouse TNFR2-Fc (B), and huTNFR2-Fc (D) as determined by ELISA (n=3; ±SEM).

Figure 6:
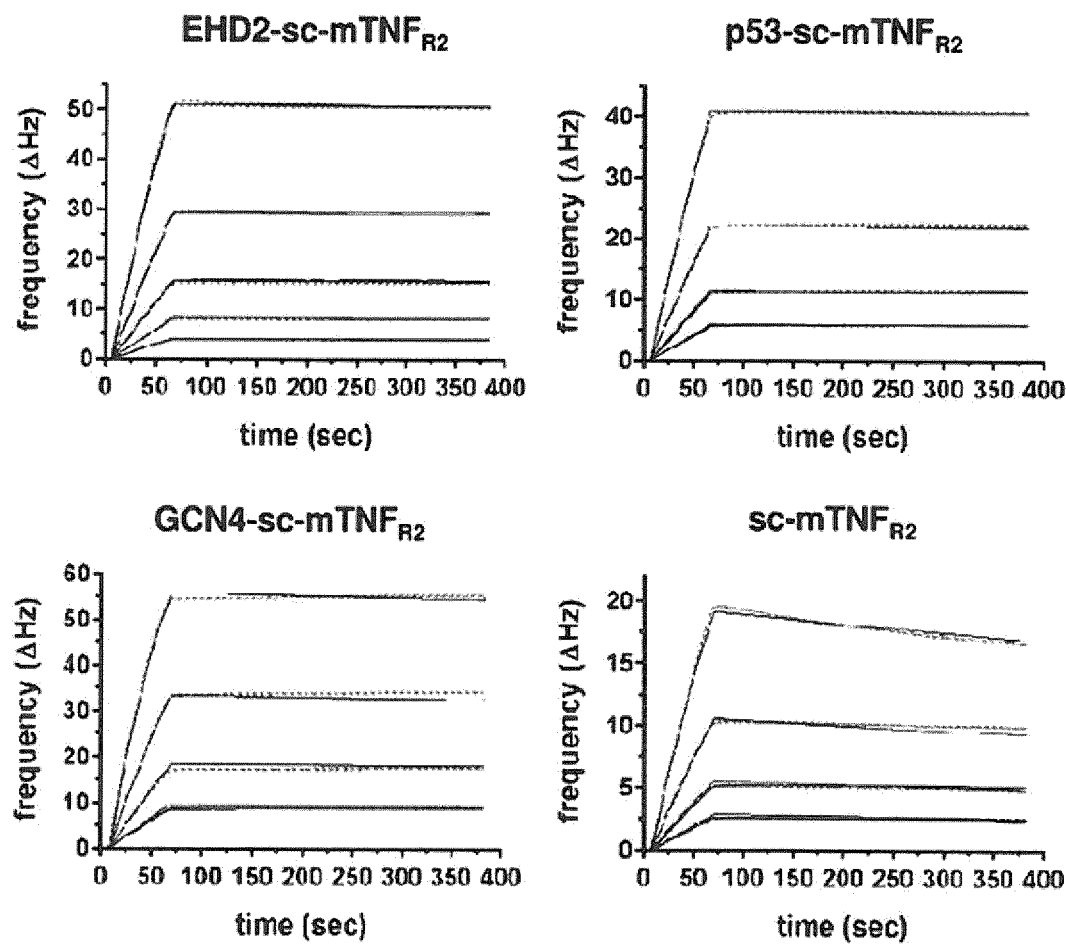
Figure 6:
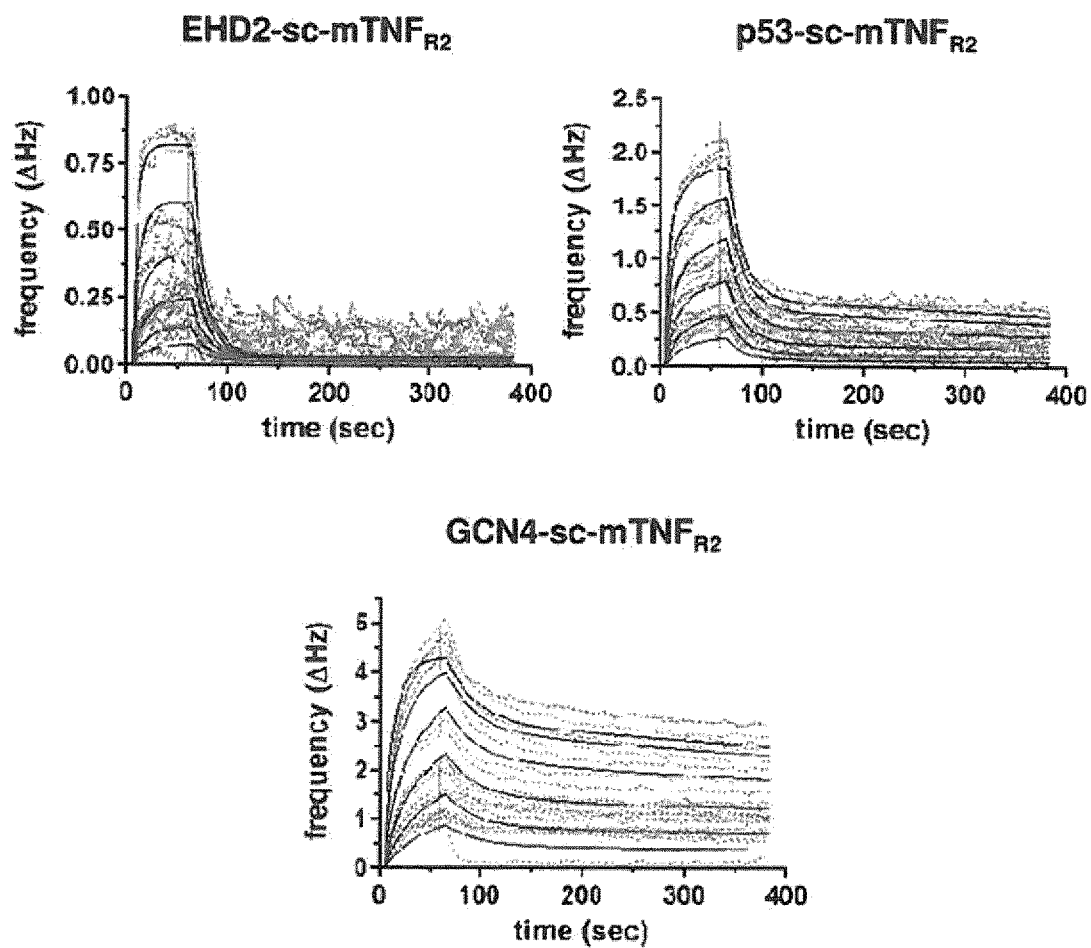

FIG. 6: Comparative affinity analyses of TNFR-binding protein complexes. Binding of the mouse TNF derived TNFR-binding protein complexes to human TNFR2 was analyzed by QCM at high density (A; 270 Hz) and low density (B; 130 Hz) of immobilized human TNFR2-Fc. The proteins were analyzed at concentrations between 1-32 nM (A) or 8-256 nM (B) at 37° C. in triplicates for each concentration (dashed lines=measured data, solid lines=fitted curves).

Figure 7:
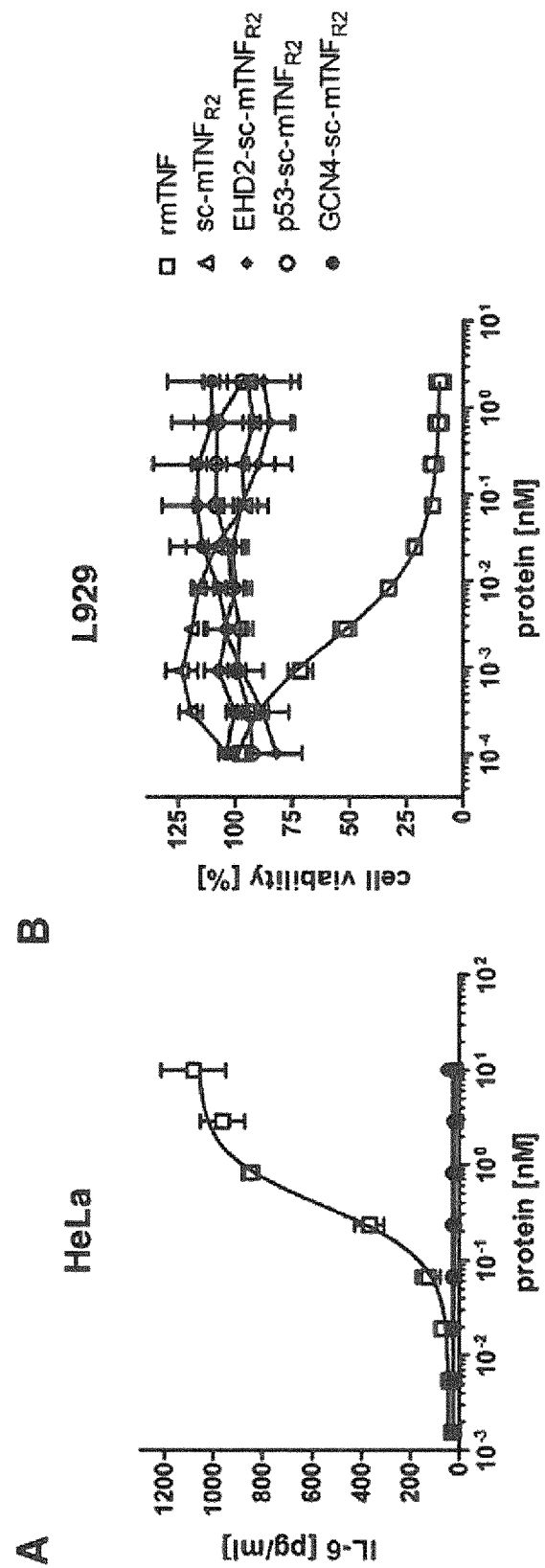

FIG. 7: Lack of activation of TNFR1 by TNFR-binding protein complexes. (A) HeLa cells were incubated with different concentrations or rmTNF as well as mouse TNF derived TNFR-binding protein complexes. The supernatant was analyzed for the presence of IL-6 using ELISA (n=3; ±SEM). (B) L929 cells where incubated with different concentrations of rmTNF as well as mouse TNF derived TNFR-binding protein complexes in the presence of actinomycin D. The cell viability was determined via a crystal violet assay (n=3; ±SEM).

Figure 8:
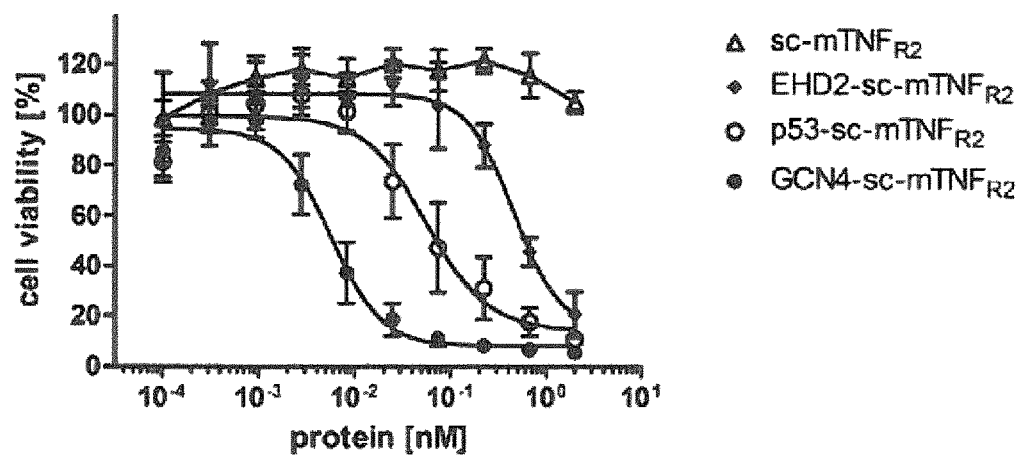
Figure 8:
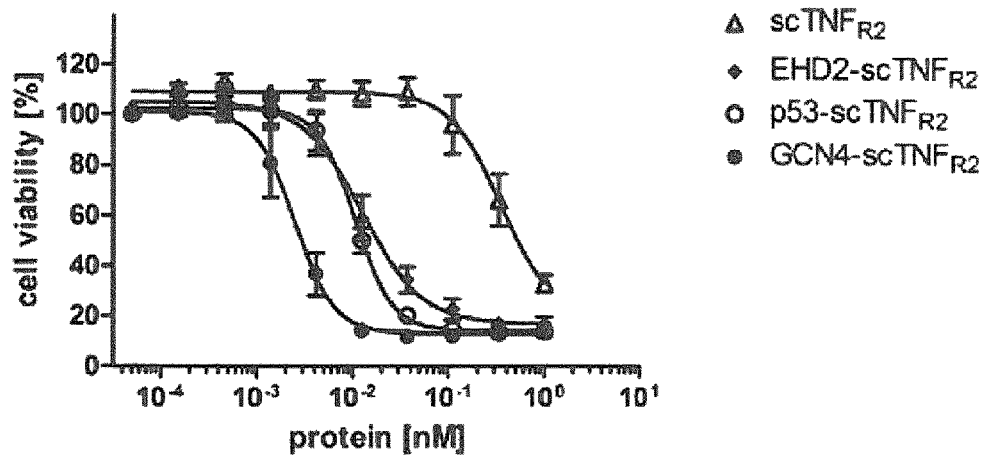

FIG. 8: TNFR2-induced cell death. Kym-1 cells where stimulated with (A) mouse TNF derived TNFR-binding protein complexes and (B) human TNF derived TNFR-binding protein complexes. The cell viability was determined via a crystal violet assay (n=3; ±SEM).

Figure 9:
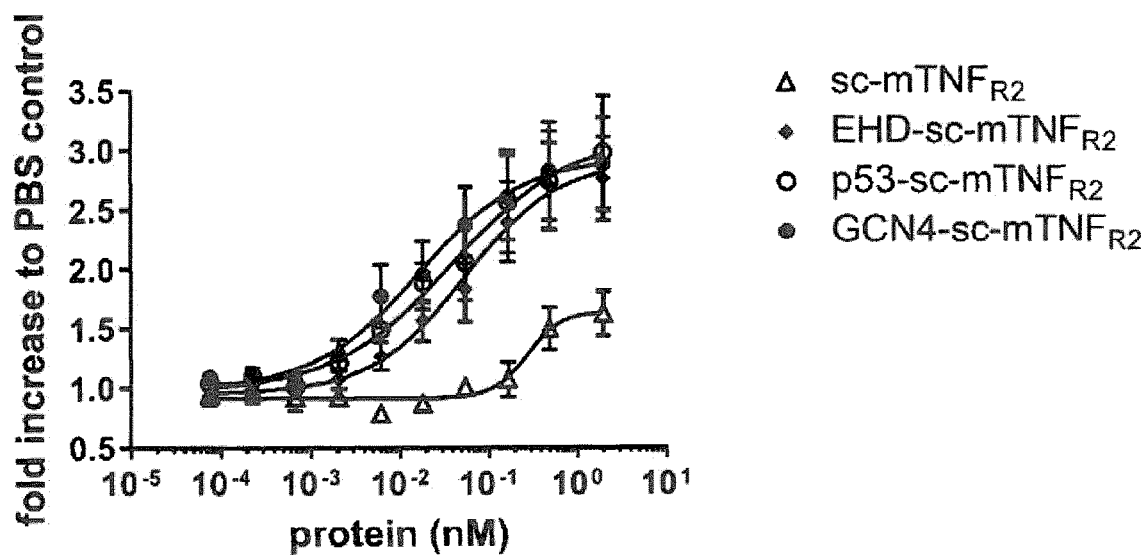

FIG. 9: TNFR2-induced cell proliferation. Primary thymocytes isolated from C57BL/6 mice were incubated on anti-CD3 coated plates with mouse TNF derived TNFR-binding protein complexes at different concentrations. The cell number was determined via an MTT assay (n=5; ±SEM).

Figure 10:
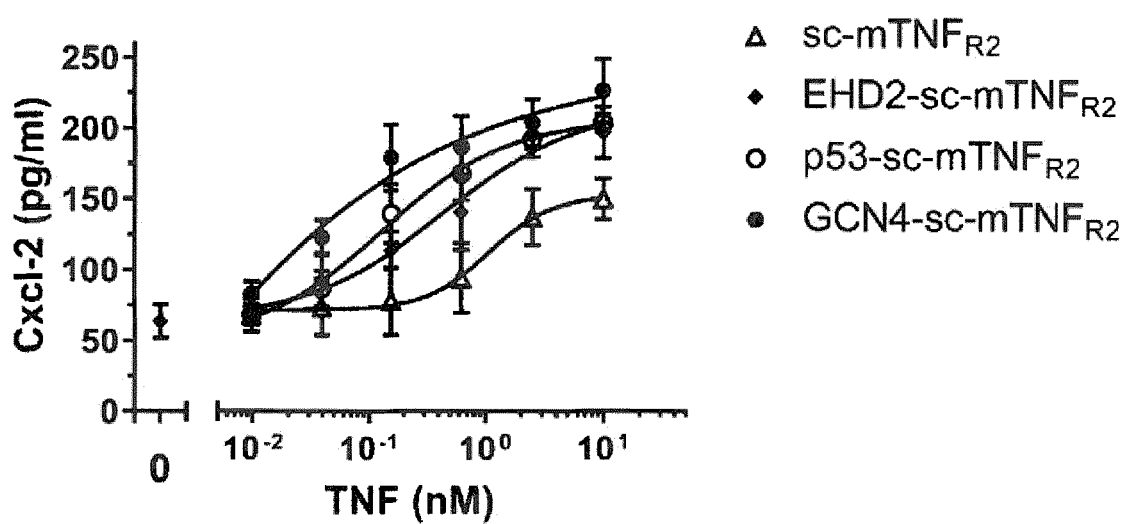

FIG. 10: TNFR2-induced Cxcl-2 secretion. BV-2 cells were incubated for 24 hours with mouse TNF derived TNFR-binding protein complexes. Then supernatant was harvested and analyzed for presence of secreted Cxcl-2 by ELISA (n=3±SEM).

Figure 11:
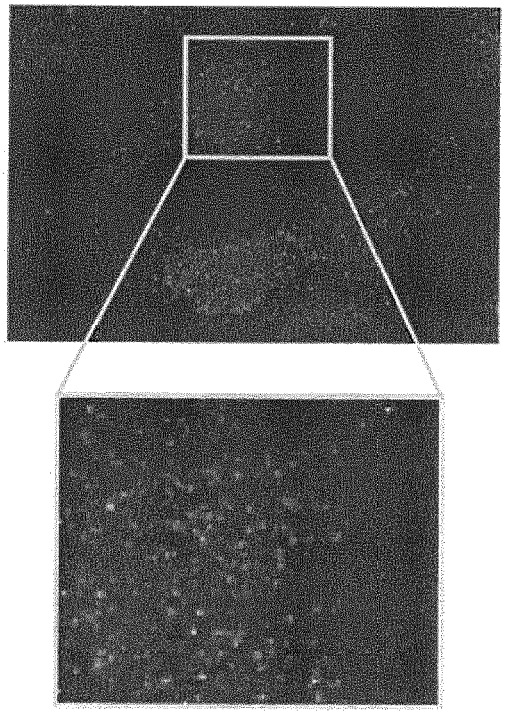
Figure 11:
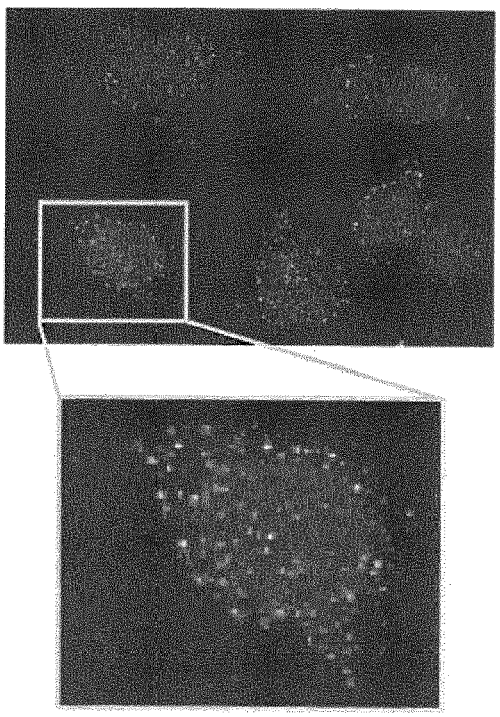
Figure 11:
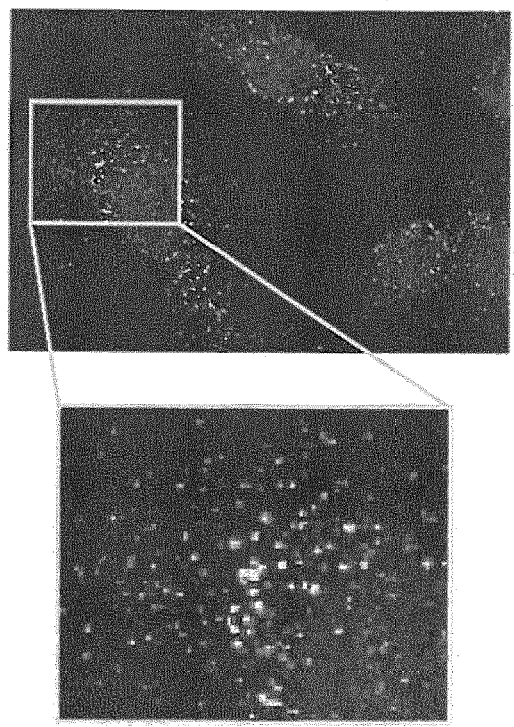
Figure 11:
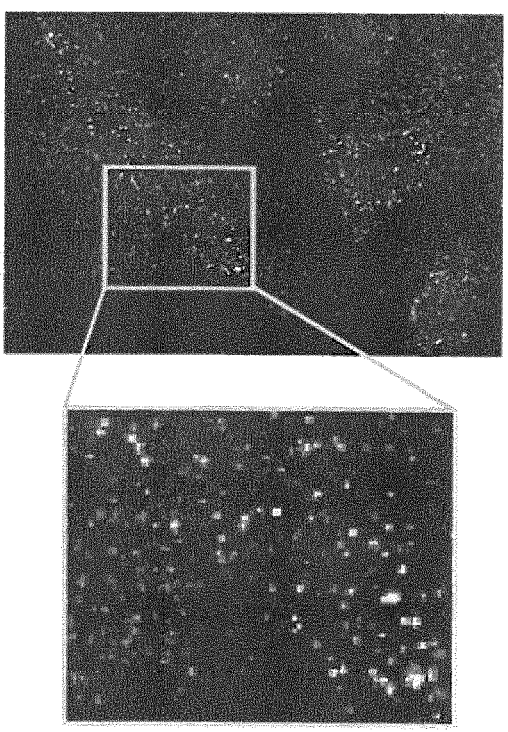
Figure 11:
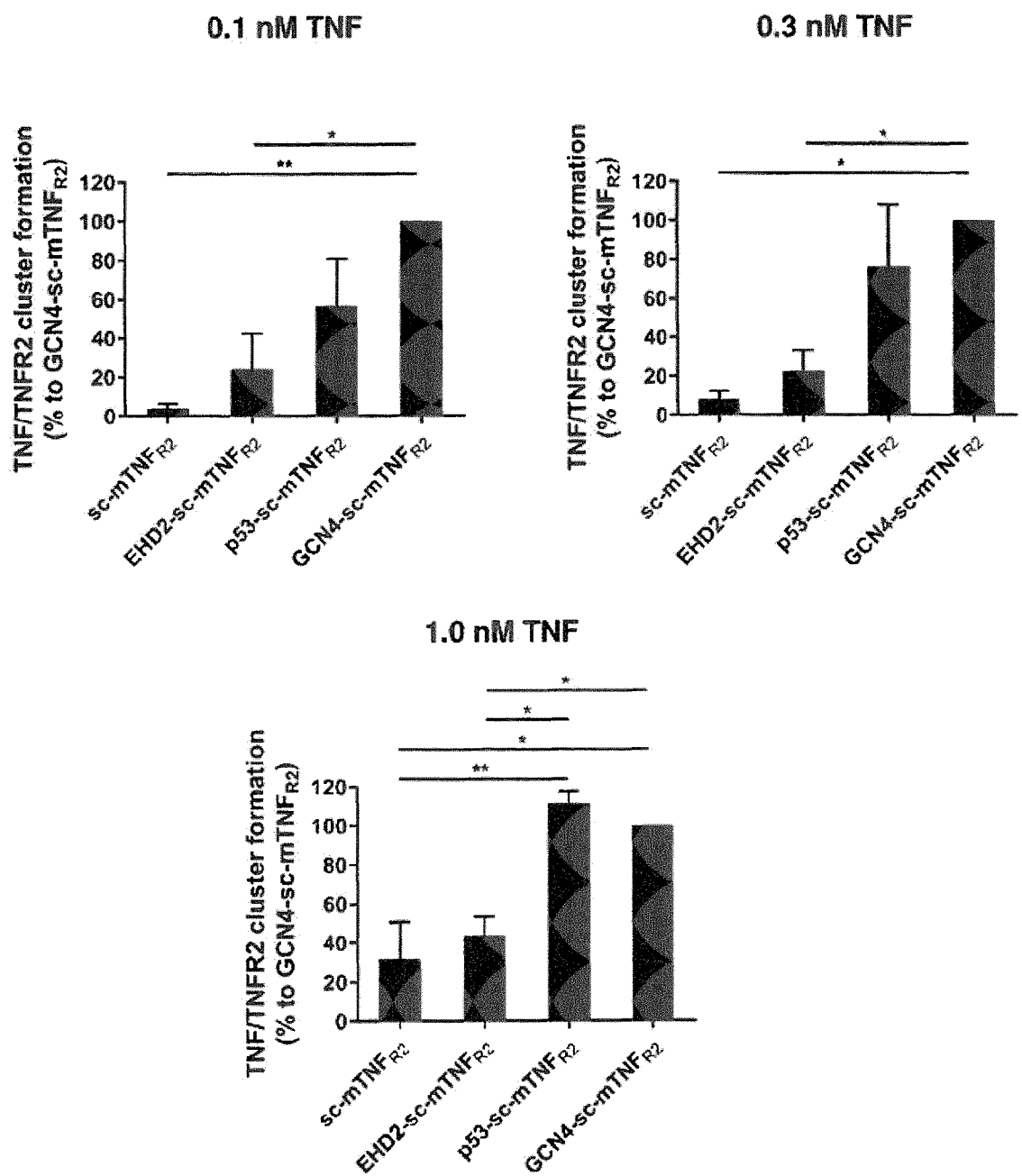

FIG. 11: TNFR2-induced TNF/TNFR2 cluster formation (A) BV-2 cells were incubated with mouse-derived TNFR-binding protein complexes at different concentrations (0.1, 0.3, 1.0 nM) for 15 minutes. Then cells were fixed and localization of TNFR2 (Alexa Fluor 546) and oligomerized TNF muteins (Alexa Fluor 488) was visualized by immunofluorescence microscopy. TNF/TNFR2 clusters are visualized as large dots within the cells. DAPI was used to counterstain cell nuclei. Fluorescence was analyzed using a Zeiss Axio Observer Spinning Disc microscope. Representative pictures for stimulation with 1 nM of the oligomerized TNF muteins are shown. (B) Quantification of TNF/TNFR2 clustering (n=3±SEM).

Figure 12:
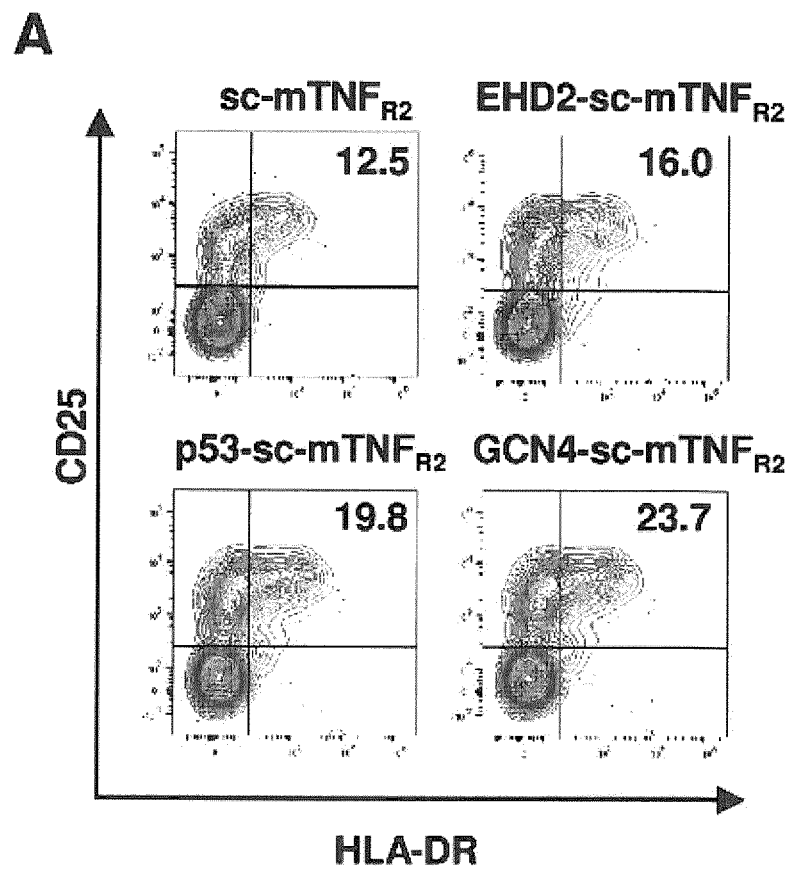
Figure 12:
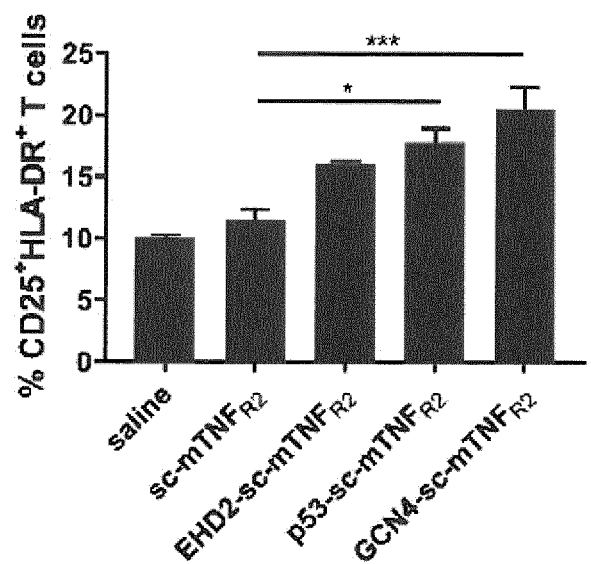
Figure 12:
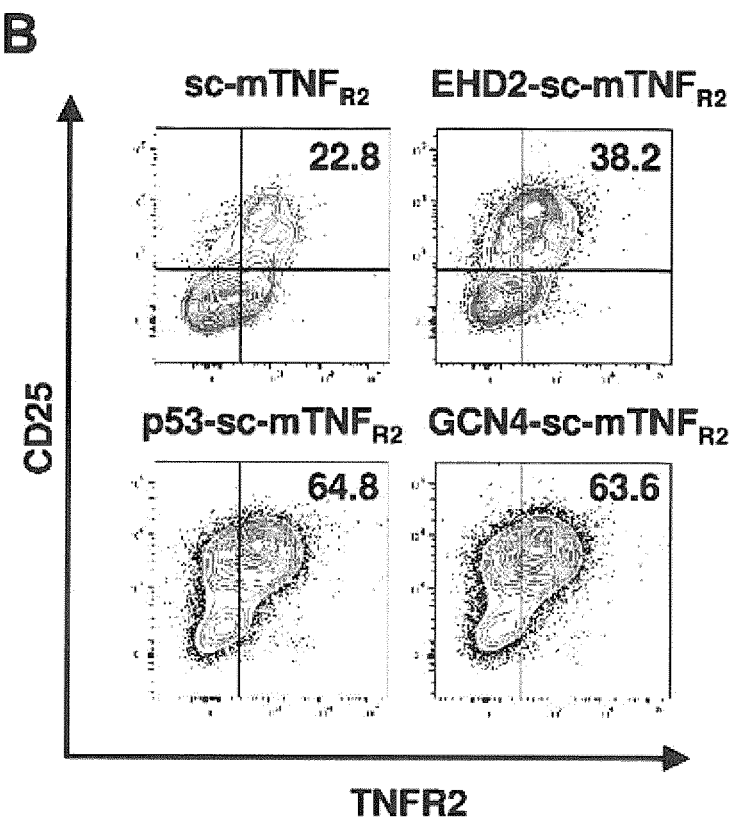
Figure 12:
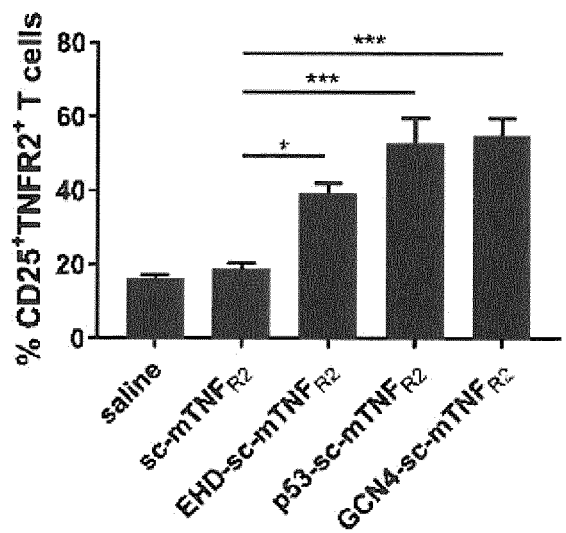

FIG. 12: TNFR2-induced T cell activation. (A) CD3$^+$ T cells isolated from human PBMCs were activated using plate-bound anti-CD3 antibodies and incubated in the presence of IL-2 and mouse TNF derived TNFR-binding protein complexes. The expression of CD25 and HLA-DR was determined via flow cytometry. Shown is a representative donor. Combined data are from three independent experiments (n=3±SEM). (B) CD3$^+$ T cells were isolated from mouse splenocytes via magnetic separation. T cells were activated using plate-bound anti-CD3 (5 μg/ml) and cultivated in presence of interleukin 2 (IL-2) and 0.3 nM of mouse TNF derived TNFR-binding protein complexes for 4 days. Number of activated CD25$^+$TNFR2$^+$ T cells was determined by flow cytometry. Shown is a representative donor. Combined data are from three independent experiments (n=3±SEM)

Figure 13:
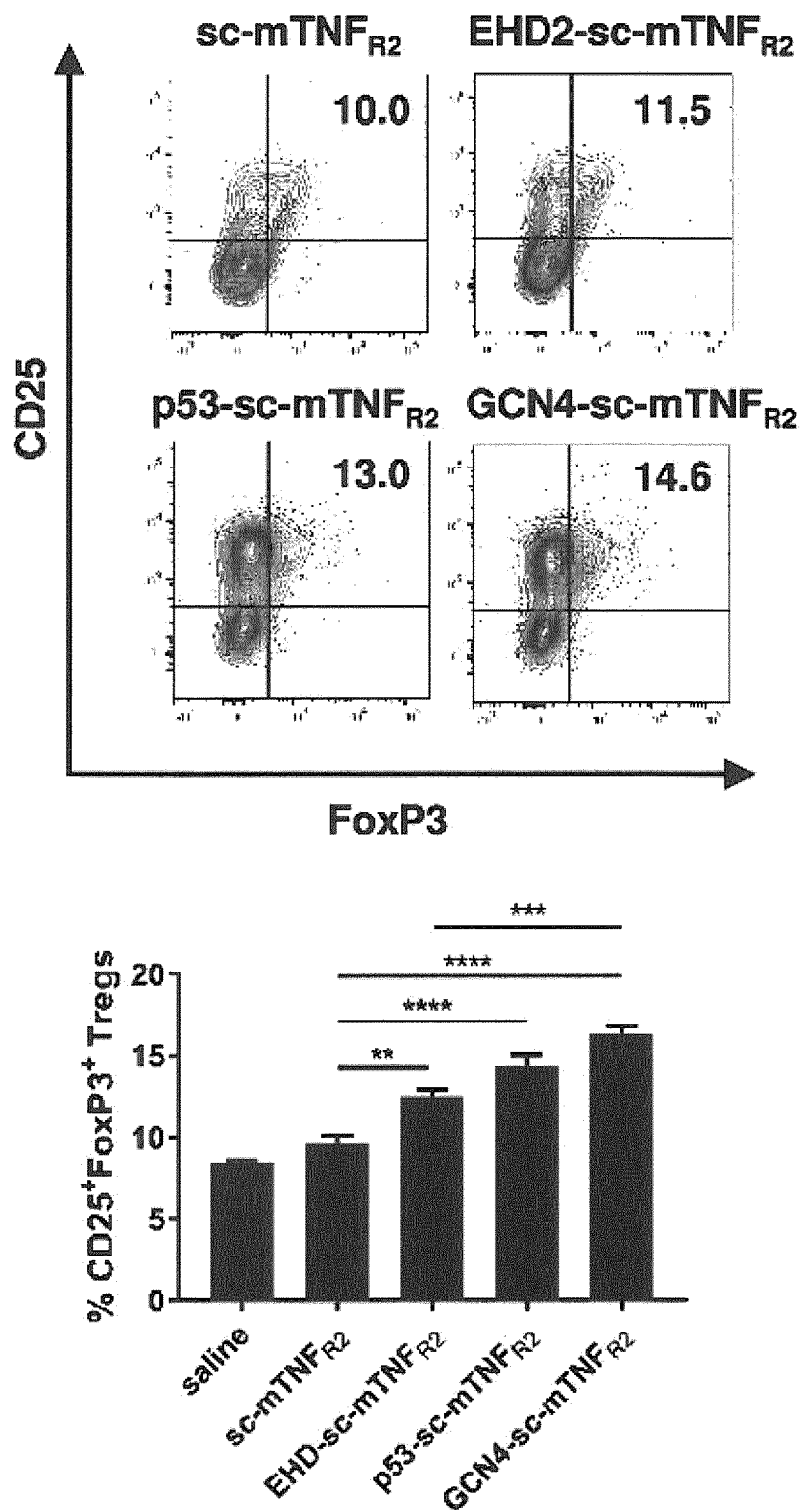

FIG. 13: TNFR2-induced expansion of Tregs. CD3$^+$ T cells isolated from mouse splenocytes via magnetic separation were activated using plate-bound anti-CD3 (5 μg/ml) and cultivated in presence of IL-2 and 0.3 nM of mouse TNF derived TNFR-binding protein complexes for 4 days. Number of CD25$^+$FoxP3$^+$ Tregs was determined by flow cytometry. Shown is a representative donor. Combined data are from three independent experiments (n=3±SEM)

Figure 14:
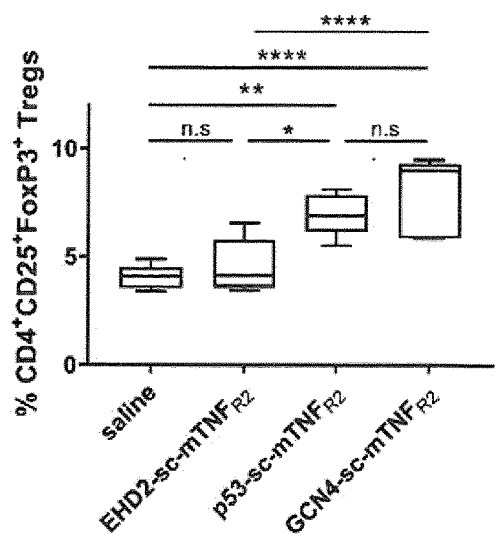
Figure 14:
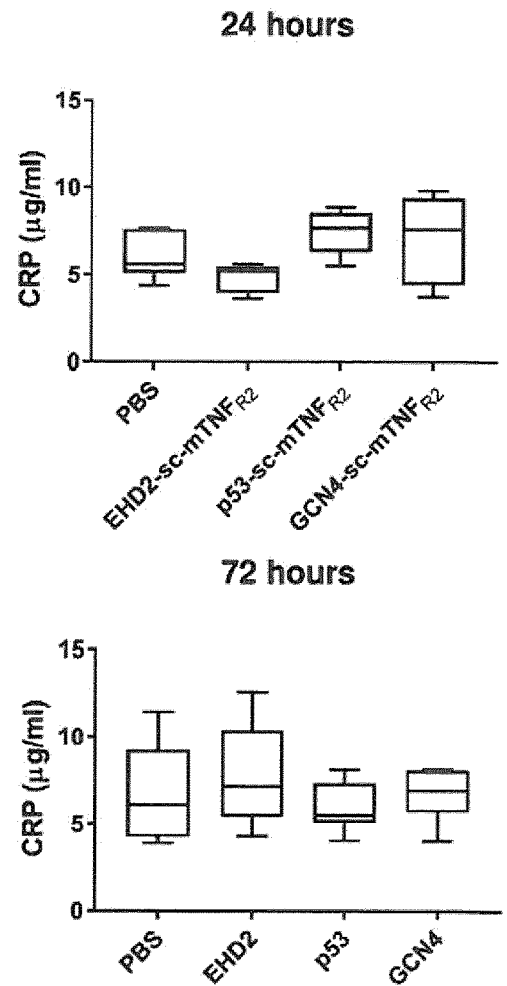

FIG. 14: TNFR2-induced expansion of Tregs in vivo. Mouse TNF derived TNFR-binding protein complexes (1 mg/kg) were administered to C57BL/6 mice via intraperitoneal (i.p.) injection. The injection was repeated on day four. On day seven, spleen cells were isolated and the number of CD4$^+$CD25$^+$FoxP3$^+$ Tregs was determined by flow cytometry (A). Blood was taken from treated animals 24 hrs and 72 hrs post injection of the indicated reagents and CRP serum levels were determined by ELISA (B).

Figure 15:
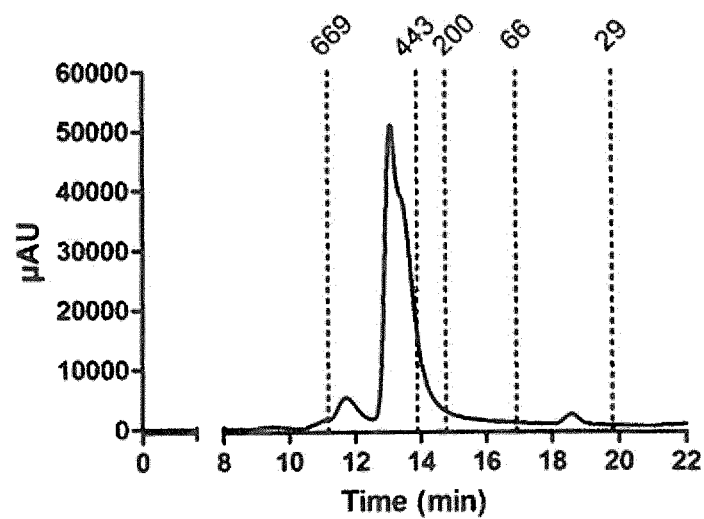
Figure 15:
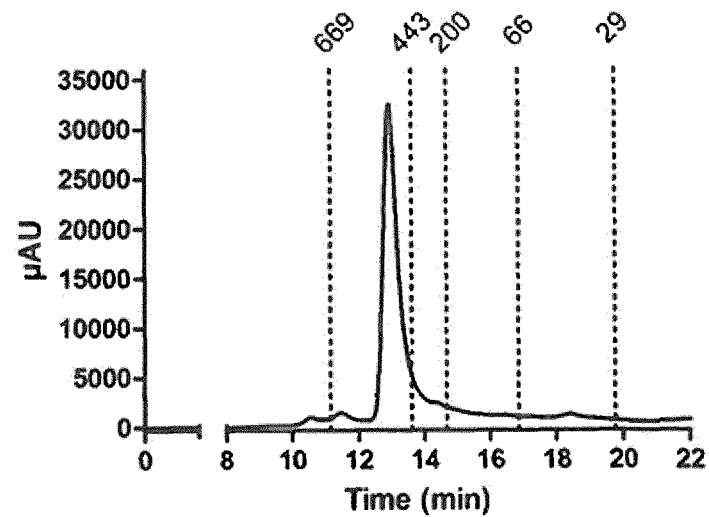
Figure 15:
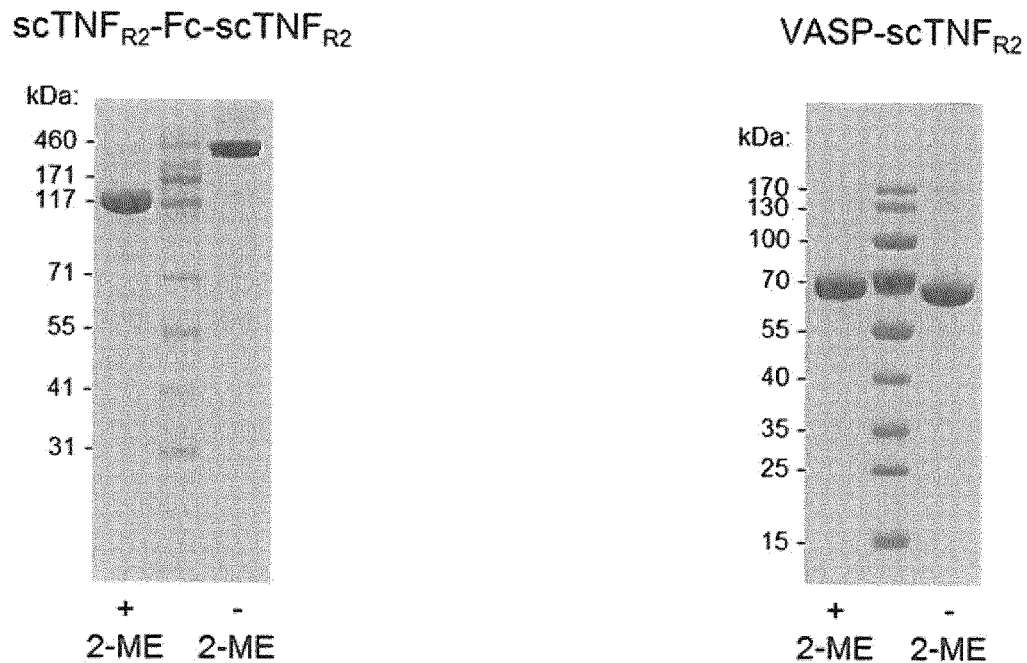
Figure 15:
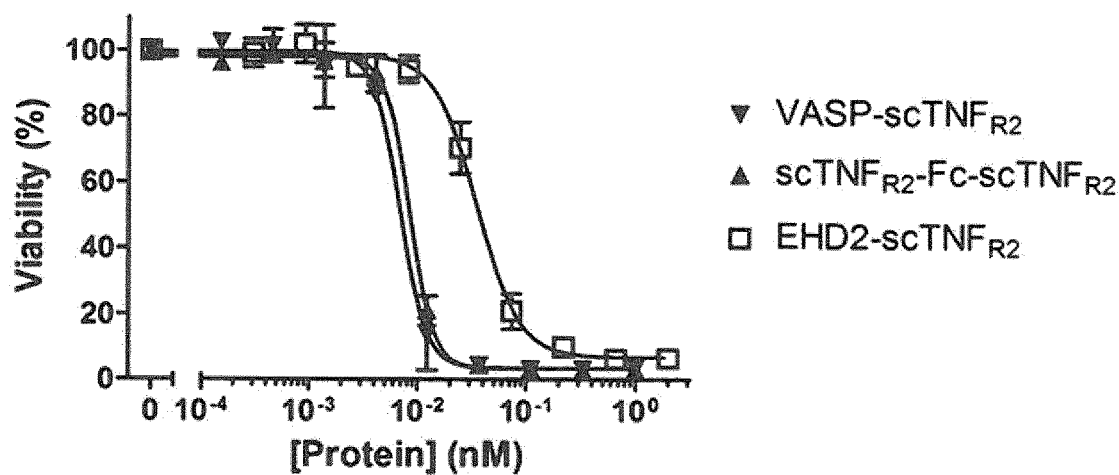

FIG. 15: Dodecavalent TNFR binding complexes comprising scTNF$_{R2}$ linked to Fc as dimerization domain or to the tetramerization domain of VASP. (A) scTNF$_{R2}$-Fc-scTNF$_{R2}$ (according to FIG. 1c) and VASP-scTNF$_{R2}$ (according to FIG. 1f) were produced in HEK293-6E cells, purified by Ni$^{2+}$-NTA IMAC and analyzed under native buffer conditions by size exclusion chromatography on a Tosoh SuperSW mAb HR 7.8×300 mm column. The retention times of globular standard proteins are indicated as dotted lines. (B) The complexes were analyzed by SDS-PAGE followed by Coomassie staining under reducing (+2-ME) and non-reducing conditions (−2-ME). (C) Kym-1 cells were stimulated with dodecavalent scTNF$_{R2}$-Fc-scTNF$_{R2}$, dodecavalent VASP-scTNF$_{R2}$ and compared to hexavalent EHD2-scTNF$_{R2}$. The cell viability was determined by crystal violet assay after 16 h of incubation (n=3±SD).

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

Definitions

The term "protein" as used in the context of the present specification refers to a molecule comprising one or more polypeptides that resume a secondary and tertiary structure and additionally refers to a protein that is made up of several polypeptides, i.e. several subunits, forming quaternary structures. The protein may further comprise one or more modifications, preferably post-translational modifications. These modifications may comprise the addition of a functional groups, chemical modifications or structural changes. Added functional groups may be lipid groups, acyl groups, glycoside groups and the like. Chemical modifications of amino acids may be the conversion of arginine to citruline, the conversion of glutamine to glutamic acid, or asparagine to aspartic acid, and the like. Structural changes of amino acids may be the formation of a disulfide bridge, proteolytic cleavage, racemization, protein splicing, and the like.

The term "protein complex" as used herein, refers to protein constructs created by covalently joining two or more polypeptides or proteins, preferably head-to-tail, i.e. N-terminus to C-terminus or vice versa, resulting in a fusion protein with functional properties derived from the original protein. According to the present invention the term "complex" also encompasses multimeric, e.g. dimeric, trimeric, or tetrameric, complexes of fusion proteins, which are referred to herein as "subunits". Preferably, the subunits of the protein complex associate non-covalently or covalently, e.g. via disulfide bonds.

The term "C-terminus" (also known as the carboxyl-terminus, carboxy-terminus, C-terminal tail, C-terminal end, or COOH-terminus) as referred to within the context of the present invention is the end of an amino acid chain (protein or polypeptide), terminated by a free carboxyl group (—COOH). When the protein is translated from messenger RNA, it is created from N-terminus to C-terminus. The term "N-terminus" (also known as the amino-terminus, $NH_2$-terminus, N-terminal end or amine-terminus) refers to the start of a protein or polypeptide terminated by an amino acid with a free amine group (—$NH_2$). The convention for writing peptide sequences is to put the N-terminus on the left and write the sequence from N- to C-terminus.

A "peptide linker" in the context of the present invention refers to an amino acid sequence which sterically separates two parts or moieties of a complex, e.g. two peptides or proteins. Typically such linker consists of between 1 and 100 amino acids having a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, and a maximum length of at least 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. The indicated preferred minimum and maximum lengths of the peptide linker according to the present invention may be combined, if such a combination makes mathematically sense, e.g. such linker may consist of 1-15, 6-30, 12-40, or 25-75, or 1-100 amino acids. Peptide linkers may also provide flexibility among the two proteins that are linked together. Such flexibility is generally increased if the amino acids are small. Accordingly, flexible peptide linkers comprise an increased content of small amino acids, in particular of glycins and/or alanines, and/or hydrophilic amino acids such as serines, threonines, asparagines and glutamines. Preferably, more than 20%, 30%, 40%, 50%, 60%, 70% or 80% or more of the amino acids of the peptide linker are small amino acids.

The term "consensus sequence" as used within this specification refers to a calculated order of most frequent residues, either nucleotide or amino acid, found at each position in a sequence alignment between two or more sequences. It represents the results of a multiple sequence alignment in which related sequences are compared to each other and similar sequence motifs are calculated. Conserved sequence motifs are depicted as consensus sequences, which indicate identical amino acids, i.e. amino acids identical among the compared sequences, conserved amino acids, i.e. amino acids which vary among the compared amino acid sequence but wherein all amino acids belong to a certain functional or structural group of amino acids, e.g. polar or neutral, and variable amino acids, i.e. amino acids which show no apparent relatedness among the compared sequence.

The consensus sequence of the C-terminus and N-terminus of the THD is a sequence that is located within the TNF-ligand family member sequence, respectively, and is particularly conserved among TNF-ligand family members. These sequences delineate the part of the TNF-ligand family member participating in the trimerization of these ligands and interaction with their corresponding receptor(s). Accordingly, the two consensus sequences serve as C-terminal and N-terminal reference points within a given TNF-ligand family member, which may comprise additional N- or C-terminal amino acids that may not be present in other TNF-ligand family members. Thus, the use of consensus sequences allows to refer to the same region of different TNF-ligand family member without referring to a specific position as the N-terminal and C-terminal end of the fragment of the TNF-ligand family member present in the polypeptides of the invention. It is immediately apparent to the skilled person that the different lengths of N-terminal amino acids preceding the N-terminal consensus sequence in different TNF-ligand family members requires a definition of the C- and N-terminal reference point that is independent of the absolute position of the THD within the respective TNF-ligand family member.

The term "polymerization domain" or "PD" as used herein refers to a protein or polypeptide, a fragment or part of a protein or polypeptide which mediates a close proximity between two or more identical or different protein or polypeptide molecules (monomers) of the invention and thus, enables protein-protein interaction which allows di-, tri-, or tetramerization of two, three, four, respectively, or more structurally similar or different monomers joined by non-covalent or covalent bonds. The polymerization leads to the formation of a macromolecular complex formed by two or more, covalently or non-covalently bound, macromolecules such as proteins. The term "TNF homology domain of TNF-ligand family member proteins" or "THD" as used in the present specification refers to a protein domain shared by all tumor necrosis factor (TNF, formerly known as TNFα or TNF alpha) ligand family members. Homology implies evolutionary lineage from a common ancestor. A homology domain is a conserved part of a given protein sequence and (tertiary) structure that can evolve, function, and exist independently of the rest of the protein chain. It is a structural feature shared by all members of a certain protein family. Each domain forms a compact three-dimensional structure and often can be independently stable, folded and critical for biological activity.

The C-terminus of a THD within the meaning of the present invention is defined by the C-terminal consensus sequence: -S/T/V-F/Y/S-F-G-A/L/V/I-$X_1$ (SEQ ID NO: 1) and the N-terminus is defined by one of the two N-terminal consensus sequences: $X_2$-V/A/F-A-H-V/L/I/Y (SEQ ID NO: 2) or $X_3$-V/W/F/C-A/L-E/Y/Q/H-L (SEQ ID NO: 3), wherein $X_1$ is a non-polar/hydrophobic or polar/neutral amino acid, preferably selected from the group consisting of F, V, Q, A, I, L, and Y; $X_2$ is selected from the group consisting of P, K, V, I, and A; and $X_3$ is selected from the group consisting of D, S, M, and I.

On the basis of a given TNF-ligand family member protein sequence and using above defined C-terminal and N-terminal homology sequences the skilled person can determine for the given TNF-ligand family member protein the THD. Among the members of the TNF family, the position and length of individual THDs vary considerably, but can be defined by the occurrence of conserved amino acid residues as identified by multiple sequence alignments using appropriate software tools (Bodmer et al., 2002). More importantly, crystal structures can reveal distinct interactions between amino acid residues involved in, for example, homotrimerization of TNF family ligands. Informations of such kind can be helpful to refine THDs for given members of the TNF superfamily as described in Bodmer et al., 2002.

Furthermore, functional aspects like protein solubility or bioactivity, such as receptor binding and activation, of engineered protein variants can provide important hints regarding crucial amino acid residues or the minimal length of individual THDs. The term THDs comprises polypeptides based on naturally occurring TNF-ligand family member protein sequences as well as variants thereof, which retain the ability to bind specifically to the receptor(s) of the respective TNF-ligand family member. Preferably such THD variants have an affinity of at least 50% of the wild type THD, more preferably at least 60%, 70%, 80%, 90% and most preferably at least 99%.

TNF-ligand family member proteins comprise a group of multifunctional cytokines that can cause, e.g. programmed cell death (apoptosis), differentiation, cell survival, and immune regulation. TNF is a cytokine that has been implicated e.g. in tumor regression, inflammation, septic shock, and cachexia which is recognized by its specific receptors. Several cells in the body are capable of TNF production, with monocytes being a predominant source of TNF. Nineteen proteins have been identified as part of the TNF-ligand family on the basis of sequence, functional, and structural similarities. All these cytokines seem to form homotrimeric (or heterotrimeric in the case of LT-alpha/beta) complexes that are recognized by their specific receptors.

The following proteins are members of the TNF-ligand super family (TNFSF): TNF, TNF-related apoptosis inducing ligand (TRAIL; TNFSF10), a cytokine that induces apoptosis; CD40L (TNFSFS=tumor necrosis factor superfamily member 5), a cytokine that seems to be important in B-cell development and activation; CD27L (TNFSF7), a cytokine that plays a role in T-cell activation which induces the proliferation of co-stimulated T cells and enhances the generation of cytolytic T cells; CD30L (TNFSF8), a cytokine that induces proliferation of T cells; FasL (TNFSF6), a cell surface protein involved in cell death; 4-1BBL (TNFSF9), an inducible T cell surface molecule that contributes to T-cell stimulation; OX40L (TNFSF4), a cell surface protein that co-stimulates T cell proliferation and cytokine production. Further members of the TNF-ligand family members comprise EDA; LTA (TNFSF1); LTB (TNFSF3); CD153 (TNFSF8); RANKL (TNFSF11); TWEAK (TNFSF12); APRIL (TNFSF13); BAFF (TNFSF13B); LIGHT (TNFSF14); VEGI (TNFSF15); GITRL (TNFSF18).

More information about the sequences of TNF-ligand super family members may be obtained for example from publicly accessible databases such as Genbank. TNF-ligand family members interact with their cognate receptors, e.g. TNF with TNFR1 and TNFR2, TRAIL with TRAILR1 (DR4), TRAILR2 (DRS), TRAILR3 (DcR1), TRAILR4 (DcR2) and OPG. The ligands mediate oligomerization and activation of their respective receptors. The interaction of members of the TNF receptor family with its ligands is characterized by binding of the receptors at the space between two of the three TNF-ligand family member protein monomers of the TNF-ligand family member protein homotrimer, the biological active form of TNF and other members of the TNF-ligand family.

The term "hexameric" or "hexavalent" defines a TNF-ligand family member with six THDs. The term "dodecameric" or "dodecavalent" defines a TNF-ligand family member with twelve THDs.

The term "peptidomimetic" as used within the context of the present specification refers to compounds which can specifically bind antigens, similar to an antibody, but are not structurally related to antibodies. Usually, peptidomimetics are artificial peptides or proteins with a molar mass of about 3 to 20 kDa which comprise one, two or more exposed domains specifically binding to an antigen. Examples include inter alia the LACI-D1 (lipoprotein-associated coagulation inhibitor); affilins, e.g. human-γ B crystalline or human ubiquitin; cystatin; Sac7D from *Sulfolobus acidocaldarius*; lipocalin and anticalins derived from lipocalins; DARPins (designed ankyrin repeat domains); SH3 domain of Fyn; Kunits domain of protease inhibitors; monobodies, e.g. the $10^{th}$ type III domain of fibronectin; adnectins: knottins (cysteine knot miniproteins); atrimers; evibodies, e.g. CTLA4-based binders, affibodies, e.g. three-helix bundle from Z-domain of protein A from *Staphylococcus aureus*; Trans-bodies, e.g. human transferrin; tetranectins, e.g. monomeric or trimeric human C-type lectin domain; microbodies, e.g. trypsin-inhibitor-II; affilins; armadillo repeat proteins. Nucleic acids and small molecules are sometimes considered peptidomimetics as well (aptamers), but not artificial antibodies, antibody fragments and fusion proteins composed from these. Common advantages over antibodies are better solubility, tissue penetration, stability towards heat and enzymes, and comparatively low production costs.

As used herein, the term "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent or parental polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active.

The changes in the nucleotide or amino acid sequence may be nucleotide or amino acid exchanges, insertions, deletions, 5'- or 3' truncations, N- or C-terminal truncations, or any combination of these changes, which may occur at one or several sites. In preferred embodiments, a variant usable in the present invention exhibits a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the nucleotide or amino acid sequence (i.e. exchanges, insertions, deletions, and/or truncations). Amino acid exchanges may be conservative and/or non-conservative. Alternatively or additionally, a "variant" as used herein, can be characterized by a certain degree of sequence identity to the parent polypeptide or parent polynucleotide from which it is derived. More precisely, a protein variant in the context of the present invention exhibits at least 70% sequence identity to its parent polypeptide. A polynucleotide variant in the context of the present invention exhibits at least 70% sequence identity to its parent polynucleotide. Preferably, the sequence identity of protein variants is over a continuous stretch of 20, 30, 40, 45, 50, 60, 70, 80, 90, 100 or more amino acids. Preferably, the sequence identity of polynucleotide variants is over a continuous stretch of 60, 90, 120, 135, 150, 180, 210, 240, 270, 300 or more nucleotides.

The term "at least 70% sequence identity" is used throughout the specification with regard to polypeptide and polynucleotide sequence comparisons. This expression preferably refers to a sequence identity of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide sequence or to the respective reference polynucleotide sequence.

In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. For example, a peptide sequence consisting of 358 amino acids compared to the amino acid sequence of an IgG molecule may exhibit a maximum sequence identity percentage of 80,09% (358/447) while a sequence with a length of 224 amino acids may exhibit a maximum sequence identity percentage of 50,11% (224/447). The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, hmmer.wustl.edu/) or with the CLUSTAL algorithm (Thompson et al. (1994) Nucleic Acids Res. 22:4673-4680) available e.g. on ebi.ac.uk/Tools/clustalw/or on ebi.ac.uk/Tools/clustalw2/index.html or on npsa-pbibcp.fr/cgi-bin/npsa_automat.pl?page=/NPSA/npsa_clustalw.html. Preferred parameters used are the default parameters as they are set on ebi.ac.uk/Tools/clustalw/ or ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215:403-410. BLAST polynucleotide searches are performed with the BLASTN program, score=100, word length=12. BLAST protein searches are performed with the BLASTP program, score=50, word length=3. To obtain gapped alignments for comparative purposes, Gapped BLAST is utilized as described in Altschul et al. (1997) Nucleic Acids Res. 25:3389-3402. When utilizing BLAST and Gapped BLAST programs, the default parameters of the respective programs are used. Sequence matching analysis may be supplemented by established homology mapping techniques like Shuffle-LAGAN (Brudno M. (2003b) Bioinformatics 19 Suppl 1:154-162) or Markov random fields. When percentages of sequence identity are referred to in the present application, these percentages are calculated in relation to the full length of the longer sequence, if not specifically indicated otherwise. "Hybridization" can also be used as a measure of sequence identity or homology between two nucleic acid sequences. A nucleic acid sequence encoding F, N, or M2-1, or a portion of any of these can be used as a hybridization probe according to standard hybridization techniques. Hybridization conditions are known to those skilled in the art and can be found, for example, in Current Protocols in Molecular Biology, John Wiley & Sons, N.Y., 6.3.1-6.3.6, 1991. "Moderate hybridization conditions" are defined as equivalent to hybridization in 2x sodium chloride/sodium citrate (SSC) at 30° C., followed by a wash in 1xSSC, 0.1% SDS at 50° C. "Highly stringent conditions" are defined as equivalent to hybridization in 6X sodium chloride/sodium citrate (SSC) at 45° C., followed by a wash in 0.2xSSC, 0.1% SDS at 65° C.

As used in this specification the term "nucleic acid" comprises polymeric or oligomeric macromolecules, or large biological molecules, essential for all known forms of life. Nucleic acids, which include DNA (deoxyribonucleic acid) and RNA (ribonucleic acid), are made from monomers known as nucleotides. Most naturally occurring DNA molecules consist of two complementary biopolymer strands coiled around each other to form a double helix. The DNA strand is also known as polynucleotides consisting of nucleotides. Each nucleotide is composed of a nitrogencontaining nucleobase as well as a monosaccharide sugar called deoxyribose or ribose and a phosphate group. Naturally occurring nucleobases comprise guanine (G), adenine (A), thymine (T), uracil (U) or cytosine (C). The nucleotides are joined to one another in a chain by covalent bonds between the sugar of one nucleotide and the phosphate of the next, resulting in an alternating sugar-phosphate backbone. If the sugar is desoxyribose, the polymer is DNA. If the sugar is ribose, the polymer is RNA.

Typically, a polynucleotide is formed through phosphodiester bonds between the individual nucleotide monomers. In the context of the present invention the term "nucleic acid" includes but is not limited to ribonucleic acid (RNA), deoxyribonucleic acid (DNA), and mixtures thereof such as e.g. RNA-DNA hybrids (within one strand), as well as cDNA, genomic DNA, recombinant DNA, cRNA and mRNA. A nucleic acid may consist of an entire gene, or a portion thereof, the nucleic acid may also be a miRNA, siRNA, or a piRNA.

As used in this specification the term "vector", also referred to as an expression construct, is usually a plasmid or virus designed for protein expression in cells. The vector is used to introduce a specific gene into a target cell, and can use the cell's mechanism for protein synthesis to produce the protein encoded by the gene. The expression vector is engineered to contain regulatory sequences that act as enhancer and promoter regions and lead to efficient transcription of the gene carried on the expression vector. The goal of a well-designed expression vector is the production of significant amount of stable messenger RNA, and therefore proteins. Examples of suitable vectors include but are not limited to plasmids, cosmids, phages, viruses or artificial chromosomes. An example for a commonly used expression vector is pGEX-4T2.

The term "pharmaceutical composition" as used in the present application refers to a substance and/or a combination of substances being used for the identification, prevention or treatment of a tissue status or disease. The pharmaceutical composition is formulated to be suitable for administration to a patient in order to prevent and/or treat disease. Further a pharmaceutical composition refers to the combination of an active agent with a carrier, inert or active, making the composition suitable for therapeutic use. Pharmaceutical compositions can be formulated for oral, parenteral, topical, inhalative, rectal, sublingual, transdermal, subcutaneous or vaginal application routes according to their chemical and physical properties. Pharmaceutical compositions comprise solid, semisolid, liquid, transdermal therapeutic systems (TTS). Solid compositions are selected from the group consisting of tablets, coated tablets, powder, granulate, pellets, capsules, effervescent tablets or transdermal therapeutic systems. Also comprised are liquid compositions, selected from the group consisting of solutions, syrups, infusions, extracts, solutions for intravenous application, solutions for infusion or solutions of the carrier systems of the present invention. Semisolid compositions that can be used in the context of the invention comprise emulsion, suspension, creams, lotions, gels, globules, buccal tablets and suppositories.

The term "active agent" refers to the substance in a pharmaceutical composition or formulation that is biologically active, i.e. that provides pharmaceutical value. A pharmaceutical composition may comprise one or more active agents which may act in conjunction with or independently of each other. The active agent can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

The term "disease" and "disorder" are used interchangeably herein, referring to an abnormal condition, especially an abnormal medical condition such as an illness or injury, wherein a cell, a tissue, an organ, or an individual is not able to efficiently fulfil its function anymore. Typically, but not necessarily, a disease is associated with specific symptoms or signs indicating the presence of such disease. The presence of such symptoms or signs may thus, be indicative for a cell, a tissue, an organ, or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a cell, tissue, organ or individual/patient to fulfil its function efficiently, whereas the "bettering" of a disease is typically characterised by an increase in the ability of a cell, tissue, an organ or an individual/patient to fulfil its function efficiently.

The term "hyperproliferative disorder" as used in the present application refers to disorders wherein the cell division of the cells is increased in relation to normal tissue. Such disorders are characterized by an abnormal proliferation (production) i.e. overproduction of cells. Hyperproliferative disorders comprise tumor diseases. Tumor diseases may comprise benign or malignant tumors wherein malignant tumor diseases are referred to as cancer. The term hyperproliferative disorder comprises cancers as well as pre-cancerous disorders. Cancer comprises proliferative disorders of mesenchymal origin, i.e. connective tissue (sarcomas) and of epithelial tissues (carcinomas). Common examples of sarcomas are osteosarcoma, chondrosarcoma, liposarcoma, leiomyosarcoma, angiosarcoma and fibrosarcoma and sarcomas of the gastrointestinal tract (GIST). Examples for carcinomas are carcinomas of the skin, testis, liver, gastrointestinal tract such as esophagus, stomach, pancreas, and colon, nasopharynx, bladder, cervix, ovarian, urethra, bladder; prostate and other genitourinary carcinomas, lung, kidney, endocrine tissues such as thyroid and pituitary gland, teratocarcinomas, carcinomas of the brain. Malignancies of the hematologic system are classified as lymphoma or leukemia. Inflammation orchestrates the microenvironment around tumors, contributing to proliferation, survival and migration of cancer cells, thus potentially promoting malignant disease.

Inflammation is in principle a protective immunovascular response that involves immune cells, blood vessels, and a plethora of molecular mediators. The purpose of inflammation is to eliminate the initial cause of cell injury, clear out necrotic cells and tissues damaged from the original insult and the inflammatory process, and to initiate tissue repair. The term "inflammatory disorder" as used in the context of the present invention refers to a situation wherein a physiological inflammatory response turns into a potentially harmful effect for the body. Inflammatory disorders causing damage to normal tissues comprise but are not limited to autoimmune disorders and neurodegenerative diseases.

The term "neurodegenerative disorder" as used in the present invention relates to a disorder involving the progressive loss of structure and function of neurons, including death of neurons. Neurodegenerative disease occurs typically as a result of a neurodegenerative process. Neurodegenerative diseases cause problems with movement (ataxias) or mental functioning (dementias).

The term "infectious diseases" as used in the present invention relates to a disorder caused by an infectious agent including including viruses, viroids, prions, bacteria, nematodes such as parasitic roundworms and pinworms, arthropods such as ticks, mites, fleas, and lice, fungi such as ringworm, and other macroparasites such as tapeworms and other helminths. Mammalian hosts react to infections with an innate response, commonly involving inflammation. Disease can arise if the host's protective immune mechanisms are compromised and the organism inflicts damage on the host. Microorganisms and parasites can cause tissue damage by releasing a variety of toxins or destructive enzymes.

Embodiments

In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. In the work leading to the present invention, it was surprisingly shown that the complexes of the present invention show superior activities in activating TNFRs.

Based on these results, the present invention relates in a first aspect to a tumour necrosis factor receptor (TNFR) binding protein complex comprising 12 or more, preferably 12, 13, 14, 15, 16, 17, 18, 19, 21, 22, 23, 24, 25, 26, 27, 28, 29 or 30 protein ligands (PLs) that specifically bind to the extracellular part of the same TNFR. Preferably, the TNFR binding protein complex specifically binds to TNFR2. Accordingly, it is preferred that all PLs of the TNFR binding protein complex specifically bind to TNFR2.

The inventors successfully constructed a stable TNFR binding protein complex comprising at least 12 PLs. In addition, the inventors surprisingly found out that a complex comprising 12 or more PLs displays an increased specific binding when compared to a complex comprising 6 PLs, thereby being effective TNFR agonists exerting specific bioactivities of up to >10fold higher compared to hexavalent PLs.

Highly potent compounds are necessary to be therapeutically efficient. This is of special relevance for e.g. neurodegenerative diseases, were neuroprotective compounds need to act in the central nervous system (CNS). The blood-brain-barrier, a tight barrier separating the bloodstream from the brain and spinal cord, limits the transport of therapeutics to the CNS. Due to the limited drug amount transported to the CNS, neuroprotective compounds, such as TNFR2 agonists, with direct beneficial effects on neuronal or glial cells, need to be highly potent to exert therapeutic effects. This may be favourably achieved with the complexes of the present invention.

As indicated above, the active sites/binding sites are conserved among the TNFRs and their corresponding TNF ligands. Accordingly, the principle of combining at least 12 PLs that specifically bind to the extracellular part of the same TNFR may be applied to any member of the TNF ligand family, from which follows that a stable ligand complex with high agonistic activity may be obtained.

It is preferred that the TNFR binding protein complex of the present invention comprises between 12 to 30, preferably 12 to 18, more preferably 12 to 15 PLs. It is more preferred that the TNFR binding protein complex of the present invention comprises 15 PLs. It is particularly preferred that the TNFR binding protein complex of the present invention comprises 12 PLs.

The PLs of the TNFR binding protein complex according to the present invention may be selected independently of each other; e.g. the 12 to 30, preferably 12 to 18 PLs may have the same binding specificity, i.e. bind to the same target, preferably are identical or may be different. Otherwise, it is particularly preferred that all 12 to 30, preferably 12 to 18, more preferably 12 to 15 PLs, most preferred 12 PLs have the same binding specificity, preferably are identical. If the TNFR binding protein complex specifically binds to TNFR2 it may have 12 to 30, preferably 12 to 18, more preferably 12 to 15 PLs, most preferred 12 PLs have TNFR2 binding specificity, more preferably are identical PLs.

If the binding specificity is not directed at TNFR2 it is preferred that the TNFR binding protein complex according to the present invention comprises more than 15 PLs. Preferably 15 to 30, preferably 15 to 24, more preferably 15 to 18 PLs. It is also preferred that all of the PLs have the same binding specificity, more preferably are identical.

In other words, the PLs of the TNFR binding protein complex of the present invention may be heterologues or may be homologues. Preferably, the PLs of the TNFR binding complex of the present invention are homologues.

It is further preferred that in the TNFR binding protein complex of the present invention, between 2 to 6 PLs form a protein ligand group (PLG) with the following structure:

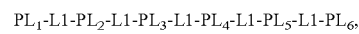

wherein
any of $PL_4$ to $PL_6$, and/or L1 may be absent or present, preferably $PL_4$ to PL6 are absent and two L1 are present between $PL_1$ and $PL_2$ and $PL_2$ and $PL_3$, respectively; L1 in each case independently means a peptide linker.

It is preferred that 3 PLs form the PLG. It is particularly preferred that in the TNFR binding protein complex of the present invention 3 PLs form a PLG with the following structure:

It is further preferred that the TNFR binding protein complex of the present invention comprises between 2 to 6 PLGs and each PLG comprises between 2 to 6 PLs, under the proviso that the total number of PLs of the protein complex of the present invention is 12 or more.

It is preferred that the PLs and the linkers L1 of the complex of the present invention are connected via a covalent bond.

It is more preferred that the TNFR binding protein complex of the present invention comprises between 4 to 6 PLGs and each PLG comprises 3 PLs. It is even more preferred that the TNFR binding protein complex of the present invention comprises 4 or 6 PLGs and each PLG comprises 3 PLs.

It is further preferred that in the TNFR binding complex of the present invention, the PLGs are linked to each other by a peptide linker 2 (L2) to form a PLG-multimer.

It is preferred that the TNFR binding complex of the present invention 2 PLGs are linked to each other by a peptide linker L2 to form the following structure:

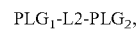

preferably wherein $PLG_1$ and $PLG_2$ are each formed by 3 PLs.

It is preferred that in the TNFR binding complex of the present invention 3 PLGs are linked to each other by a peptide linker L2 to form the following structure:

PLG$_1$-L2-PLG$_2$-L2-PLG$_3$, wherein PLG$_1$ to PLG$_3$ are each formed by 3 PLs.

It is preferred that the TNFR binding complex of the present invention 4 PLGs are linked to each other by a peptide linker L2 to form the following structure:

PLG$_1$-L2-PLG$_2$-L2-PLG$_3$-L2-PLG$_4$, preferably wherein PLG$_1$ to PLG$_4$ are each formed by 3 PLs.

It is preferred that the PLGs and the linkers L2 of the complex of the present invention are connected via a covalent bond.

It is preferred that in the TNFR binding protein complex of the present invention further comprises two or more polymerization domains (PD).

Preferably, each of the two, three, four or more PDs are linked via their N- and/or C-terminus to a PLG or a PLG-multimer, optionally by a peptide linker 3 (L3). Thereby, two, three, four or more subunits of the complex of the present invention are formed. In other words, for each PD a subunit of the complex of the present invention is formed. It is noted that PLGs of different subunits are preferably not linked to each other, particularly not covalently.

Preferably, a subunit of the complex of the present invention may have the following structures:

PD-L3-PLG$_1$, or

PLG$_1$-L3-PD, preferably wherein PLG$_1$ is formed by 3 PLs.

Preferably, a subunit of the complex of the present invention may have the following structures:

PD-L3-PLG$_1$-L2-PLG$_2$, or

PLG$_1$-L2-PLG$_2$-L3-PD, preferably wherein PLG$_1$ and PLG$_2$ are each formed by 3 PLs.

Preferably, in a TNFR binding protein complex of the invention the two, three, four or more PDs are each inserted between two PLGs. More preferably, the two, three, four or more PDs are each inserted between two PLGs and linked to the PGLs by a peptide linker L3. Preferably, a subunit of the complex of the present invention comprising a PD inserted between two PLGs by peptides L3 may have one of the following structures:

PLG$_1$-L3-PD-L3-PLG$_2$ or

PLG$_1$-L2-PLG$_2$-L3-PD-L3-PLG$_3$-L2-PLG$_4$ preferably wherein PLG$_1$, PLG$_2$, PLG$_3$ and PLG$_4$ are each formed by 3 PLs.

More preferably, in a TNFR binding protein complex the two, three, four or more PDs are each inserted between two PLGs via peptide linkers L3 and L4, respectively. Preferably, L3 and L4 are not identical. Preferably, L3 and L4 are identical.

Preferably, in a subunit a PD is inserted between two PLGs may have one of the following structures:

PLG$_1$-L3-PD-L4-PLG$_2$, or

PLG$_1$-L4-PD-L3-PLG$_2$, preferably wherein PLG$_1$ and PLG$_2$ are each formed by 3 PLs, and preferably wherein L3 and L4 are not identical.

Preferably, in a subunit a PD is inserted between two PLGs may have one of the following structures:

PLG$_1$-L2-PLG$_2$-L3-PD-L4-PLG$_3$-L2-PLG$_4$, or

PLG$_1$-L2-PLG$_2$-L4-PD-L3-PLG$_3$-L2-PLG$_4$, preferably wherein PLG$_1$, PLG$_2$, PLG$_3$, and PLG$_4$ are each formed by 3 PLs, and preferably wherein L3 and L4 are not identical.

It is preferred that the PLGs and PD are connected with the linkers L3 and L4 of the complex of the present invention via a covalent bond.

Preferably, the PD is selected from the group consisting of a dimerization domain, a trimerization domain or a tetramerization domain. It is understood that when the complex of the present invention comprises two or more PD, the total number of PLs is 12 or more.

Preferably, the dimerization domain is selected from the group consisting of heavy chain domain 2 (CH2) of IgM (MHD2) or IgE (EHD2), immunoglobulin Fc region, heavy chain domain 3 (CH3) of IgG or IgA, heavy chain domain 4 (CH4) of IgM or IgE, Fab, Fab$_2$, leucine zipper motifs, barnase-barstar dimers, miniantibodies, and ZIP miniantibodies. Preferably, the dimerization domain is selected from the group consisting of EHD2 or an immunoglobulin Fc region. Preferably, the dimerization domain is EHD2. Preferably, the dimerization domain is a immunoglobulin Fc region. The immunoglobulin Fc region is the constant part of an IgG antibody that is naturally present in a dimeric form, covalently stabilized by two disulfide bonds, and can be used for dimerization of proteins. In this function, Fc can be present either in a wild-type form or preferably in a mutant form with abolished ADCC/CDC functionality (antibody-dependent cell-mediated cytotoxicity/complement-dependent cytotoxicity).

Preferably, the trimerization domain is selected from the group consisting of tenascin C (TNC), the trimerization region of the C-terminal noncollagenous domain (NC1) of collagen XVIII, Fab3-like molecules, and TriBi-minibodies. Preferably, the trimerization domain is a Fab3-like molecule.

Preferably, the tetramerization domain is selected from the group consisting of the tetramerization domain of p53, the tetramerization domain of the general control protein 4 (GCN4), the tetramerization domain of ena/VASP (enabled/vasodilator-stimulated phosphoprotein) family of actin regulating proteins or synthetic variants derived thereof, tandem diabodies, and di-diabodies. Preferably, the tetramerization domain is selected from the group consisting of the tetramerization domain of p53, the tetramerization domain of the general control protein 4 (GCN4) or the tetramerzation domain of ena/VASP. Preferably, the tetramerization domain is selected from the group consisting of the tetramerization domain of p53 and the tetramerization domain of the general control protein 4 (GCN4). Preferably, the tetramerization domain is the tetramerization domain of p53. Preferably, the tetramerization domain is the tetramerization domain of the general control protein 4 (GCN4). Preferably, the tetramerization domain is the tetramerization domain of ena/VASP.

Preferably, each dimerization domain and trimerization domain comprises at least one amino acid residue capable of forming a covalent bond to at least one amino acid residue in another PD, preferably a Cys residue.

The peptide linkers L1, L2, L3, and L4 of the present invention are preferably glycine (G) rich peptide linkers, i.e. are amino acid sequences with a high glycine content of more than 50%; e.g. from at least 60 to 80%, for example of about 75%. Other amino acids which may be present in the peptide linker are for example serine residues or less preferably alanine residues or glutamine residues.

L1, L2, L3, or L4, respectively, may be selected independently of each other; e.g. the two or more linkers L1 may have an identical sequence or may have different sequences (in terms of sequence length and/or sequence amino acids), the two or more linkers L2 may have an identical sequence or may have different sequences (in terms of sequence length and/or sequence amino acids), and so on. However, it is preferred that L1, L2, L3, or L4, respectively, are identical.

L1 has a length of between 2 to 20 amino acids, preferably 2 to 15 amino acids, more preferably 3 to 10 amino acids and most preferably of 3 to 5 amino acids. L1 may comprise one or more repetitive units selected from the group consisting of $(GGS)_p$, $(GGGS)_n$ or $(GGSGG)_m$, wherein p is an integer between 1 and 6, n is an integer between 1 and 5 and m is an integer between 1 to 4. L1 may be selected from the group consisting of SEQ ID NO: 4 to 20. A preferred linker L1 has SEQ ID NO: 15

L2 has a length of between 4 to 32 amino acids, preferably 8 to 28 amino acids. L2 may comprise one or more repetitive units selected from the group consisting of $(GGS)_p$, $(GGGS)_n$ or $(GGSGG)_m$, wherein p is an integer between 1 and 10, n is an integer between 1 and 8 and m is an integer between 1 to 6. A particularly preferred linker L2 is selected from the group consisting of SEQ ID NO: 21 to 41.

L3 has a length of between 4 to 32 amino acids, preferably 8 to 28 amino acids. L3 optionally comprises at least one glycosylation motif, preferably at least one motif is glycosylated. L3 may comprise one or more repetitive units selected from the group consisting of $(GGS)_p$, $(GGGS)_n$ or $(GGSGG)_m$, wherein p is an integer between 1 and 10, n is an integer between 1 and 8 and m is an integer between 1 to 6. A particularly preferred linker L3 is selected from the group consisting of SEQ ID NO: 21 to 41.

L4 has a length of between 4 to 32 amino acids, preferably 8 to 28 amino acids. L4 optionally comprises at least one glycosylation motif, preferably at least one motif is glycosylated. Preferably, L4 may comprise one or more repetitive units selected from the group consisting of $(GGS)_p$, $(GGGS)_n$ or $(GGSGG)_m$, wherein p is an integer between 1 and 10, n is an integer between 1 and 8 and m is an integer between 1 to 6. A particularly preferred linker L4 is selected from the group consisting of SEQ ID NO: 21 to 41.

In embodiments, wherein the complex of the present invention comprises L3 and L4, it is preferred that L3 and L4 are not identical in terms of sequence length and sequence amino acids.

Preferably, each PL is independently of each other selected from the group consisting of a TNF homology domain of a TNF-ligand family member protein (THD), a scaffold-protein and a peptidomimetic, wherein preferably the TNF homology domain is a human TNF homology domain. Preferably, the PL is a TNF homology domain of a TNF-ligand family member protein (THD), preferably wherein the TNF homology domain is a human TNF homology domain. Preferably, each PL is a TNF homology domain of a TNF-ligand family member protein (THD). Preferably, each PL is a TNF homology domain of a TNF-ligand family member protein (THD), wherein the TNF homology domain is a human TNF homology domain.

Preferably, the TNF-ligand family member protein is selected from the group consisting of TNF, TNF-related apoptosis inducing ligand (TRAIL or TNFSF10, tumor necrosis factor superfamily member), CD40L (TNFSF5), CD27L (TNFSF7), CD30L (TNFSF8), FasL (TNFSF6), 4-1BBL (TNFSF9), OX40L (TNFSF4), EDA; LTA (TNFSF1), LTB (TNFSF3), CD153 (TNFSF8), RANKL (TNFSF11), TWEAK (TNFSF12), APRIL (TNFSF13), BAFF (TNFSF13B), LIGHT (TNFSF14), VEGI (TNFSF15), and GITRL (TNFSF18). Preferably, the TNF-ligand family member protein is selected from the group consisting of LT, TNF or TRAIL. More preferably, the TNF-ligand family member protein is TNF or LTA.

Preferably, the TNF-ligand family member protein comprises consists of one of the sequences according to SEQ ID NO: 42 to 79, as indicated in Table 1 below, or functional variants thereof. Preferably, the TNF-ligand family member protein comprises consists of one of the sequences according to human sequences SEQ ID NO: 42 to 48, 50 to 54 and 56 to 79 and functional variants thereof. The variants includes natural or artificial variations thereof or respective orthologs from other species. Preferred are orthologs from other mammalian species such as chimpanzee, mouse, rat, swine, etc.

TABLE 1

Possible components A

| Name: | AA Position | SEQ ID NO: | Sequence |
|---|---|---|---|
| TNF | 89-233 | 42 | VAHVVANPQAEGQLQWLNRRANALLANGVE LRDNQLVVPSEGLYLIYSQVLFKGQGCPSTHV LLTHTISRIAVSYQTKVNLLSAIKSPCQRETPEG AEAKPWYEPIYLGGVFQLEKGDRLSAEINRPD YLDFAESGQVYFGIIAL |
| TNF | 80-233 | 43 | SSRTPSDKPVAHVVANPQAEGQLQWLNRRAN ALLANGVELRDNQLVVPSEGLYLIYSQVLFKG QGCPSTHVLLTHTISRIAVSYQTKVNLLSAIKS PCQRETPEGAEAKPWYEPIYLGGVFQLEKGDR LSAEINRPDYLDFAESGQVYFGIIAL |
| TRAIL | 120-281 | 44 | QRVAAHITGTRGRSNTLSSPNSKNEKALGRKI NSWESSRSGHSFLSNLHLRNGELVIHEKGFYYI |

TABLE 1-continued

Possible components A

| Name: | AA Position | SEQ ID NO: | Sequence |
|---|---|---|---|
| | | | YSQTYFRFQEEIKENTKNDKQMVQYIYKYTSY PDPILLMKSARNSCWSKDAEYGLYSIYQGGIF ELKENDRIFVSVTNEHLIDMDHEASFFGAFLV G |
| TRAIL | 118-281 | 45 | GPQRVAAHITGTRGRSNTLSSPNSKNEKALGR KINSWESSRSGHSFLSNLHLRNGELVIHEKGFY YIYSQTYFRFQEEIKENTKNDKQMVQYIYKYT SYPDPILLMKSARNSCWSKDAEYGLYSIYQGG IFELKENDRIFVSVTNEHLIDMDHEASFFGAFL VG |
| TRAIL | 116-281 | 46 | ERGPQRVAAHITGTRGRSNTLSSPNSKNEKAL GRKINSWESSRSGHSFLSNLHLRNGELVIHEKG FYYIYSQTYFRFQEEIKENTKNDKQMVQYIYK YTSYPDPILLMKSARNSCWSKDAEYGLYSIYQ GGIFELKENDRIFVSVTNEHLIDMDHEASFFGA FLVG |
| TRAIL | 114-281 | 47 | VRERGPQRVAAHITGTRGRSNTLSSPNSKNEK ALGRKINSWESSRSGHSFLSNLHLRNGELVIHE KGFYYIYSQTYFRFQEEIKENTKNDKQMVQYI YKYTSYPDPILLMKSARNSCWSKDAEYGLYSI YQGGIFELKENDRIFVSVTNEHLIDMDHEASFF GAFLVG |
| TRAIL | 95-281 | 48 | TSEETISTVQEKQQNISPLVRERGPQRVAAHIT GTRGRSNTLSSPNSKNEKALGRKINSWESSRS GHSFLSNLHLRNGELVIHEKGFYYIYSQTYFRF QEEIKENTKNDKQMVQYIYKYTSYPDPILLMK SARNSCWSKDAEYGLYSIYQGGIFELKENDRIF VSVTNEHLIDMDHEASFFGAFLVG |
| mouse TRAIL | 99-291 | 49 | TFQDTISTVPEKQLSTPPLPRGGRPQKVAAHIT GITRRSNSALIPISKDGKTLGQKIESWESSRKG HSFLNHVLFRNGELVIEQEGLYYIYSQTYFRFQ EAEDASKMVSKDKVRTKQLVQYIYKYTSYPD PIVLMKSARNSCWSRDAEYGLYSIYQGGLFEL KKNDRIFVSVTNEHLMDLDQEASFFGAFLIN |
| FasL (CD95L) | 144-281 | 50 | RKVAHLTGKSNSRSMPLEWEDTYGIVLLSGV KYKKGGLVINETGLYFVYSKVYFRGQSCNNL PLSHKVYMRNSKYPQDLVMMEGKMMSYCTT GQMWARSSYLGAVFNLTSADHLYVNVSELSL VNFEESQTFFGLYKL |
| FasL (CD95L) | 142-281 | 51 | ELRKVAHLTGKSNSRSMPLEWEDTYGIVLLSG VKYKKGGLVINETGLYFVYSKVYFRGQSCNN LPLSHKVYMRNSKYPQDLVMMEGKMMSYCT TGQMWARSSYLGAVFNLTSADHLYVNVSELS LVNFEESQTFFGLYKL |
| FasL (CD95L) | 137-281 | 52 | PPEKKELRKVAHLTGKSNSRSMPLEWEDTYGI VLLSGVKYKKGGLVINETGLYFVYSKVYFRG QSCNNLPLSHKVYMRNSKYPQDLVMMEGKM MSYCTTGQMWARSSYLGAVFNLTSADHLYV NVSELSLVNFEESQTFFGLYKL |
| FasL (CD95L) | 130-281 | 53 | QIGHPSPPPEKKELRKVAHLTGKSNSRSMPLE WEDTYGIVLLSGVKYKKGGLVINETGLYFVYS KVYFRGQSCNNLPLSHKVYMRNSKYPQDLV MMEGKMMSYCTTGQMWARSSYLGAVFNLTS ADHLYVNVSELSLVNFEESQTFFGLYKL |
| FasL (CD95L) | 120-281 | 54 | QMHTASSLEKQIGHPSPPPEKKELRKVAHLTG KSNSRSMPLEWEDTYGIVLLSGVKYKKGGLVI NETGLYFVYSKVYFRGQSCNNLPLSHKVYMR NSKYPQDLVMMEGKMMSYCTTGQMWARSS YLGAVFNLTSADHLYVNVSELSLVNFEESQTF FGLYKL |

TABLE 1-continued

Possible components A

| Name: | AA Position | SEQ ID NO: | Sequence |
|---|---|---|---|
| mouse FasL (CD95L) | 137-279 | 55 | EKKEPRSVAHLTGNPHSRSIPLEWEDTYGTALI SGVKYKKGGLVINETGLYFVYSKVYFRGQSC NNQPLNHKVYMRNSKYPEDLVLMEEKRLNY CTTGQIVVAHSSYLGAVFNLTSADHLYVNISQL SLINFEESKTFFGLYKL |
| LT alpha | 59-205 | 56 | SNLKPAAHLIGDPSKQNSLLWRANTDRAFLQD GFSLSNNSLLVPTSGIYFVYSQVVFSGKAYSPK ATSSPLYLAHEVQLFSSQYPFHVPLLSSQKMV YPGLQEPWLHSMYHGAAFQLTQGDQLSTHTD GIPHLVLSPSTVFFGAFAL |
| LT beta | 82-244 | 57 | DLSPGLPAAHLIGAPLKGQGLGWETTKEQAFL TSGTQFSDAEGLALPQDGLYYLYCLVGYRGR APPGGGDPQGRSVTLRSSLYRAGGAYGPGTPE LLLEGAETVTPVLDPARRQGYGPLWYTSVGF GGLVQLRRGERVYVNISHPDMVDFARGKTFF GAVMVG |
| LT beta | 86-244 | 58 | GLPAAHLIGAPLKGQGLGWETTKEQAFLTSGT QFSDAEGLALPQDGLYYLYCLVGYRGRAPPG GGDPQGRSVTLRSSLYRAGGAYGPGTPELLLE GAETVTPVLDPARRQGYGPLWYTSVGFGGLV QLRRGERVYVNISHPDMVDFARGKTFFGAVM VG |
| CD30L | 97-234 | 59 | KSWAYLQVAKHLNKTKLSWNKDGILHGVRY QDGNLVIQFPGLYFIICQLQFLVQCPNNSVDLK LELLINKHIKKQALVTCESGMQTKHVYQNLS QFLLDYLQVNTTISVNVDTFQYIDTSTFPLENV LSIFLYSNSD |
| CD30L | 102-234 | 60 | LQVAKHLNKTKLSWNKDGILHGVRYQDGNL VIQFPGLYFIICQLQFLVQCPNNSVDLKLELLIN KHIKKQALVTCESGMQTKHVYQNLSQFLLD YLQVNTTISVNVDTFQYIDTSTFPLENVLSIFLY SNSD |
| CD40L | 116-261 | 61 | GDQNPQIAAHVISEASSKTTSVLQWAEKGYYT MSNNLVTLENGKQLTVKRQGLYYIYAQVTFC SNREASSQAPFIASLCLKSPGRFERILLRAANT HSSAKPCGQQSIHLGGVFELQPGASVFVNVTD PSQVSHGTGFTSFGLLKL |
| CD40L | 113-261 | 62 | MQKGDQNPQIAAHVISEASSKTTSVLQWAEK GYYTMSNNLVTLENGKQLTVKRQGLYYIYAQ VTFCSNREASSQAPFIASLCLKSPGRFERILLRA ANTHSSAKPCGQQSIHLGGVFELQPGASVFVN VTDPSQVSHGTGFTSFGLLKL |
| OX40L | 52-183 | 63 | VSHRYPRIQSIKVQFTEYKKEKGFILTSQKEDEI MKVQNNSVIINCDGFYLISLKGYFSQEVNISLH YQKDEEPLFQLKKVRSVNSLMVASLTYKDKV YLNVTTDNTSLDDFHVNGGELILIHQNPGEFC VL |
| OX40L | 55-183 | 64 | RYPRIQSIKVQFTEYKKEKGFILTSQKEDEIMK VQNNSVIINCDGFYLISLKGYFSQEVNISLHYQ KDEEPLFQLKKVRSVNSLMVASLTYKDKVYL NVTTDNTSLDDFHVNGGELILIHQNPGEFCVL |
| RANKL | 161-317 | 65 | EAQPFAHLTINATDIPSGSHKVSLSSWYHDRG WAKISNMTFSNGKLIVNQDGFYYLYANICFRH HETSGDLATEYLQLMVYVTKTSIKIPSSHTLM KGGSTKYWSGNSEFHFYSINVGGFFKLRSGEEI SIEVSNPSLLDPDQDATYFGAFKVRDID |
| RANKL | 140-317 | 66 | IRAEKAMVDGSWLDLAKRSKLEAQPFAHLTIN ATDIPSGSHKVSLSSWYHDRGWAKISNMTFSN GKLIVNQDGFYYLYANICFRHHETSGDLATEY LQLMVYVTKTSIKIPSSHTLMKGGSTKYWSGN SEFHFYSINVGGFFKLRSGEEISIEVSNPSLLDP DQDATYFGAFKVRDID |

TABLE 1-continued

Possible components A

| Name: | AA Position | SEQ ID NO: | Sequence |
|---|---|---|---|
| TWEAK | 94-249 | 67 | SAPKGRKTRARRAIAAHYEVHPRPGQDGAQA GVDGTVSGWEEARINSSSPLRYNRQIGEFIVTR AGLYYLYCQVHFDEGKAVYLKLDLLVDGVL ALRCLEEFSATAASSLGPQLRLCQVSGLLALRP GSSLRIRTLPWAHLKAAPFLTYFGLFQVH |
| TWEAK | 105-249 | 68 | RAIAAHYEVHPRPGQDGAQAGVDGTVSGWEE ARINSSSPLRYNRQIGEFIVTRAGLYYLYCQVH FDEGKAVYLKLDLLVDGVLALRCLEEFSATA ASSLGPQLRLCQVSGLLALRPGSSLRIRTLPWA HLKAAPFLTYFGLFQVH |
| LIGHT | 83-240 | 69 | LIQERRSHEVNPAAHLTGANSSLTGSGGPLLW ETQLGLAFLRGLSYHDGALVVTKAGYYYIYS KVQLGGVGCPLGLASTITHGLYKRTPRYPEEL ELLVSQQSPCGRATSSSRVWWDSSFLGGVVH LEAGEKVVVRVLDERLVRLRDGTRSYFGAFM V |
| CD27L | 51-193 | 70 | ESLGWDVAELQLNHTGPQQDPRLYWQGGPA LGRSFLHGPELDKGQLRIHRDGIYMVHIQVTL AICSSTTASRHHPTTLAVGICSPASRSISLLRLSF HQGCTIASQRLTPLARGDTLCTNLTGTLLPSRN TDETFFGVQWVRP |
| CD27L | 56-193 | 71 | DVAELQLNHTGPQQDPRLYWQGGPALGRSFL HGPELDKGQLRIHRDGIYMVHIQVTLAICSSTT ASRHHPTTLAVGICSPASRSISLLRLSFHQGCTI ASQRLTPLARGDTLCTNLTGTLLPSRNTDETFF GVQWVRP |
| 4-1BBL | 85-254 | 72 | LDLRQGMFAQLVAQNVLLIDGPLSWYSDPGL AGVSLTGGLSYKEDTKELVVAKAGVYYVFFQ LELRRVVAGEGSGSVSLALHLQPLRSAAGAA ALALTVDLPPASSEARNSAFGFQGRLLHLSAG QRLGVHLHTEARARHAWQLTQGATVLGLFR VTPEIPAGLPSPRSE |
| GITRL | 50-177 | 73 | QLETAKEPCMAKFGPLPSKWQMASSEPPCVN KVSDWKLEILQNGLYLIYGQVAPNANYNDVA PFEVRLYKNKDMIQTLTNKSKIQNVGGTYELH VGDTIDLIFNSEHQVLKNNTYWGIILLANPQFI S |
| APRIL | 112-250 | 74 | KKQHSVLHLVPINATSKDDSDVTEVMWQPAL RRGRGLQAQGYGVRIQDAGVYLLYSQVLFQD VTFTMGQVVSREGQGRQETLFRCIRSMPSHPD RAYNSCYSAGVFHLHQGDILSVIIPRARAKLNL SPHGTFLGFVKL |
| EDA-1 | 245-391 | 75 | ENQPAVVHLQGQGSAIQVKNDLSGGVLNDWS RITMNPKVFKLHPRSGELEVLVDGTYFIYSQV EVYYINFTDFASYEVVVDEKPFLQCTRSIETGK TNYNTCYTAGVCLLKARQKIAVKMVHADISI NMSKHTTFFGAIRLGEAPAS |
| EDA-2 | 245-389 | 76 | ENQPAVVHLQGQGSAIQVKNDLSGGVLNDWS RITMNPKVFKLHPRSGELEVLVDGTYFIYSQV YYINFTDFASYEVVVDEKPFLQCTRSIETGKTN YNTCYTAGVCLLKARQKIAVKMVHADISINM SKHTTFFGAIRLGEAPAS |
| VEGI | 72-251 | 77 | LKGQEFAPSHQQVYAPLRADGDKPRAHLTVV RQTPTQHFKNQFPALHWEHELGLAFTKNRMN YTNKFLLIPESGDYFIYSQVTFRGMTSECSEIRQ AGRPNKPDSITVVITKVTDSYPEPTQLLMGTKS VCEVGSNWFQPIYLGAMFSLQEGDKLMVNVS DISLVDYTKEDKTFFGAFLL |
| VEGI | 93-251 | 78 | DKPRAHLTVVRQTPTQHFKNQFPALHWEHEL GLAFTKNRMNYTNKFLLIPESGDYFIYSQVTFR GMTSECSEIRQAGRPNKPDSITVVITKVTDSYP EPTQLLMGTKSVCEVGSNWFQPIYLGAMFSLQ EGDKLMVNVSDISLVDYTKEDKTFFGAFLL |

TABLE 1-continued

Possible components A

| Name: | AA Position | SEQ ID NO: | Sequence |
|---|---|---|---|
| BAFF | 134-285 | 79 | AVQGPEETVTQDCLQLIADSETPTIQKGSYTFV PWLLSFKRGSALEEKENKILVKETGYFFIYGQ VLYTDKTYAMGHLIQRKKVHVFGDELSLVTL FRCIQNMPETLPNNSCYSAGIAKLEEGDELQL AIPRENAQISLDGDVTFFGALKLL |

TNF-ligand family members interact with their cognate receptors, e.g. TNF with TNFR1 and TNFR2, TRAIL with TRAILR1 (DR4), TRAILR2 (DR5), TRAILR3 (DcR1), TRAILR4 (DcR2) and OPG, etc. The ligands mediate oligomerization and activation of their respective receptors. The interaction of members of the TNF receptor family with its ligands is characterized by binding of the receptors at the space between two of the three TNF-ligand family member protein monomers of the TNF-ligand family member protein homotrimer, the biological active form of TNF and other members of the TNF-ligand family.

Accordingly, the TNFR is selected from the group consisting of tumour necrosis factor receptor 1 (1A), tumor necrosis factor receptor 2 (1B), lymphotoxin beta receptor (3), OX40 (4), CD40 (5), Fas receptor (6), decoy receptor 3 (6B), CD27 (7), CD30 (8), 4-1BB (9), death receptor 4 (10A), death receptor 5 (10B), decoy receptor 1 (10C), decoy receptor 2 (10D), RANK (11A), osteoprotegerin (11B), TWEAK receptor (12A), TACI (13B), BAFF receptor (13C), herpesvirus entry mediator (14), nerve growth factor receptor (16), B-cell maturation antigen (17), glucocorticoid-induced TNFR-related (18), TROY (19), death receptor 6 (21), death receptor 3 (25), ectodysplasin A2 receptor (27). Preferably, the TNFR is TNFR2.

Regarding the suitability of TNFR2 as a therapeutic target, regulatory T cells (Tregs) are a subset of T-lymphocytes that modulate the immune system, maintain tolerance to self-antigens and abrogate autoimmune disease, by suppression or downregulation of effector T cell induction and proliferation. Enhancing suppressive activity of Tregs is thought to have diverse clinical applications in transplantation, allergy, asthma, infectious diseases, graft versus host disease (GvHD) and autoimmunity.

Tregs express high levels of TNFR2 and the expression of TNFR2 defines a unique subtype of Tregs with highly potent suppressive activity. Whereas TNFR2 seems not to be necessary to maintain Treg activity, recent results suggest that TNFR2 mediates the activation of Tregs and plays a functional role in their expansion and stabilization.

Next to its immune regulatory role, TNFR2 critically contributes to neuronal survival and regeneration. In contrast to TNFR1, which promotes neuronal tissue destruction, TNFR2 was protective in a mouse model of retinal ischemia via activation of the PKB/Akt pathway. Mechanistically, it was shown that TNF can protect primary cortical neurons from TNFR1 knockout mice against glutamate-induced excitotoxicity, whereas neurons from TNFR2 knockout mice are not protected. Similar results were observed in the cuprizone-induced mouse model of demyelination and remyelination, where genomic ablation of TNF resulted in delayed remyelination and a reduction in the pool of proliferating oligodendrocyte progenitors followed by a reduced number of mature oligodendrocytes. Analysis of TNFR1$^{-/-}$ and TNFR2$^{-/-}$ mice indicated that TNFR2 is critical for TNF-mediated oligodendrocyte regeneration, demonstrating that tissue regeneration is dependent on the signaling of TNF via TNFR2. Further in vitro studies have revealed that dopaminergic neurons were protected from $H_2O_2$ or 6-OHDA induced cell death by selective activation of TNFR2 after the toxic insult.

In addition, TNFR2 activation in oligodendrocyte progenitor cells (OPCs) enhanced the expression of anti-apoptotic and anti-oxidative proteins such as BCL-2 and SOD2, which may stabilize the mitochondrial membrane and thus might contribute to the observed TNFR2-mediated protection of OPCs against $H_2O_2$-induced cell death. TNFR2 activation also promotes the release of anti-inflammatory and neurotrophic factors from astrocytes which can promote oligodendrocyte differentiation and may thus support remyelination. Summarizing, TNFR2 is involved in immune regulation, e.g. via expansion of Tregs, and tissue protection and regeneration.

Soluble and transmembrane TNF, the former naturally derived through TACE mediated proteolytic cleavage of the extracellular domain of the latter, tmTNF, differ in their capability to stimulate signaling via TNFR1 and TNFR2. Binding of either sTNF or tmTNF can activate TNFR1, whereas TNFR2 is only fully activated by tmTNF. Whereas sTNF shows a remarkably high affinity for TNFR1 (KD=$1.9 \cdot 10^{-11}$ M), the affinity for TNFR2 is significantly lower (KD=$4.2 \cdot 10^{-10}$ M). It was proposed that the high affinity for TNFR1 is mainly caused by stabilization of the ligand/receptor complexes, while transient binding of sTNF to TNFR2 results in short-lived complexes which may be inefficient to induce intracellular signaling. Concluding, efficient activation of TNFR2 requires stable receptor complex formation by the membrane form of TNF. The activation of TNFR2 by tmTNF can be mimicked by e.g. oligomerized soluble forms of tmTNF.

Mutations in the TNF sequence can lead to a loss of binding/affinity to TNFR1 thereby leading to selectivity for TNFR2. Preferably, TNF has a sequence based on SEQ ID NO: 43, which further comprises one or more $TNF_{R2}$ specific mutations selected from the group consisting of D143Y, D143F, D143E, D143N, E146Q, E146H, E146K, A145R/S147T, Q88N/T89S/A145S/E146A/S147D, Q88N/A145I/E146G/S147D, A145H/E146S/S147D, A145H/S147D, L29V/A145D/E146D/S147D, A145N/E146D/S147D, A145T/E146S/S147D, A145Q/E146D/S147D, A145T/E146D/S147D, A145D/E146G/S147D, A145D/S147D, A145K/E146D/S147T, A145R/E146T/S147D, A145R/S147T, E146D/S147D, E146N/5147, K65W, D143N, D143E, D143F, D143W, D143Y, D143V, D143V/F144L/A145S, D143N/A145R, D143V/A145S, A145R, A145H, A145K, A145F, and A145W.

Preferably, TNF has a sequence according to SEQ ID NO: 80, which is based on SEQ ID NO: 43, and comprises the TNFR2 specific mutation D143N/A145R.

Preferably, a PLG according to the present invention comprises three TNF protein ligands according to SEQ ID NO: 80. Preferably, the three TNF protein ligands are covalently fused via a peptide linker, preferably via a peptide linker according to SEQ ID NO: 15. Preferably, a PLG according to the present invention has SEQ ID NO: 81

Preferably, in the TNFR binding protein complex of the present invention, the C-terminus of the first THD, respectively, which is defined by the C-terminal consensus sequence $$-S/T/V-F/Y/S-F-G-A/L/V/I-X_1, \quad \text{(SEQ ID NO: 1)}$$

is linked to the N-terminus of the second THD, which is defined by the N-terminal consensus sequence $$X_2-V/A/F-A-H-V/L/I/Y \quad \text{(SEQ ID NO: 2)}$$

or $$X_3-V/W/F/C-A/L-E/Y/Q/H-L, \quad \text{(SEQ ID NO: 3)}$$

by L1, which has a length of 2 to 20 amino acids, preferably 2 to 15 amino acids, more preferably 3 to 10 amino acids and most preferably of 3 to 5 amino acids;

wherein $X_1$ is a non-polar/hydrophob or polar/neutral amino acid, preferably selected from the group consisting of F, V, Q, A, I, L, and Y;

wherein $X_2$ is selected from the group consisting of P, K, V, I, and A; and wherein $X_3$ is selected from the group consisting of D, S, M, and I optionally further comprising one to four further THDs each consecutively linked to each other in the same way as the first and second THD.

The peptidomimetic is selected from the group consisting of (lipoprotein-associated coagulation inhibitor (LACI-D1); affilins, selected from human-γ B crystalline or human ubiquitin; cystatin; Sac7D from *Sulfolobus acidocaldarius*; lipocalin and anticalins derived from lipocalins; designed ankyrin repeat domains (DARPins); SH3 domain of Fyn; Kunits domain of protease inhibitors; monobodies selected from the $10^{th}$ type III domain of fibronectin; adnectins; cysteine knot miniproteins; atrimers; evibodies, selected from CTLA4-based binders, affibodies, selected from three-helix bundle from Z-domain of protein A from *Staphylococcus aureus*; trans-bodies, selected from human transferrin; tetranectins, selected from monomeric or trimeric human C-type lectin domain; microbodies, selected from trypsin-inhibitor-II; affilins; armadillo repeat proteins.

It is further preferred that the immunoglobulin Fc region dimerization domain is the human immunoglobulin Fc region dimerization domain, which has the SEQ ID NO: 82, or that the immunoglobulin Fc region dimerization domain is the human Fc mutant (Δab; E233P, L234V, L235A, ΔG236, A327G, A330S, P331S) with abolished ADCC/CDC functionality, which has the SEQ ID NO: 83. It is further preferred that the p53 dimerization domain is the human p53 dimerization domain, which has the SEQ ID NO: 84. It is further preferred that the GCN4 tetramerization domain is the yeast GCN4 tetramerization domain, which has the SEQ ID NO: 85. It is further preferred that the VASP tetramerization domain is the human ena/VASP (enabled/vasodilator-stimulated phosphoprotein), which has the SEQ ID NO: 86.

Particularly preferred complexes of the present invention are complexes comprising or consisting of subunits selected from the sequences SEQ ID NO: 87 to 90, wherein the PL is human TNF.

In a preferred embodiment, the TNFR binding protein complex of the present invention comprises or consists of two subunits of SEQ ID NO: 87 (scTNF$_{R2}$-Fc-scTNF$_{R2}$). The dimerization of the two subunits results in a dodecavalent TNF complex characterized by four trivalent TNF$_{R2}$ PLGs and two Fc dimerization domains, wherein two PLGs are fused to the N-terminus of each dimerization domain via linker L3 and two PLGs are fused to the C-terminus of each dimerization domain via linker L4.

In another preferred embodiment, the TNFR binding protein complex of the present invention comprises or consists of four subunits of SEQ ID NO: 88 (p53-scTNF$_{R2}$). The tetramerization of the four subunits results in a dodecavalent TNF complex characterized by four trivalent TNF$_{R2}$ PLGs and four p53 tetramerization domains, wherein each PLG is fused to the C-terminus of the tetramerization domain via linker L3.

In a further preferred embodiment, TNFR binding protein complex comprises or consists of four subunits of SEQ ID NO: 89 (GCN4-scTNF$_{R2}$). The tetramerization of the four subunits results in a dodecavalent TNF complex characterized by four trivalent TNF$_{R2}$ PLGs and four GCN4 tetramerization domains, wherein each PLG is fused to the C-terminus of the tetramerization domain via linker L3.

In an additional preferred embodiment, is a TNFR binding protein complex comprises or consists of four subunits of SEQ ID NO: 90 (VASP-scTNF$_{R2}$). The tetramerization of the four subunits results in a dodecavalent TNF complex characterized by four trivalent TNF$_{R2}$ PLGs and four VASP tetramerization domains, wherein each PLG is fused to the C-terminus of the tetramerization domain via linker L3.

Also conceivable are TNFR binding protein complexes comprising or consisting of subunits of SEQ ID NO 91 (p53-sc-mTNF$_{R2}$) or comprising or consisting of subunits of SEQ ID NO: 92 (GCN4-sc-mTNF$_{R2}$), wherein the PL is mouse TNF.

The inventors surprisingly found out that the complexes of the present invention show an up to tenfold improved activity e.g. compared to a hexavalent complex. Of these, a complex of four subunits, which are comprised of GCN4 and scTNF$_{R2}$, is particularly potent.

In a second aspect the present invention provides a nucleic acid encoding the polypeptides according to the first and second aspect of the present invention. The nucleic acid may be RNA or DNA or a hybrid thereof. Preferably, the nucleic acid also comprises sequences allowing for the expression of the polypeptide according the first aspect of the present invention in a suitable expression system. The nucleic acid can be codon optimized for the respective expression system.

In a third aspect, the present invention provides a vector comprising the nucleic acid of the second aspect of the present invention. It is preferred that the genes of interest encoded by the introduced polynucleotide are expressed within the cell upon introduction of the vector or vectors. Preferably, the vector provides for transcription and expression of the polypeptide encoded by the nucleic acid in a suitable host cell system. Preferably, the expression vector is selected from the group consisting of a bacterial, yeast, baculovirus, plant and mammalian expression vector, more preferably the expression vector is a bacterial expression vector or a cell-free expression vector.

In a fourth aspect the present invention provides the polypeptide of the first aspect, the nucleic acid of the second aspect or the vector of the third aspect for use as a medicament.

In a fifth aspect, the present invention provides a pharmaceutical composition comprising the complex of the first aspect of the present invention, or the nucleic acid of the second aspect, or the vector of the fourth aspect. The pharmaceutical composition preferably further comprises pharmaceutical acceptable carriers and/or suitable excipients. The pharmaceutical composition is selected from the group consisting of solid, liquid, semi-solid or transdermal therapeutic systems. It is envisioned that the pharmaceutical compositions of the invention comprise one or more complexes of the first aspect of the invention.

In a sixth aspect, the present invention relates to a polypeptide of the first or the second aspect, a nucleic acid of the third aspect or a vector of the fourth aspect or a pharmaceutical composition of the fifth aspect for use in the diagnosis, prophylaxis or treatment of hyperproliferative disorders or inflammatory disorders, preferably cancer or malignancies of the hematologic system, autoimmune disorders and degenerative diseases, preferably neurodegenerative diseases.

Preferred hyperproliferative diseases are selected from the group consisting of precancerosis; dysplasia; metaplasia; cancer; and skin diseases.

Particular preferred cancers to be treated by the polypeptides of the present invention are carcinomas of the gastrointestinal tract, liver, kidney, bladder, prostate, endometrium, ovary, testes, skin, invasive oral cancers, small cell and non-small cell lung carcinomas, hormone-dependent breast cancers, hormone-independent breast cancers, transitional and squamous cell cancers, neurological malignancies including neuroblastoma, gliomas, astrocytomas, osteosarcomas, soft tissue sarcomas, hemangioamas, endocrinological tumors, hematologic neoplasias including leukemias, lymphomas, and other myeloproliferative and lymphoproliferative diseases, carcinomas in situ, hyperplastic lesions, adenomas, fibromas, histiocytosis, chronic inflammatory proliferative diseases, vascular proliferative diseases and virus-induced proliferative diseases, skin diseases characterized by hyperproliferation of keratinocytes and/or T cells. Particular preferred diseases treatable with the compounds of the present invention are solid tumors, in particular lung, breast, pancreas, colorectal, ovarian, prostatic and gastric cancers and adenocarcinomas.

The precancerosis treatable with the polypeptides of the present invention are preferably selected from the group consisting of precancerosis of the skin, in particular actinic keratosis, cutaneaous horn, actinic cheilitis, tar keratosis, arsenic keratosis, x-ray keratosis, Bowen's disease, bowenoid papulosis, lentigo maligna, lichen sclerosus, and lichen rubber mucosae; precancerosis of the digestive tract, in particular erythroplakia, leukoplakia, Barrett's esophagus, Plummer-Vinson syndrome, crural ulcer, gastropathia hypertrophica gigantea, borderline carcinoma, neoplastic intestinal polyp, rectal polyp, porcelain gallbladder; gynaecological precancerosis, in particular carcinoma ductale in situ (CDIS), cervical intraepithelial neoplasia (CIN), leukoplakia, endometrial hyperplasia (grade III), vulvar dystrophy, vulvar intraepithelial neoplasia (VIN), hydatidiform mole; urologic precancerosis, in particular bladder papillomatosis, Queyrat's erythroplasia, testicular intraepithelial neoplasia (TIN), leukoplakia; carcinoma in situ (CIS); precancerosis caused by chronic inflammation, in particular pyoderma, osteomyelitis, acne conglobata, lupus vulgaris, and fistula.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exist chronic irritation or inflammation. Dysplastic disorders which can be treated with the compounds of the present invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis heminelia, dysplasia epiphysialis multiplex, dysplasia epiphysalis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia hidrotic ectodermal dysplasia, hypohidrotic ectodermal dysplasia, lymphopenic thymic dysplasia, mammary dysplasia, mandibulofacial dysplasia, metaphysical dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Metaplasia is a form of controlled cell growth in which one type of adult or fully differentiated cell substitutes for another type of adult cell. Metaplastic disorders, which are treatable are preferably selected from the group consisting of agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, symptomatic myeloid metaplasia and regenerative metaplasia.

Many skin diseases are characterized by hyperproliferation of keratinocytes and/or T cells. Examples of such diseases which are treatable with the compounds of the present invention comprise without limitations psoriasis in particular psoriasis vulgaris, psoriasis capitis, psoriasis guttata, psoriasis inversa; neurodermatitis; ichtyosises; alopecia areata; alopecia totalis; alopecia subtotalis; alopecia universalis; alopecia diffusa; atopic dermatitis; lupus erythematodes of the skin; dermatomyositis of the skin; atopic eczema; morphea; scleroderma; alopecia areata Ophiasis type; androgenic alopecia; allergic contact dermatitis; irritative contact dermatitis; contact dermatitis; pemphigus vulgaris; pemphigus foliaceus; pemphigus vegetans; scarring mucous membrane pemphigoid; bullous pemphigoid; mucous membrane pemphigoid; dermatitis; dermatitis herpetiformis Duhring; urticaria; necrobiosis lipoidica; erythema nodosum; prurigo simplex; prurigo nodularis; prurigo acuta; linear IgA dermatosis; polymorphic light dermatosis;

erythema solaris; exanthema of the skin; drug exanthema; purpura chronica progressiva; dihydrotic eczema; eczema; fixed drug exanthema; photoallergic skin reaction; and perioral dermatitis.

Inflammatory disorders that can be treated with the polypeptides of the invention include but are not limited to acute disseminated encephalomyelitis (ADEM), Addison's disease, agammaglobulinemia, alopecia areata, amyotrophic lateral sclerosis (also Lou Gehrig's disease; motor neuron disease), ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune pancreatitis, autoimmune peripheral neuropathy, autoimmune polyendocrine syndrome, Autoimmune progesterone dermatitis, Autoimmune thrombocytopenic purpura, autoimmune urticarial, Autoimmune uveitis, Balo disease/Balo concentric sclerosis, Behçet's disease, Berger's disease, Bickerstaffs encephalitis, Blau syndrome, bullous pemphigoid, cancer, Castleman's disease, celiac disease, Chagas disease, chronic inflammatory demyelinating polyneuropathy, chronic inflammatory demyelinating polyneuropathy, chronic obstructive pulmonary disease, chronic recurrent multifocal osteomyelitis, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, discoid lupus erythematosus, Dressler's syndrome, drug-induced lupus, eczema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressive, fibrosing alveolitis (or Idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Hashimoto's thyroiditis, Henoch-Schonlein purpura, herpes gestationis aka gestational pemphigoid, hidradenitis suppurativa, Hughes-Stovin syndrome, hypogammaglobulinemia, idiopathic inflammatory demyelinating diseases, idiopathic pulmonary fibrosis, idiopathic thrombocytopenic purpura (see autoimmune thrombocytopenic purpura), IgA nephropathy, inclusion body myositis, interstitial cystitis, juvenile idiopathic arthritis aka juvenile rheumatoid arthritis, Kawasaki's disease, Lambert-Eaton myasthenic syndrome, leukocytoclastic vasculitis, lichen planus, lichen sclerosus, linear IgA disease (LAD), lupoid hepatitis aka autoimmune hepatitis, lupus erythematosus, Majeed syndrome, microscopic colitis, microscopic polyangiitis, Miller-Fisher syndrome, mixed connective tissue disease, morphea, Mucha-Habermann disease aka pityriasis lichenoides et varioliformis acuta, multiple sclerosis, myasthenia gravis, myositis, Meniere's disease, narcolepsy, neuromyelitis optica (also Devic's disease), neuromyotonia, ocular cicatricial pemphigoid, opsoclonus, myoclonus syndrome, Ord's thyroiditis, palindromic rheumatism, PANDAS (pediatric autoimmune neuropsychiatric disorders associated with streptococcus), paraneoplastic cerebellar degeneration, paroxysmal nocturnal hemoglobinuria (PNH), Parry Romberg syndrome, pars planitis, Parsonage-Turner syndrome, pemphigus vulgaris, perivenous encephalomyelitis, pernicious anaemia, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pure red cell aplasia, pyoderma gangrenosum, Rasmussen's encephalitis, Raynaud phenomenon, Reiter's syndrome, relapsing polychondritis, restless leg syndrome, retroperitoneal fibrosis, rheumatic fever, rheumatoid arthritis, sarcoidosis, schizophrenia, Schmidt syndrome another form of APS, Schnitzler syndrome, scleritis, scleroderma, serum sickness, Sjögren's syndrome, spondyloarthropathy, stiff person syndrome, Still's disease see juvenile rheumatoid arthritis, subacute bacterial endocarditis (SBE), Susac's syndrome, Sweet's syndrome, Sydenham chorea, sympathetic ophthalmia, systemic lupus erythematosus see lupus erythematosus, Takayasu's arteritis, temporal arteritis (also known as "giant cell arteritis"), thrombocytopenia, Tolosa-Hunt syndrome, transverse myelitis, ulcerative colitis (one of two types of idiopathic inflammatory bowel disease "IBD"), undifferentiated connective tissue disease different from mixed connective tissue disease, undifferentiated spondyloarthropathy, urticarial vasculitis, vasculitis, vitiligo, and Wegener's granulomatosis.

Hypersensitvity includes but is not limited to allergy, such as asthma, anaphylaxis or atopy; cytotoxic-antibody-dependent diseases such as autoimmune hemolytic anemia, thrombocytopenia, rheumatic heart disease, erythroblastosis fetal, Goodpasture's syndrome, membranous nephropathy, Graves' disease, myasthenia gravis; immune complex diseases such as serum sickness, arthus reaction, rheumatoid arthritis, post-streptococcal glomerulonephritis, lupus nephritis, systemic lupus erythematosus, extrinsic allergic alveolitis (hypersensitivity pneumonitis), cell-mediated immune response such as contact dermatitis, Mantoux test, chronic transplant rejection, and multiple sclerosis.

Neurodegenerative disorders include Alzheimer's disease, progressive supranuclear palsy, corticobasal degeneration, tauopathy, Pick's disease, Parkinson's disease, neuropathy, dementia with Lewy bodies, multiple system atrophy, Huntington's disease, spinal and bulbar muscular atrophy, Friedreich's ataxia, spinocerebellar ataxia, Creutzfeldt-Jakob disease, Gerstmann-Sträussler-Scheinker syndrome, fatal familial insomnia, kuru, amyotrophic lateral sclerosis, spinal muscular atrophy, and Batten disease.

Infectious diseases that can be treated with the polypeptides of the invention include but are not limited to anaplasmosis, anthrax, babesiosis, botulism, brucellosis, glanders (*Burkholderia mallei*), melioidosis (*Burkholderia pseudomallei*), campylobacteriosis (*Campylobacter*), carbapenem-resistant Enterobacteriaceae infection, chancroid, chikungunya, chlamydia, ciguatera, *Clostridium difficile* infection, *Clostridium perfringens* infection, Coccidioidomycosis fungal infection (valley fever), Creutzfeldt-Jacob disease (transmissible spongioform), cryptosporidiosis, cyclosporiasis, dengue fever, diphtheria, *Escherichia coli* infection, Eastern equine encephalitis, Ebola hemorrhagic fever, ehrlichiosis, parainfectious or arboviral encephalitis, enterovirus infection, giardiasis, gonorrhea, granuloma inguinale, haemophilus influenza, hantavirus pulmonary syndrome, hemolytic uremic syndrome, hepatitis A, hepatitis B, hepatitis C, hepatitis D, hepatitis E, herpes, histoplasmosis, human immunodeficiency virus (HIV/AIDS), human papillomavirus, influenza, legionellosis, leprosy, leptospirosis, listerosis, Lyme disease, malaria, measles, viral meningitis, bacterial meningitis, Middle East respiratory syndrome coronavirus (MERS-CoV), mumps, norovirus, paralytic shellfish poisoning, pediculosis, pelvic inflammatory disease, pertussis, bubonic, septicemic, pneumonic plague, pneumococcal disease, polio, psittacosis, pthiriasis, smallpox, monkeypox, cowpox, Q-fever, rabies, rickettsiosis, rubella, salmonellosis gastroenteritis, scabies, scombroid, severe acute respiratory syndrome (SARS), shigellosis gastroenteritis, methicillin resistant staphylococcal infection (MRSA), syphilis, tetanus infection, trichinosis, tuberculosis, rabbit fever, typhoid fever, typhus, bacterial vaginosis, varicella, cholera, vibrosis, Lassa hemorrhagic fever, Marburg hemorrhagic fever, West Nile virus, yellow fever, and zika.

EXAMPLES

Example 1: Genetic Engineering of Complexes of the Present Invention

The tetramerization domains of human p53 (aa 320-359) (SEQ ID NO: 84) and yeast GCN4 (aa 249-281), specifically the mutant (M250L/L253I/L260I/L267I/L274I/V257L/V271L/V278L/N264L) (SEQ ID NO: 85), were fused to the N-terminal end of a human single-chain TNF variant (D143N/A145R, scTNF$_{R2}$) (SEQ ID NO: 81) or a mouse single-chain TNF variant (D221N/A223R, sc-mTNF$_{R2}$) (SEQ ID NO: 93). The TNF$_{R2}$-selective human TNF variant (scTNF$_{R2}$) and TNF$_{R2}$-selective mouse TNF variant (sc-mTNF$_{R2}$) are trivalent PLGs according to the present invention. The TNF domains of the human scTNF$_{R2}$ and mouse sc-mTNF$_{R2}$ are connected via a peptide linker L1 consisting of GGGGS (SEQ ID NO: 15). The trivalent human and mouse PLGs are connected via a peptide linker L3 consisting of GAPGGGSGGGSGGGSGGGSGGGSGGSEFLA (SEQ ID NO: 41) and GAPGGGSGGGSGGGSGGGSGGGSGGSGIR (SEQ ID NO: 40), respectively, to the tetramerization domains human p53 and yeast GCN4. The complexes based on these constructs (i.e. subunits) are denoted p53-scTNF$_{R2}$ and GCN4-scTNF$_{R2}$ (human) (SEQ ID NO: 88 and 89), and p53-sc-mTNF$_{R2}$ and GCN4-sc-mTNF$_{R2}$ (mouse) (SEQ ID NO: 91 and 92) (FIGS. 1 and 2).

For comparison, the dimerization domain (CH2) of EHD2 from IgE (SEQ ID NO: 94) was fused to the N-terminal end of the trivalent human single-chain scTNF$_{R2}$ variant (D143N/A145R, scTNF$_{R2}$) (SEQ ID NO: 81) and the trivalent mouse single-chain sc-mTNF$_{R2}$ variant (D221N/A223R, sc-mTNF$_{R2}$) (SEQ ID NO: 93), respectively. The dimerization domains are connected to trivalent scTNF$_{R2}$ and sc-mTNF$_{R2}$ via a peptide linker L3 consisting of GGGSGGGSGGGSGGGSGGGSGGSEFLA (SEQ ID NO: 95) and GGGSGGGSGGGSGGGSGGGSGGSGIR (SEQ ID NO: 96), respectively. The TNF domains of the human scTNF$_{R2}$ and mouse sc-mTNF$_{R2}$ are connected via a peptide linker L1 consisting of GGGGS (SEQ ID NO: 15). These complexes are denoted EHD2-scTNF$_{R2}$ (human) (SEQ ID NO: 97) and EHD2-sc-mTNF$_{R2}$ (mouse) (SEQ ID NO: 98) (FIGS. 1 and 2).

For further comparison, human scTNF$_{R2}$ and mouse sc-mTNF$_{R2}$ were used, which are trimeric PLGs of the present invention. The TNF domains of the human scTNF$_{R2}$ (SEQ ID NO: 81) and mouse sc-mTNF$_{R2}$ (SEQ ID NO: 93) are connected via a peptide linker L1 consisting of GGGGS (SEQ ID NO: 15).

The overall codon usage of the constructs was adapted for expression in mammalian cells.

To facilitate purification, an N-terminal His-tag was introduced in all constructs.

Example 2: Production and Purification of Complexes of the Present Invention

HEK293-6E cells, grown in F17 medium (Life Technologies, Darmstadt, Germany), were transiently transfected with the DNA constructs according to Example 1 using polyethyleneimine (Sigma). The day after, Tryptone N1 (Organotechnie, TekniScience, Terrebonne, Canada) was added to the cell culture and cells were cultivated for additional 4 days. Then, supernatant was collected and recombinant proteins were isolated therefrom.

Supernatant was loaded onto a column comprising Ni-NTA agarose (Macherey-Nagel, Düren, Germany) and purified via immobilized metal ion chromatography (IMAC) and unbound proteins were removed using IMAC wash buffer (50 mM sodium phosphate buffer, pH 7.5). Bound proteins were eluted with IMAC elution buffer (50 mM sodium phosphate buffer, 250 mM imidazole, pH 7.5) and dialyzed (membrane cut-off 4-6 kDa, Roth, Karlsruhe, Germany) against PBS buffer (pH 7.4) overnight at 4° C. Dialyzed proteins were further purified by size exclusion chromatography. To this, the proteins were loaded on Superdex 200 10/300 GL or HiLoad 26/600 Superdex 200 pg gel filtration columns (GE Healthcare, Freiburg, Germany) using an AKTA FPLC device (GE Healthcare) (and eluted with PBS, pH 7.4).

Protein concentration was determined by measuring the absorbance at 280 nm.

For Coomassie staining, 2 µg of the purified proteins according to Example 1 were denatured in Laemmli buffer (50 mM TRIS pH 6.8, 4M urea, 1% SDS, 15% glycerol, 0.01% bromphenol blue, 5% 2-mercaptoethanol) under reducing conditions (in the presence of mercaptoethanol, +2-ME) and non-reducing conditions (in the absence of mercaptoethanol, −2-ME) and resolved by 8% SDS-PAGE (100V; 90 minutes). The SDS-PAGE gels were incubated in Coomassie staining solution (40% methanol, 10% acetic acid, 0.1% Coomassie brilliant blue) for 60 minutes at RT and destained using Coomassie destain solution (40% methanol, 10% acetic acic) (FIGS. 3A and 3C). Alternatively, InstantBlue stain (Expedion) was used for staining of proteins in SDS-PAGE gels (FIGS. 3B and 3C).

For immunoblot analysis, 1 µg protein was denatured in Laemmli buffer under reducing conditions (+2-ME) and non-reducing conditions (−2-ME) and resolved by 8% SDS-PAGE (100V; 90 minutes). Proteins were transferred from the SDS-PAGE gel onto nitrocellulose membranes (semidry blot; 1.5 mA/cm$^2$ gel for 90 minutes) and non-specific protein binding was blocked with 5% skimmed milk powder solution in PBS/0.1% Tween 20 for 30 minutes at room temperature (RT) after which the membrane was incubated overnight at 4° C. using specific antibodies. Following an incubation with HRP-conjugated secondary antibodies for 90 minutes at room temperature, the signals were detected by enhanced chemiluminescence (Super Signal, Pierce, Rockford, Ill., USA) (FIGS. 3B and 3D).

Under reducing conditions the TNF variants exhibited an apparent molecular mass that matches with the calculated molecular mass (Table 2).

TABLE 2

Calculated molecular mass of TNFR-binding protein complexes

|  | scTNF$_{R2}$ | EHD2-scTNF$_{R2}$ | p53-scTNF$_{R2}$ | GCN4-scTNF$_{R2}$ |
|---|---|---|---|---|
| MW [kDa] | 51.9 | 136.7 | 245.8 | 242.8 |

|  | sc-mTNF$_{R2}$ | EHD2-sc-mTNF$_{R2}$ | p53-sc-mTNF$_{R2}$ | GCN4-sc-mTNF$_{R2}$ |
|---|---|---|---|---|
| MW [kDa] | 50.2 | 133.1 | 238.6 | 235.6 |

Example 3: Purity of Oligomerized Complexes of the Present Invention

The purity and oligomerization state of the protein complexes according to Example 1 was further characterized by HPLC size exclusion chromatography Approx. 20 μg protein was applied together with standard proteins to a BioSep-SEC-S2000 7.8×300 mm column (Phenomenex, Aschaffenburg, Germany) or a SuperSW mAb HR, 7.8×300 mm column (Tosoh Bioscience, Griesheim, Germany) equilibrated with PBS buffer and eluted at a flow rate of 0.5 ml/min. scTNF$_{R2}$ and the complexes eluted at the expected size as a single major peak indicating the integrity and high purity of the proteins (FIG. 4).

Example 4: Selective Binding of the Complexes of the Present Invention to Immobilized TNF Receptors Affinity of recombinant mouse and human TNF (rmTNF and rhTNF, Immunotools) and the protein complexes according to Example 2 to TNFRs was analyzed by binding studies with immobilized TNFR1-Fc and TNFR2-Fc fusion proteins.

ELISA plates (Greiner, Frickenhausen, Germany) were coated with huTNFR1-Fc, mTNFR1-Fc, huTNFR2-Fc or mTNFR2-Fc fusion proteins at 1 μg/ml in PBS and incubated at 4° C. overnight. Residual binding sites were blocked with 2% skim milk powder in PBS at RT for 2 hours. ScTNF$_{R2}$ and the complexes were diluted in 2% skim milk powder in PBS and added at concentrations in the range of $10^{-3}$ to 10 nM and incubated for 1 hour at RT. Between each step, non-bound proteins were removed by washing 4 times with 0.005% Tween-20 in PBS.

Bound proteins were detected with mouse monoclonal antibodies to TNF (clone F6C5; 1 μg/ml; incubation for 1 hour at RT) and HRP-conjugated anti-mouse IgG antibodies (diluted 1:10000; incubation for 1 hour at RT), followed by incubation with tetramethylbenzidine (TMB) substrate solution. Reaction was stopped by addition of 1 M $H_2SO_4$ and the absorbance at 450 nm was determined with a Multiskan FC absorbance reader (Thermo Scientific, Karlsruhe, Germany) and data were analyzed using the software Microsoft Excel and GraphPad Prism 4 (GraphPad, La Jolla, Calif.) (FIG. 5). In Table 3, the calculated $EC_{50}$ values for the binding of TNF, scTNF$_{R2}$ and the complexes to immobilized huTNFR2 and mTNFR2 based on the ELISA assay are summarized.

TABLE 3

$EC_{50}$ values (nM) for binding of TNFR-binding protein complexes to huTNFR2 and mTNFR2

| huTNFR2 | | | |
|---|---|---|---|
| scTNF$_{R2}$ | EHD2-scTNF$_{R2}$ | p53-scTNF$_{R2}$ | GCN4-scTNF$_{R2}$ |
| 0.5539 | 0.5084 | 0.0940 | 0.0312 |

| mTNFR2 | | | |
|---|---|---|---|
| sc-mTNF$_{R2}$ | EHD2-sc-mTNF$_{R2}$ | p53-sc-mTNF$_{R2}$ | GCN4-sc-mTNF$_{R2}$ |
| 1.553 | 0.1116 | 0.0744 | 0.04515 |

Clearly, the dodecavalent complexes of the present invention showed a superior binding to both huTNFR2 and mTNFR2 relative to the trivalent and hexavalent proteins (up to >10-fold). Of the complexes of the invention, GCN4-scTNF$_{R2}$ and GCN4-sc-mTNF$_{R2}$ display the most favorable $EC_{50}$ values.

Affinities of scTNF$_{R2}$ and the complexes for human TNFR2-Fc were further determined by quartz crystal microbalance measurements using an Attana Cell 200 (Attana, Stockholm, Sweden). Human TNFR2-Fc was chemically immobilized on a carboxyl sensor chip according to the manufacturer's protocol at a high and low density, respectively. Binding experiments were performed in PBST buffer (PBS, 0.1% Tween 20, pH 7.4) with a flow rate of 25 ml/min at 37° C. The chip was regenerated with 10 mM Glycine-HCl, pH 2.0. Before each measurement, a baseline was measured which was subtracted from the binding curve. Data were collected using the software provided by Attana for the particular device and analyzed by Attaché Office Evaluation software (Attana, Stockholm, Sweden) and TraceDrawer (Ridgview Instruments, Vange, Sweden) (FIG. 6). In Table 4, binding values for the binding of the hexavalent and dodecavalent mouse complexes to TNFR2 are summarized, which have been calculated based on quartz crystal microbalance measurements on a low density chip. In Table 5, binding values for the binding of the sc-mTNF$_{R2}$ and the hexavalent and dodecavalent mouse proteins to TNFR2 are summarized, which have been calculated based on quartz crystal microbalance measurements on a high density chip.

TABLE 4

Binding of TNFR-binding protein complexes to TNFR2 on a low density chip (130 Hz)

| Protein | EHD2-sc-mTNF$_{R2}$ | p53-sc-mTNF$_{R2}$ | GCN4-sc-mTNF$_{R2}$ | sc-mTNF$_{R2}$ |
|---|---|---|---|---|
| $k_{on}$ [$M^{-1}s^{-1}$] | $5.33 \times 10^5$ | $1.28 \times 10^6$ | $2.16 \times 10^6$ | n/d |
| $K_{off}$ [$s^{-1}$] | $6.3 \times 10^{-2}$ | $6.51 \times 10^{-2}$ | $3.47 \times 10^{-2}$ | n/d |
| $K_d$ (nM) | 118 | 50.9 | 16.1 | n/d |

TABLE 5

Binding of TNFR-binding protein complexes to TNFR2 on a high density chip (270 Hz)

| Protein | EHD2-sc-mTNF$_{R2}$ | p53-sc-mTNF$_{R2}$ | GCN4-sc-mTNF$_{R2}$ | sc-mTNF$_{R2}$ |
|---|---|---|---|---|
| $K_{on}$ (M$^{-1}$s$^{-1}$) | 6.07 × 10$^5$ | 6.16 × 10$^5$ | 1.67 × 10$^6$ | 8.08 × 10$^5$ |
| $K_{off}$ (s-1) | 3.74 × 10$^{-5}$ | 2.69 × 10$^{-5}$ | 8.77 × 10$^{-5}$ | 3.99 × 10$^{-4}$ |
| $K_d$ (nM) | 0.0615 | 0.0437 | 0.0527 | 0.4494 |

At high receptor density, both hexavalent and dodecavalent scTNF$_{R2}$ displayed apparent ~10 fold increased affinities for TNFR2, compared to a trivalent scTNF$_{R2}$. Clear differences in the apparent affinity of the various proteins were revealed with a low density chip, with p53-sc-mTNF$_{R2}$ and, in particular GCN4-sc-mTNF$_{R2}$ showing higher apparent affinities for TNFR2 as compared to both, trivalent (sc-mTNF$_{R2}$) and hexavalent (EHD2-sc-mTNF$_{R2}$) scTNF$_{R2}$ variants. (Table 4). In contrast, no binding to TNFR1 was observed at any concentration tested (data not shown).

Example 5: Lack of Activation of TNFR1 by the Complexes of the Present Invention The selectivity of protein complexes was determined using HeLa and L929 cells. Upon an activation of TNFR1, e.g. with recombinant mouse rmTNF, cells secrete interleukin 6 (IL-6). Consequently, the supernatant of the cells incubated with rmTNF or various complexes was analyzed for the presence of IL-6 using ELISA.

L929 cells (1.5×10$^4$ cells/well) were grown in 96-well flat bottom cell culture plates overnight. L929 cells were treated with actinomycin D (1 µg/ml) for 30 minutes prior to addition of rmTNF or the mouse complexes of Example 1. Then cells were incubated with different protein concentrations for 24 hours at 37° C. Cells were washed with PBS and incubated with crystal violet (20% methanol, 0.5% crystal violet) for 20 minutes to stain viable cells. The dye was removed under rinsing water and cells were air-dried. Crystal violet was resolved with methanol and the optical density was determined at 550 nm. Each sample was analyzed in triplicates and data were analyzed using the software Microsoft Excel and GraphPad Prism 4 (GraphPad, La Jolla, Calif.) (FIG. 7A).

HeLa cells (2.0×10$^4$ cells/well) were stimulated as indicated for the L929 cells above and supernatants were collected after 24 h incubation and analyzed by an ELISA specific for IL-6 according to the instructions of the manufacturer (Biolegend, San Diego, Calif., USA). The absorbance at 450 nm was determined and the amount of released IL-6 was determined with the provided standard and calculated using the software GraphPad Prism 4 (FIG. 7B).

In contrast to rmTNF, none of the tested protein complexes activated TNFR1-dependent cell death in L929, verifying that the affinity for TNFR1 was lost due to the mutations D221N/A223R. Further, in contrast to rmTNF, none of the tested protein complexes induced IL-6 secretion in HeLa cells, which also shows that the complexes tested did not have an affinity for TNFR1.

Example 6: TNFR2-Induced Cell Death in Kym-1 Cells

Bioactivity of TNFR-binding protein complexes was tested using human Kym-1 cells, which endogenously express both TNF receptors and are highly sensitive to TNF-induced cytotoxicity.

Kym-1 cells (1.5×10$^4$ cells/well) were grown in 96-well flat bottom cell culture plates overnight. Kym-1 cells were incubated with different concentrations of the purified human and mouse complexes of Example 1 for 24 hours at 37° C. Cells were washed with PBS and incubated with crystal violet (20% methanol, 0.5% crystal violet) for 20 minutes to stain viable cells. The dye was removed under rinsing water and cells were air-dried. Crystal violet was resolved with methanol and the optical density was determined at 550 nm. Each sample was analyzed in triplicates and data were analyzed using the software Microsoft Excel and GraphPad Prism 4 (GraphPad, La Jolla, Calif.) (FIG. 8). In Table 6, the calculated EC$_{50}$ values for the cell death induction of the human and mouse proteins are summarized.

TABLE 6

EC$_{50}$ values (nM) of cell death induction using Kym-1 cells by TNFR2-binding protein complexes

| scTNF$_{R2}$ | EHD2-scTNF$_{R2}$ | p53-scTNF$_{R2}$ | GCN4-scTNF$_{R2}$ |
|---|---|---|---|
| 0.3467 | 0.0126 | 0.0106 | 0.0025 |

| sc-mTNF$_{R2}$ | EHD2-sc-mTNF$_{R2}$ | p53-sc-mTNF$_{R2}$ | GCN4-sc-mTNF$_{R2}$ |
|---|---|---|---|
| n/d | 0.4527 | 0.0562 | 0.0057 |

Upon activation of TNFR2, Kym-1 cells express TNF at the cell surface. This TNF is capable of activating TNFR1, which in turn activates cell death pathways, such that Kym-1 cells undergo apoptosis. Bioactivity was elevated with higher oligomerization state. Both tetrameric fusion proteins show a clearly elevated bioactivity compared to dimerized EHD2 protein complexes. Unexpectedly, GCN4-sc-mTNF$_{R2}$, has a up to 10-fold higher bioactivity than p53-sc-mTNF$_{R2}$ in this bioassay. Similar results were obtained for the human scTNF$_{R2}$ variants, where CN4-scTNF$_{R2}$ displayed the highest bioactivity, approximately 5-fold higher than EHD2-scTNF$_{R2}$ and p53-scTNF$_{R2}$.

Example 7: TNFR2-Induced Proliferation of Thymocytes

Bioactivity of the mouse complexes of Example 1 was tested using thymocytes isolated from C57BL/6 mice. Thymus of C57BL/6 mice was isolated and mashed through a 40 µm cell strainer (Flacon). Cells were centrifuged (300×g, 5 min) and washed once with culture medium (RPMI 1640, 10% FCS, 50 µM (3-mercaptoethanol, P/S). Then 1.5×10$^5$ cells were plated onto anti-CD3 (clone 17A2, Biolegend) coated (6 h at 4° C., 1 µg/ml) 96-well plates and cultivated for 4 days in presence of the mouse complexes of Example 1.

Cell proliferation was determined by measuring cell viability via MTT assay. Cells were incubated with MTT (0.5 mg/ml) for 2 hours at 37° C. Then lysis buffer (10% SDS, 20 nM HCl) was added, cells were lysed overnight and the optical density was determined at 550 nm. Each sample was analyzed in triplicates and data were analyzed using the software Microsoft Excel and GraphPad Prism 4 (FIG. 9). Table 7 summarizes the EC$_{50}$ values of the thymocyte proliferation as determined via the MTT assay.

TABLE 7

EC$_{50}$ values (nM) of thymocyte proliferation induction
by TNFR2-binding protein complexes

| sc-mTNF$_{R2}$ | EHD2-sc-mTNF$_{R2}$ | p53-sc-mTNF$_{R2}$ | GCN4-sc-mTNF$_{R2}$ |
|---|---|---|---|
| n/d | 0.0700 | 0.0650 | 0.0185 |

After 4 days of cultivation, GCN4-sc-mTNF$_{R2}$ showed an approx. 3-fold increased bioactivity, evident from lower EC$_{50}$ value in the in vitro thymocyte proliferation induction relative to EHD2-sc-mTNF$_{R2}$, whereas p53-sc-mTNF$_{R2}$ displayed comparable activity with EHD2-sc-mTNF$_{R2}$ in this bioassay.

Example 8: TNFR2-Induced Secretion of Cxcl-2

Bioactivity of the mouse complexes of Example 1 was tested using BV-2 cells. BV-2 cells were stimulated in presence of the mouse complexes of Example 1, supernatants were collected after 24 hours and analyzed by an ELISA specific for Cxcl-2 (BV-2, R&D Systems, Minneapolis Minn.) according to the instructions of the manufacturer. The absorbance at 450 nm was determined and the amount of released Cxcl-2 was determined with the provided standard and calculated using the software GraphPad Prism. Table 8 summarizes the EC$_{50}$ values of the Cxcl-2 secretion as determined via the ELISA (FIG. 10).

TABLE 8

EC$_{50}$ values (nM) of Cxcl-2 secretion induced by
different TNFR2-binding protein complexes

| | |
|---|---|
| SC-mTNF$_{R2}$ | 1.07 |
| EHD2-sc-mTNF$_{R2}$ | 0.44 |
| p53-sc-mTNF$_{R2}$ | 0.13 |
| GCN4-SC-mTNF$_{R2}$ | 0.03 | p53-sc-mTNF$_{R2}$ and particularly GCN4-sc-mTNF$_{R2}$ showed a significantly increased bioactivity, evident from a 3 to 10 fold lower EC$_{50}$ value relative to EHD2-sc-mTNF$_{R2}$ and sc-mTNF$_{R2}$.

Example 9: TNFR2-Induced TNF/TNFR2 Clustering

Bioactivity of the mouse complexes of Example 1 was tested using BV-2 cells. BV-2 cells were stimulated with the mouse complexes of Example 1 for 15 minutes at 37° C. Then cells were immediately washed two times with ice cold PBS and fixed with 4% PFA in PBS solution. Then unspecific binding sites were blocked with 4% BSA in PBS and cells were incubated with antibodies against TNF (HP8001, Hbt) and TNFR2 (AF-426-PB, R&D systems), followed by detection with appropriate fluorescence labeled antibodies. Nuclei were counterstained with DAPI. Stainings were analyzed on a Zeiss Axio Observer Spinning Disc microscope equipped with a Plan-Apochromat 63×/1.4 Oil DIC objective and an Axiocam 503 mono CCD camera. The following excitation lasers and emission filters were used: DAPI: 405 diode laser, 450/50 nm filter; GFP, 488 nm diode laser, 525/50 nm filter; RFP, 561 nm (RFP) diode laser, 600/50 nm filter. Z-stacks of tile regions containing 6×6 images were acquired and maximum intensity projections were calculated. Image processing was done in Zen blue 2.1 software (Zeiss, Germany).

Quantitative image analysis was done with CellProfiler version 2.2.49. Nuclei were segmented via the DAPI staining and a 120 pixel wide ring mask was drawn around each nucleus representing the cell mask. TNF Vesicles were segmented under the cell mask using the A488 staining and unified for each cell. Mean intensity of the TNFR2 signal using the A546 staining was measured under the unified vesicles representing the grade of co-localized vesicles between TNFR2 and TNF per cell (FIG. 11). The results favorably show that both p53-sc-mTNF$_{R2}$ and GCN4-sc-mTNF$_{R2}$ induce formation of signal competent TNF/TNFR2 clusters visible as large white dots within the stimulated cells.

Example 10: Bioactivity Using Immune Cells

Expression of activation markers CD25 and HLA-DR on human T cells and CD25 and TNFR2 on mouse T cells is upregulated in presence of TNFR2-selective proteins.

Blood of volunteer human donors was diluted 1:2 with RPMI medium. Then 30 ml diluted blood was layered over 10 ml Histopaque-1077 (Sigma-Aldrich, Darmstadt, Germany) and centrifuged for 20 min at 800×g without brake. Interphase, including mononuclear cells of peripheral blood (PBMCs) was removed and washed with 30 ml RPMI (300×g, 5 min). For removal of platelets, cells were resuspended in 40 ml RPMI and centrifuged for 5 min at 200×g. Then, CD3+ T cells were isolated by magnetic separation using the Pan T Cell Isolation Kit (Miltenyi Biotech). Purified T cells were resuspended in X-Vivo 15 medium (Lonza, Basel, Switzerland) and cells were plated in αCD3 coated (6 h at 4° C.) 96-well (U form) plates for T cell activation. Cells were cultivated in presence of IL-2 (10 U/ml) and mouse complexes of Example 1 for 4 days. Then surface expression of CD4, CD8, CD25 and HLA-DR was determined by flow cytometry according to manufacturer's instructions (Miltenyi Biotech, Bergisch-Gladbach, Germany) (FIG. 12A).

Spleens from C57BL/6 wildtype mice were dissociated through a 40 µm cell strainer and collected in 10 ml MACS buffer (PBS, 0.5% BSA, 2 mM EDTA). Splenocytes were centrifuged (300 g, 5 min) and washed once with 10 ml MACS buffer. Then CD3$^+$ T cells were isolated using the FACS Aria III and plated in anti-CD3 coated (6 h at 4° C.) 96-well (U form) plates for T cell activation. T cells were cultivated in presence of IL-2 and mouse proteins of Example 1 for 4 days. Then expression of CD25 and TNFR2 was determined by flow cytometry according to manufacturer's instructions (Miltenyi Biotech, Bergisch-Gladbach). Data were acquired using a MACSQuant Analyzer 10 (Miltenyi) and analyzed with FlowJo (FlowJo, LLC) (FIG. 12B).

In particular, GCN4-sc-mTNF$_{R2}$ and p53-sc-mTNF$_{R2}$ displayed superior bioactivity relative to EHD2-sc-mTNF$_{R2}$.

Example 11: Bioactivity Using Mouse T Cells

TNFR2 is involved in expansion of Tregs and thereby contributes to immune regulation and immune suppression. Spleens from C57BL/6 wildtype mice were dissociated through a 40 µm cell strainer and collected in 10 ml MACS buffer (PBS, 0.5% BSA, 2 mM EDTA). Splenocytes were centrifuged (300 g, 5 min) and washed once with 10 ml MACS buffer. Then CD3+ T cells were isolated using the FACS Aria III and plated in anti-CD3 coated (6 h at 4° C.) 96-well (U form) plates for T cell activation. T cells were cultivated in presence of IL-2 and complexes of Example 1 for 4 days. Then expression of CD25, TNFR2 and FoxP3 was determined by flow cytometry according to manufacturer's instructions (Miltenyi Biotech, Bergisch-Gladbach). Data were acquired using a MACSQuant Analyzer 10 (Miltenyi) and analyzed with FlowJo (FlowJo, LLC) (FIG. 13)

The results show that the dodecavalent complexes induce a superior Treg expansion compared to the hexavalent complexes.

Example 12: In Vivo Bioactivity

EHD2-sc-mTNF$_{R2}$, p53-sc-mTNF$_{R2}$ and GCN4-sc-mTNF$_{R2}$ of Example 1 (1 mg/kg) were administered intraperitoneal (i.p.) to C57BL/6 wildtype mice. After 4 days a second injection (1 mg/kg) was applied. After 7 days, spleens were excised and splenocytes were isolated. Isolated spleens were dissociated through a 40 µm cell strainer and collected in 10 ml MACS buffer (PBS, 0.5% BSA, 2 mM EDTA). Splenocytes were centrifuged (300 g, 5 min) and incubated in 3 ml RBC buffer (0.15 M NH$_4$Cl, 10 mM KHCO$_3$, 0.1 M EDTA) per spleen for 5 minutes at room temperature to lyse red blood cells. Then 10 ml MACS buffer was added and splenocytes were centrifuged for 5 min at 300 g. Cells were washed once with 10 ml MACS buffer (5 min, 300×g) and afterwards collected in MACS buffer. Expression of markers CD25 and FoxP3 within the subpopulation of CD4$^+$ T cells was determined by flow cytometry according to manufacturer's instructions (Miltenyi Biotech, Bergisch-Gladbach) (FIG. 14A).

In vivo both p53-sc-mTNF$_{R2}$ and GCN4-sc-mTNF$_{R2}$ are more potent than EHD2-sc-mTNF$_{R2}$, as indicated by the increased amount of regulatory T cells in the spleen of treated mice.

Tolerance of the proteins was determined by measuring CRP levels in the blood after administration (1 mg/kg, i.p.) of the mouse proteins of Example 1. Therefore, total blood was withdrawn 24 hours and 72 hours after injection and CRP levels were determined by an ELISA specific for mouse CRP (R&D Systems) according to the instructions of the manufacturer.

No differences between the different proteins were observed indicating the tolerance of the different oligomeric variants (FIG. 14B).

Example 13: Dodecavalent TNFR2-Selective Agonists Using VASP as Tetramerization Domain or Fc as Dimerization Domain The tetramerization domain of human VASP (aa 336-380) (SEQ ID NO: 86) was fused to the N-terminal end of a human single-chain TNF variant (scTNF$_{R2}$, D143N/A145R) (SEQ ID NO: 81) via a peptide linker L3 consisting of GAPGGGSGGGSGGGSGGGSGGGSGGSEFLA (SEQ ID NO: 41) resulting in VASP-scTNF$_{R2}$ (SEQ ID NO: 90).

Furthermore, the human scTNF$_{R2}$ variant (SEQ ID NO: 81) was fused to the N- and C-terminal ends of the dimerization domain of Fc mutant Fcγ1 (Δab; E233P, L234V, L235A, ΔG236, A327G, A330S, P331S) with abolished ADCC/CDC functionality (SEQ ID NO: 83). The trivalent PLGs are connected to the N-terminus of the Fc (Δab) dimerization domain via a peptide linker L3 consisting of GGSGGGGSGG (SEQ ID NO: 99) and to the C-terminus via a peptide linker L4 consisting of GGSGGGSSGG (SEQ ID NO: 100) to give scTNF$_{R2}$-Fc-scTNF$_{R2}$ (SEQ ID NO: 87).

The overall codon usage of the constructs was adapted for expression in mammalian cells. To facilitate purification, an N-terminal His-tag was introduced in all constructs.

The complexes, VASP-scTNF$_{R2}$ and scTNF$_{R2}$-Fc-scTNF$_{R2}$, were produced in HEK293-6E cells, purified by Ni$^{2+}$-NTA IMAC and analyzed under native buffer conditions by size exclusion chromatography (FIG. 15A). scTNF$_{R2}$-Fc-scTNF$_{R2}$ eluted as a major peak corresponding to dimeric assembly and VASP-scTNF$_{R2}$ eluted as a major peak corresponding to tetrameric assembly. Disulfide-connected dimers of the expected molecular mass were confirmed by SDS-PAGE for scTNF$_{R2}$-Fc-scTNF$_{R2}$ (FIG. 15B, Table 9). VASP-scTNF$_{R2}$ showed in SDS-PAGE bands of similar size at reducing and non-reducing conditions, in accordance with non-covalent assembly of the VASP tetramerization domain. SDS-PAGE further confirmed purity and integrity of the expressed polypeptide chains.

To investigate bioactivity, Kym-1 cells were stimulated with scTNF$_{R2}$-Fc-scTNF$_{R2}$, VASP-scTNF$_{R2}$ and hexavalent EHD2-scTNF$_{R2}$ as control. The cell viability was determined by crystal violet assay after 16 h. Here, an EC$_{50}$ value of 37 pM was determined for the hexavalent EHD2-scTNF$_{R2}$ protein. In contrast, the two dodecavalent molecules scTNF$_{R2}$-Fc-scTNF$_{R2}$ and VASP-scTNF$_{R2}$ had EC$_{50}$ values of 8.5 and 7.0 pM (FIG. 15C). Thus, the bioactivity of the dodecavalent fusion proteins was approximately 5-fold increased compared to the hexavalent protein.

TABLE 9

Calculated molecular mass of further TNF$_{R2}$ binding protein complexes of the present invention

|  | VASP-scTNF$_{R2}$ | scTNF$_{R2}$-Fc-scTNF$_{R2}$ |
|---|---|---|
| MW [kDa] | 247.9 | 263.5 |

The present invention relates to the following items:
1. A tumour necrosis factor receptor (TNFR) binding protein complex comprising 12 or more protein ligands (PLs) that specifically bind to the extracellular part of the same TNFR, preferably to TNFR2.
2. The TNFR binding protein complex of item 1, comprising between 12 to 18, preferably 12 PLs.
3. The TNFR binding protein complex of items 1 or 2, wherein between 2 to 6 PLs, preferably 3, form a protein ligand group (PLG) with the following structure:

PL$_1$-L1-PL$_2$-L1-PL$_3$-L1-PL$_4$-L1-PL$_5$-L1-PL$_6$, wherein
any of PL$_4$ to PL$_6$, and/or L1 may be absent or present, L1 in each case independently means a peptide linker.
4. The TNFR binding protein complex of item 3, comprising between 2 to 6 PLGs and each PLG comprising between 2 to 6 PLs.
5. The TNFR binding protein complex of items 3 or 4, wherein the PLGs are linked to each other through a peptide linker 2 (L2) to form a PLG-multimer.
6. The TNFR binding protein complex of any of items 3 to 5, further comprising two or more polymerization domains (PD), preferably each linked via their N- and/or C-terminus to a PLG or a PLG-multimer, optionally through a peptide linker 3 (L3).
7. The TNFR binding protein complex of item 6, wherein the PD is selected from the group consisting of a dimerization domain, a trimerization domain or a tetramerization domain.

8. The TNFR binding protein complex of item 7, wherein the:
   (i) dimerization domain is selected from the group consisting of heavy chain domain 2 (CH2) of IgM (MHD2) or IgE (EHD2), immunoglobulin Fc region, heavy chain domain 3 (CH3) of IgG or IgA, heavy chain domain 4 (CH4) of IgM or IgE, Fab, Fab$_2$, leucine zipper motifs, barnase-barstar dimers, miniantibodies, and ZIP miniantibodies;
   (ii) trimerization domain is selected from the group consisting of tenascin C (TNC), the trimerization region of the C-terminal noncollagenous domain (NC1) of collagen XVIII, Fab3 like molecules, and TriBi-minibodies; or
   (iii) tetramerization domain is selected from the group consisting of the tetramerization domain of p53, the tetramerization domain of the general control protein 4 (GCN4), the tetramerization domain of VASP (vasodilator stimulated phosphoprotein), tandem diabodies, and di-diabodies.
9. The TNFR binding protein complex of any of items 6 to 8(i) and (ii), wherein each PD comprises at least one amino acid residue capable of forming a covalent bond to at least one amino acid residue in another PD, preferably a Cys residue.
10. The TNFR binding protein complex of any of items 6 to 9, wherein L3 has a length of between 4 to 32 acids and wherein L3 optionally comprises at least one glycosylation motif, preferably at least one motif is glycosylated.
11. The TNFR binding protein complex of item 10, wherein L3 comprises one or more repetitive units selected from the group consisting of $(GGS)_p$, $(GGGS)_n$ or $(GGSGG)_m$, wherein p is an integer between 1 and 10, n is an integer between 1 and 8 and m is an integer between 1 to 6.
12. The TNFR binding protein complex of any of items 1 to 11, wherein each PL is independently of each other selected from the group consisting of a TNF homology domain of a TNF-ligand family member protein (THD), a scaffold-protein and a peptidomimetic.
13. The TNFR binding protein complex of item 12, wherein the TNF-ligand family member protein is selected from the group consisting of TNF, TNF-related apoptosis inducing ligand (TRAIL or TNFSF10, tumor necrosis factor superfamily member), CD40L (TNFSF5), CD27L (TNFSF7), CD30L (TNFSF8), FasL (TNFSF6), 4-1BBL (TNFSF9), OX40L (TNFSF4), EDA; LTA (TNFSF1), LTB (TNFSF3), CD153 (TNFSF8), RANKL (TNFSF11), TWEAK (TNFSF12), APRIL (TNFSF13), BAFF (TNFSF13B), LIGHT (TNFSF14), VEGI (TNFSF15), and GITRL (TNFSF18).
14. The TNFR binding protein complex of any of items 1 to 12, wherein the TNF-ligand family member protein is TNF or LTA.
15. The TNFR binding protein complex of item 14, wherein said TNF comprises a sequence according to SEQ ID NO: 43 which comprises one or more TNFR2 specific mutations selected from the group consisting of D143Y, D143F, D143E, D143N, E146Q, E146H, E146K A145R/S147T, Q88N/T89S/A145S/E146A/S147D, Q88N/A145I/E146G/S147D, A145H/E146S/S147D, A145H/S147D, L29V/A145D/E146D/S147D, A145N/E146D/S147D, A145T/E146S/S147D, A145Q/E146D/S147D, A145T/E146D/S147D, A145D/E146G/S147D, A145D/S147D, A145K/E146D/S147T, A145R/E146T/S147D, A145R//S147T, E146D/S147D, E146N/S147, K65W, D143N, D143E, D143F, D143W, D143Y, D143V, D143V/F144L/A145S, D143N/A145R, D143V/A145S, A145R, A145H, A145K, A145F, and A145W.
16. The TNFR binding protein complex of any of items 12 to 15, wherein the C-terminus of the first THD, respectively, which is defined by the C-terminal consensus sequence $$\text{-S/T/V-F/Y/S-F-G-A/L/V/I-}X_1, \quad (\text{SEQ ID NO: 1})$$

is linked to the N-terminus of the second THD, which is defined by the N-terminal consensus sequence $$X_2\text{-V/A/F-A-H-V/L/I/Y} \quad (\text{SEQ ID NO: 2})$$

or $$X_3\text{-V/W/F/C-A/L-E/Y/Q/H-L}, \quad (\text{SEQ ID NO: 3})$$

through L1, which has a length of 2 to 20 amino acids, preferably 2 to 15 amino acids, more preferably 3 to 10 amino acids and most preferably of 3 to 5 amino acids; wherein $X_1$ is a non-polar/hydrophob or polar/neutral amino acid, preferably selected from the group consisting of F, V, Q, A, I, L, and Y;
wherein $X_2$ is selected from the group consisting of P, K, V, I, and A; and
wherein $X_3$ is selected from the group consisting of D, S, M, and I;
optionally further comprising one to four further THDs each consecutively linked to each other in the same way as the first and second THD.
17. The TNFR binding protein complex of item 12, wherein the peptidomimetic is selected from the group consisting of (lipoprotein-associated coagulation inhibitor (LACI-D1); affilins, selected from human-γ B crystalline or human ubiquitin; cystatin; Sac7D from *Sulfolobus acidocaldarius*; lipocalin and anticalins derived from lipocalins; designed ankyrin repeat domains (DARPins); SH3 domain of Fyn; Kunits domain of protease inhibitors; monobodies selected from the 10$^{th}$ type III domain of fibronectin; adnectins; cysteine knot miniproteins; atrimers; evibodies, selected from CTLA4-based binders, affibodies, selected from three-helix bundle from Z-domain of protein A from *Staphylococcus aureus*; trans-bodies, selected from human transferrin; tetranectins, selected from monomeric or trimeric human C-type lectin domain; microbodies, selected from trypsin-inhibitor-II; affilins; armadillo repeat proteins.
18. A nucleic acid encoding a TNFR binding protein complex according to any of items 1 to 17 or a PLG comprised therein.
19. A vector comprising a nucleic acid according to item 18.
20. A TNFR binding protein complex according to any of items 1 to 17, a nucleic acid according to item 18 or a vector according to item 19 for use as a medicament.
21. A pharmaceutical composition comprising as an active agent a TNFR binding protein complex according to any of items 1 to 17 or a nucleic acid according to item 18 or a vector according to item 19.

22. A TNFR binding protein complex according to any of items 1 to 17 or a nucleic acid according to item 18 or a vector according to item 19 or a pharmaceutical composition according to item 21 for use in the diagnosis, prophylaxis or treatment of hyperproliferative disorders or inflammatory disorders, preferably cancer or malignancies of the hematologic system, autoimmune disorders and neurodegenerative diseases.

The invention claimed is:

1. A tumor necrosis factor receptor (TNFR) binding protein complex comprising 12 or more protein ligands (PLs) that specifically bind to the extracellular part of the same TNFR.

2. The TNFR binding protein complex of claim 1, comprising between 2 to 18 PLs.

3. The TNFR binding protein complex of claim 1, wherein between 2 to 6 PLs, form a protein ligand group (PLG) with the following structure:

$PL_1$-L1-$PL_2$-L1-$PL_3$-L1-$PL_4$-L1-$PL_5$-L1-$PL_6$, wherein any of $PL_4$ to $PL_6$, and/or L1 may be absent or present, L1 in each case independently means a peptide linker.

4. The TNFR binding protein complex of claim 3, comprising between 2 to 6 PLGs and each PLG comprising between 2 to 6 PLs.

5. The TNFR binding protein complex of claim 3, wherein the PLGs are linked to each other through a peptide linker 2 (L2) to form a PLG-multimer.

6. The TNFR binding protein complex of claim 3, further comprising two or more polymerization domains (PD).

7. The TNFR binding protein complex of claim 6, wherein the two or more PD are selected from the group consisting of dimerization domains, trimerization domains or tetramerization domains.

8. The TNFR binding protein complex of claim 1, wherein each PL is independently of each other selected from the group consisting of a TNF homology domain of a TNF-ligand family member protein (THD), a scaffold-protein and a peptidomimetic.

9. The TNFR binding protein complex of claim 1, wherein, when at least one of the PLs is a TNF-ligand family member protein (THD), the TNF-ligand family member protein is TNF or LTA.

10. The TNFR binding protein complex of claim 8, wherein, when at least one of the PLs is a TNF homology domain of a TNF-ligand family member protein (THD) the C-terminus of a first THD, which is defined by a C-terminal consensus sequence (SEQ ID NO: 1)
-S/T/V-F/Y/S-F-G-A/L/V/I-$X_1$, is linked to the N-terminus of a second THD, which is defined by an N-terminal consensus sequence (SEQ ID NO: 2)
$X_2$-V/A/F-A-H-V/L/I/Y or (SEQ ID NO: 3)
$X_3$-V/W/F/C-A/L-E/Y/Q/H-L, through L1, which has a length of 2 to 20 amino acids;

wherein $X_1$ is a non-polar/hydrophobic or polar/neutral amino acid;

wherein $X_2$ is selected from the group consisting of P, K, V, I, and A; and wherein $X_3$ is selected from the group consisting of D, S, M, and I;

optionally further comprising one to four further THDs each consecutively linked to each other in the same way as the first and second THD.

11. The TNFR binding protein complex of claim 1, wherein the TNFR is TNFR 2.

12. The TNFR binding protein complex of claim 6, wherein the two or more polymerization domains (PD) are linked via their N- and/or C-terminus to a PLG or a PLG-multimer through a peptide linker 3 (L3).

13. The TNFR binding protein complex of claim 7, wherein
  (i) when the two or more PD are dimerization domains, the dimerization domains are selected from the group consisting of heavy chain domain 2 (CH2) of IgM (MHD2) or IgE (EHD2), immunoglobulin Fc region, heavy chain domain 3 (CH3) of IgG or IgA, heavy chain domain 4 (CH4) of IgM or IgE, Fab, Fab2, leucine zipper motifs, barnase-barstar dimers, miniantibodies, and ZIP miniantibodies;
  (ii) when the two or more PDs are trimerization domains, the trimerization domains are selected from the group consisting of tenascin C (TNC), the trimerization region of the C-terminal noncollagenous domain (NC1) of collagen XVIII, fab3-like molecules, and TriBi-miniantibodies; or
  (iii) when the two or more PD are tetramerization domains, the tetramerization domains are selected from the group consisting of the tetramerization domain of p53, the tetramerization domain of the general control protein 4 (GCN4), the tetramerization domain of VASP (vasodilator stimulated phosphoprotein), tandem diabodies, and di-diabodies.

14. The TNFR binding protein complex of claim 8, wherein, when at least one of the PL is a TNF homology domain of a TNF-ligand family member protein (THD), the TNF-ligand family member protein is selected from the group consisting of TNF, TNF-related apoptosis inducing ligand (TRAIL or TNFSF10, tumor necrosis factor superfamily member), CD40L (TNFSF5), CD27L (TNFSF7), CD30L (TNFSF8), FasL (TNFSF6), 4-1BBL (TNFSF9), OX40L (TNFSF4), EDAM, LTA (TNFSF1), LTB (TNF SF3), CD153 (TNF SF 8), RANKL (TNF SF 11), TWEAK (TNF SF 12), APRIL (TNFSF13), BAFF (TNFSF13B), LIGHT (TNFSF14), VEGI (TNFSF15), and GITRL (TNFSF18).

15. The TNFR binding protein complex of claim 9, wherein, when at least one of the PLs is TNF, the TNF comprises a sequence according to SEQ ID NO: 43 which comprises one or more TNFR2 specific mutations selected from the group consisting of D143Y, D143F, D143E, D143N, E146Q, E146H, E146K A145R/S147T, Q88N/T89S/A145S/E146A/S147D, Q88N/A145I/E146G/S147D, A145H/E146S/S147D, A145H/S147D, L29V/A145D/E146D/S147D, A145N/E146D/S147D, A145T/E146S/S147D, A145Q/E146D/S147D, A145T/E146D/S147D, A145D/E146G/S147D, A145D/S147D, A145K/E146D/S147T, A145R/E146T/S147D, A145R//S147T, E146D/S147D, E146N/5147, K65W, D143N, D143E, D143F, D143W, D143Y, D143V, D143V/F144L/A145S, D143N/A145R, D143V/A145S, A145R, A145H, A145K, A145F, and A145W.

16. The TNFR binding protein complex of claim 10, wherein L1 has a length of 2 to 15 amino acids, and wherein $X_1$ is selected from the group consisting of F, V, Q, A, I, L, and Y.

17. A pharmaceutical composition comprising as an active agent the TNFR binding protein complex according to claim 1.

18. A nucleic acid encoding the TNFR binding protein complex according to claim 1 or a PLG comprised therein.

19. A vector comprising the nucleic acid according to claim 18.

* * * * *

```
                        SEQUENCE LISTING

<160> NUMBER OF SEQ ID NOS: 100

<210> SEQ ID NO 1
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: can be S, T. or V
<220> FEATURE:
<221> NAME/KEY: MISC_FEATURE
<222> LOCATION: (2)..(2)
<223> OTHER INFORMATION: can be F, Y, or S
<220> FEATURE:
<221> NAME/KEY: MISC_FEATURE
<222> LOCATION: (5)..(5)
<223> OTHER INFORMATION: can be A, L, V, or I
<220> FEATURE:
<221> NAME/KEY: MISC_FEATURE
<222> LOCATION: (6)..(6)
<223> OTHER INFORMATION: can be F, V, Q, A, I, L, or Y

<400> SEQUENCE: 1

Xaa Xaa Phe Gly Xaa Xaa
1               5

<210> SEQ ID NO 2
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: can  be P, K, V, I, or A
<220> FEATURE:
<221> NAME/KEY: MISC_FEATURE
<222> LOCATION: (2)..(2)
<223> OTHER INFORMATION: can  be V, A, or F
<220> FEATURE:
<221> NAME/KEY: MISC_FEATURE
<222> LOCATION: (5)..(5)
<223> OTHER INFORMATION: can  be V, L, I, Y
<220> FEATURE:
<221> NAME/KEY: MISC_FEATURE
<222> LOCATION: (5)..(5)
<223> OTHER INFORMATION: can  be V, L, I, or Y

<400> SEQUENCE: 2

Xaa Xaa Ala His Xaa
1               5

<210> SEQ ID NO 3
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: can be D, S, M, or I
<220> FEATURE:
<221> NAME/KEY: MISC_FEATURE
<222> LOCATION: (2)..(2)
<223> OTHER INFORMATION: can be V, W, F or C
<220> FEATURE:
<221> NAME/KEY: MISC_FEATURE
<222> LOCATION: (3)..(3)
<223> OTHER INFORMATION: can be A or L
```

```
<220> FEATURE:
<221> NAME/KEY: MISC_FEATURE
<222> LOCATION: (4)..(4)
<223> OTHER INFORMATION: can be E, Y, Q, or H

<400> SEQUENCE: 3

Xaa Xaa Xaa Xaa Leu
1               5

<210> SEQ ID NO 4
<211> LENGTH: 4
<212> TYPE: PRT
<213> ORGANISM: Artificial Sequence
<220> FEATURE:
<223> OTHER INFORMATION: Peptide linker

<400> SEQUENCE: 4

Gly Gly Gly Gly
1

<210> SEQ ID NO 5
<211> LENGTH: 5
<212> TYPE: PRT
<213> ORGANISM: Artificial Sequence
<220> FEATURE:
<223> OTHER INFORMATION: Peptide linker

<400> SEQUENCE: 5

Gly Gly Gly Gly Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Peptide linker

<400> SEQUENCE: 6

Gly Gly Gly Gly Gly Gly
1               5

<210> SEQ ID NO 7
<211> LENGTH: 4
<212> TYPE: PRT
<213> ORGANISM: Artificial Sequence
<220> FEATURE:
<223> OTHER INFORMATION: Peptide linker

<400> SEQUENCE: 7

Ser Gly Gly Gly
1

<210> SEQ ID NO 8
<211> LENGTH: 4
<212> TYPE: PRT
<213> ORGANISM: Artificial Sequence
<220> FEATURE:
<223> OTHER INFORMATION: Peptide linker

<400> SEQUENCE: 8

Gly Ser Gly Gly
1

<210> SEQ ID NO 9
<211> LENGTH: 4
<212> TYPE: PRT
```

```
<213> ORGANISM: Artificial Sequence
<220> FEATURE:
<223> OTHER INFORMATION: Peptide linker

<400> SEQUENCE: 9

Gly Gly Ser Gly
1

<210> SEQ ID NO 10
<211> LENGTH: 4
<212> TYPE: PRT
<213> ORGANISM: Artificial Sequence
<220> FEATURE:
<223> OTHER INFORMATION: Peptide linker

<400> SEQUENCE: 10

Gly Gly Gly Ser
1

<210> SEQ ID NO 11
<211> LENGTH: 5
<212> TYPE: PRT
<213> ORGANISM: Artificial Sequence
<220> FEATURE:
<223> OTHER INFORMATION: Peptide linker

<400> SEQUENCE: 11

Ser Gly Gly Gly Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Peptide linker

<400> SEQUENCE: 12

Gly Ser Gly Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Peptide linker

<400> SEQUENCE: 13

Gly Gly Ser Gly Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Peptide linker

<400> SEQUENCE: 14

Gly Gly Gly Ser Gly
1               5

<210> SEQ ID NO 15
<211> LENGTH: 5
<212> TYPE: PRT
<213> ORGANISM: Artificial Sequence
```

```
<220> FEATURE:
<223> OTHER INFORMATION: Peptide linker

<400> SEQUENCE: 15

Gly Gly Gly Gly Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Peptide linker

<400> SEQUENCE: 16

Gly Gly Ser Gly Gly Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Peptide linker

<400> SEQUENCE: 17

Gly Gly Ser Gly Gly Ser Gly Gly Ser
1               5

<210> SEQ ID NO 18
<211> LENGTH: 12
<212> TYPE: PRT
<213> ORGANISM: Artificial Sequence
<220> FEATURE:
<223> OTHER INFORMATION: Peptide linker

<400> SEQUENCE: 18

Gly Gly Ser Gly Gly Ser Gly Gly Ser Gly Gly Ser
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Peptide linker

<400> SEQUENCE: 19

Gly Gly Ser Gly Gly Ser Gly Gly Ser Gly Gly Ser Gly Gly Ser
1               5                   10                  15

<210> SEQ ID NO 20
<211> LENGTH: 18
<212> TYPE: PRT
<213> ORGANISM: Artificial Sequence
<220> FEATURE:
<223> OTHER INFORMATION: Peptide linker

<400> SEQUENCE: 20

Gly Gly Ser Gly Gly Ser Gly Gly Ser Gly Gly Ser Gly Gly Ser Gly
1               5                   10                  15

Gly Ser

<210> SEQ ID NO 21
<211> LENGTH: 21
<212> TYPE: PRT
```

<213> ORGANISM: Artificial sequence
<220> FEATURE:
<223> OTHER INFORMATION: Peptide linker

<400> SEQUENCE: 21

Gly Gly Ser Gly Gly Ser Gly Gly Ser Gly Gly Ser Gly Gly Ser Gly
1               5                   10                  15
Gly Ser Gly Gly Ser
            20

<210> SEQ ID NO 22
<211> LENGTH: 24
<212> TYPE: PRT
<213> ORGANISM: Artificial Sequence
<220> FEATURE:
<223> OTHER INFORMATION: Peptide linker

<400> SEQUENCE: 22

Gly Gly Ser Gly Gly Ser Gly Gly Ser Gly Gly Ser Gly Gly Ser Gly
1               5                   10                  15
Gly Ser Gly Gly Ser Gly Gly Ser
            20

<210> SEQ ID NO 23
<211> LENGTH: 27
<212> TYPE: PRT
<213> ORGANISM: Artificial Sequence
<220> FEATURE:
<223> OTHER INFORMATION: Peptide linker

<400> SEQUENCE: 23

Gly Gly Ser Gly Gly Ser Gly Gly Ser Gly Gly Ser Gly Gly Ser Gly
1               5                   10                  15
Gly Ser Gly Gly Ser Gly Gly Ser Gly Gly Ser
            20                  25

<210> SEQ ID NO 24
<211> LENGTH: 8
<212> TYPE: PRT
<213> ORGANISM: Artificial Sequence
<220> FEATURE:
<223> OTHER INFORMATION: Peptide linker

<400> SEQUENCE: 24

Gly Gly Gly Ser Gly Gly Gly Ser
1               5

<210> SEQ ID NO 25
<211> LENGTH: 12
<212> TYPE: PRT
<213> ORGANISM: Artificial Sequence
<220> FEATURE:
<223> OTHER INFORMATION: Peptide linker

<400> SEQUENCE: 25

Gly Gly Gly Ser Gly Gly Gly Ser Gly Gly Gly Ser
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Peptide linker

<400> SEQUENCE: 26

Gly Gly Gly Ser Gly Gly Gly Ser Gly Gly Gly Ser Gly Gly Gly Ser
1               5                   10                  15

<210> SEQ ID NO 27
<211> LENGTH: 20
<212> TYPE: PRT
<213> ORGANISM: Artificial Sequence
<220> FEATURE:
<223> OTHER INFORMATION: Peptide linker

<400> SEQUENCE: 27

Gly Gly Gly Ser Gly Gly Gly Ser Gly Gly Gly Ser Gly Gly Gly Ser
1               5                   10                  15

Gly Gly Gly Ser
            20

<210> SEQ ID NO 28
<211> LENGTH: 24
<212> TYPE: PRT
<213> ORGANISM: Artificial Sequence
<220> FEATURE:
<223> OTHER INFORMATION: Peptide linker

<400> SEQUENCE: 28

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 29
<211> LENGTH: 28
<212> TYPE: PRT
<213> ORGANISM: Artificial Sequence
<220> FEATURE:
<223> OTHER INFORMATION: Peptide linker

<400> SEQUENCE: 29

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser
            20                  25

<210> SEQ ID NO 30
<211> LENGTH: 10
<212> TYPE: PRT
<213> ORGANISM: Artificial Sequence
<220> FEATURE:
<223> OTHER INFORMATION: Peptide linker

<400> SEQUENCE: 30

Gly Gly Ser Gly Gly Gly Gly Ser Gly Gly
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Peptide linker

<400> SEQUENCE: 31

Gly Gly Ser Gly Gly Gly Gly Ser Gly Gly Gly Gly Ser Gly Gly
1               5                   10                  15

```
<210> SEQ ID NO 32
<211> LENGTH: 20
<212> TYPE: PRT
<213> ORGANISM: Artificial Sequence
<220> FEATURE:
<223> OTHER INFORMATION: Peptide linker

<400> SEQUENCE: 32

Gly Gly Ser Gly Gly Gly Ser Gly Gly Gly Ser Gly Gly
1               5                   10                  15

Gly Ser Gly Gly
            20

<210> SEQ ID NO 33
<211> LENGTH: 25
<212> TYPE: PRT
<213> ORGANISM: Artificial Sequence
<220> FEATURE:
<223> OTHER INFORMATION: Peptide linker

<400> SEQUENCE: 33

Gly Gly Ser Gly Gly Gly Ser Gly Gly Gly Ser Gly Gly
1               5                   10                  15

Gly Ser Gly Gly Gly Gly Ser Gly Gly
            20                  25

<210> SEQ ID NO 34
<211> LENGTH: 10
<212> TYPE: PRT
<213> ORGANISM: Artificial Sequence
<220> FEATURE:
<223> OTHER INFORMATION: Peptide linker

<400> SEQUENCE: 34

Gly Gly Ser Gly Ser Gly Gly Ser Gly Ser
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Peptide linker

<400> SEQUENCE: 35

Gly Gly Ser Gly Ser Gly Gly Ser Gly Ser Gly Gly Ser Gly Ser
1               5                   10                  15

<210> SEQ ID NO 36
<211> LENGTH: 20
<212> TYPE: PRT
<213> ORGANISM: Artificial Sequence
<220> FEATURE:
<223> OTHER INFORMATION: Peptide linker

<400> SEQUENCE: 36

Gly Gly Ser Gly Ser Gly Gly Ser Gly Ser Gly Gly Ser Gly Ser Gly
1               5                   10                  15

Gly Ser Gly Ser
            20

<210> SEQ ID NO 37
<211> LENGTH: 25
<212> TYPE: PRT
<213> ORGANISM: Artificial Sequence
<220> FEATURE:
```

```
<223> OTHER INFORMATION: Peptide linker

<400> SEQUENCE: 37

Gly Gly Ser Gly Ser Gly Gly Ser Gly Ser Gly Gly Ser Gly
1               5                   10                  15

Gly Ser Gly Ser Gly Gly Ser Gly Ser
            20                  25

<210> SEQ ID NO 38
<211> LENGTH: 10
<212> TYPE: PRT
<213> ORGANISM: Artificial Sequence
<220> FEATURE:
<223> OTHER INFORMATION: Peptide linker

<400> SEQUENCE: 38

Gly Gly Ser Gly Gly Gly Gly Ser Gly Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Peptide linker

<400> SEQUENCE: 39

Gly Gly Ser Gly Gly Gly Ser Ser Gly Gly
1               5                   10

<210> SEQ ID NO 40
<211> LENGTH: 29
<212> TYPE: PRT
<213> ORGANISM: Artificial Sequence
<220> FEATURE:
<223> OTHER INFORMATION: Peptide linker

<400> SEQUENCE: 40

Gly Ala Pro Gly Gly Gly Ser Gly Gly Ser Gly Gly Gly Ser Gly
1               5                   10                  15

Gly Gly Ser Gly Gly Gly Ser Gly Gly Ser Gly Ile Arg
            20                  25

<210> SEQ ID NO 41
<211> LENGTH: 30
<212> TYPE: PRT
<213> ORGANISM: Artificial Sequence
<220> FEATURE:
<223> OTHER INFORMATION: Peptide linker

<400> SEQUENCE: 41

Gly Ala Pro Gly Gly Gly Ser Gly Gly Ser Gly Gly Gly Ser Gly
1               5                   10                  15

Gly Gly Ser Gly Gly Gly Ser Gly Gly Ser Glu Phe Leu Ala
            20                  25                  30

<210> SEQ ID NO 42
<211> LENGTH: 145
<212> TYPE: PRT
<213> ORGANISM: Homo sapiens

<400> SEQUENCE: 42

Val Ala His Val Val Ala Asn Pro Gln Ala Glu Gly Gln Leu Gln Trp
1               5                   10                  15
```

Leu Asn Arg Arg Ala Asn Ala Leu Leu Ala Asn Gly Val Glu Leu Arg
            20                  25                  30

Asp Asn Gln Leu Val Val Pro Ser Glu Gly Leu Tyr Leu Ile Tyr Ser
        35                  40                  45

Gln Val Leu Phe Lys Gly Gln Gly Cys Pro Ser Thr His Val Leu Leu
    50                  55                  60

Thr His Thr Ile Ser Arg Ile Ala Val Ser Tyr Gln Thr Lys Val Asn
65                  70                  75                  80

Leu Leu Ser Ala Ile Lys Ser Pro Cys Gln Arg Glu Thr Pro Glu Gly
                85                  90                  95

Ala Glu Ala Lys Pro Trp Tyr Glu Pro Ile Tyr Leu Gly Gly Val Phe
            100                 105                 110

Gln Leu Glu Lys Gly Asp Arg Leu Ser Ala Glu Ile Asn Arg Pro Asp
        115                 120                 125

Tyr Leu Asp Phe Ala Glu Ser Gly Gln Val Tyr Phe Gly Ile Ile Ala
    130                 135                 140

Leu
145

<210> SEQ ID NO 43
<211> LENGTH: 154
<212> TYPE: PRT
<213> ORGANISM: Homo sapiens

<400> SEQUENCE: 43

Ser Ser Arg Thr Pro Ser Asp Lys Pro Val Ala His Val Val Ala Asn
1               5                   10                  15

Pro Gln Ala Glu Gly Gln Leu Gln Trp Leu Asn Arg Arg Ala Asn Ala
            20                  25                  30

Leu Leu Ala Asn Gly Val Glu Leu Arg Asp Asn Gln Leu Val Val Pro
        35                  40                  45

Ser Glu Gly Leu Tyr Leu Ile Tyr Ser Gln Val Leu Phe Lys Gly Gln
    50                  55                  60

Gly Cys Pro Ser Thr His Val Leu Leu Thr His Thr Ile Ser Arg Ile
65                  70                  75                  80

Ala Val Ser Tyr Gln Thr Lys Val Asn Leu Leu Ser Ala Ile Lys Ser
                85                  90                  95

Pro Cys Gln Arg Glu Thr Pro Glu Gly Ala Glu Ala Lys Pro Trp Tyr
            100                 105                 110

Glu Pro Ile Tyr Leu Gly Gly Val Phe Gln Leu Glu Lys Gly Asp Arg
        115                 120                 125

Leu Ser Ala Glu Ile Asn Arg Pro Asp Tyr Leu Asp Phe Ala Glu Ser
    130                 135                 140

Gly Gln Val Tyr Phe Gly Ile Ile Ala Leu
145                 150

<210> SEQ ID NO 44
<211> LENGTH: 162
<212> TYPE: PRT
<213> ORGANISM: Homo sapiens

<400> SEQUENCE: 44

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
            35                  40                  45

His Leu Arg Asn Gly Glu Leu Val Ile His Glu Lys Gly Phe Tyr Tyr
 50                  55                  60

Ile Tyr Ser Gln Thr Tyr Phe Arg Phe Gln Glu Glu Ile Lys Glu Asn
 65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
            115                 120                 125

Phe Glu Leu Lys Glu Asn Asp Arg Ile Phe Val Ser Val Thr Asn Glu
130                 135                 140

His Leu Ile Asp Met Asp His Glu Ala Ser Phe Phe Gly Ala Phe Leu
145                 150                 155                 160

Val Gly

<210> SEQ ID NO 45
<211> LENGTH: 164
<212> TYPE: PRT
<213> ORGANISM: Homo sapiens

<400> SEQUENCE: 45

Gly Pro Gln Arg Val Ala Ala His Ile Thr Gly Thr Arg Gly Arg Ser
1               5                   10                  15

Asn Thr Leu Ser Ser Pro Asn Ser Lys Asn Glu Lys Ala Leu Gly Arg
            20                  25                  30

Lys Ile Asn Ser Trp Glu Ser Ser Arg Ser Gly His Ser Phe Leu Ser
        35                  40                  45

Asn Leu His Leu Arg Asn Gly Glu Leu Val Ile His Glu Lys Gly Phe
 50                  55                  60

Tyr Tyr Ile Tyr Ser Gln Thr Tyr Phe Arg Phe Gln Glu Glu Ile Lys
 65                  70                  75                  80

Glu Asn Thr Lys Asn Asp Lys Gln Met Val Gln Tyr Ile Tyr Lys Tyr
                85                  90                  95

Thr Ser Tyr Pro Asp Pro Ile Leu Leu Met Lys Ser Ala Arg Asn Ser
            100                 105                 110

Cys Trp Ser Lys Asp Ala Glu Tyr Gly Leu Tyr Ser Ile Tyr Gln Gly
            115                 120                 125

Gly Ile Phe Glu Leu Lys Glu Asn Asp Arg Ile Phe Val Ser Val Thr
130                 135                 140

Asn Glu His Leu Ile Asp Met Asp His Glu Ala Ser Phe Phe Gly Ala
145                 150                 155                 160

Phe Leu Val Gly

<210> SEQ ID NO 46
<211> LENGTH: 166
<212> TYPE: PRT
<213> ORGANISM: Homo sapiens

<400> SEQUENCE: 46

Glu Arg Gly Pro Gln Arg Val Ala Ala His Ile Thr Gly Thr Arg Gly
1               5                   10                  15

Arg Ser Asn Thr Leu Ser Ser Pro Asn Ser Lys Asn Glu Lys Ala Leu
            20                  25                  30

```
Gly Arg Lys Ile Asn Ser Trp Glu Ser Ser Arg Ser Gly His Ser Phe
            35                  40                  45

Leu Ser Asn Leu His Leu Arg Asn Gly Glu Leu Val Ile His Glu Lys
 50                  55                  60

Gly Phe Tyr Tyr Ile Tyr Ser Gln Thr Tyr Phe Arg Phe Gln Glu Glu
 65                  70                  75                  80

Ile Lys Glu Asn Thr Lys Asn Asp Lys Gln Met Val Gln Tyr Ile Tyr
                85                  90                  95

Lys Tyr Thr Ser Tyr Pro Asp Pro Ile Leu Leu Met Lys Ser Ala Arg
                100                 105                 110

Asn Ser Cys Trp Ser Lys Asp Ala Glu Tyr Gly Leu Tyr Ser Ile Tyr
                115                 120                 125

Gln Gly Gly Ile Phe Glu Leu Lys Glu Asn Asp Arg Ile Phe Val Ser
            130                 135                 140

Val Thr Asn Glu His Leu Ile Asp Met Asp His Glu Ala Ser Phe Phe
145                 150                 155                 160

Gly Ala Phe Leu Val Gly
                165

<210> SEQ ID NO 47
<211> LENGTH: 168
<212> TYPE: PRT
<213> ORGANISM: Homo sapiens

<400> SEQUENCE: 47

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
                20                  25                  30

Ala Leu Gly Arg Lys Ile Asn Ser Trp Glu Ser Ser Arg Ser Gly His
            35                  40                  45

Ser Phe Leu Ser Asn Leu His Leu Arg Asn Gly Glu Leu Val Ile His
 50                  55                  60

Glu Lys Gly Phe Tyr Tyr Ile Tyr Ser Gln Thr Tyr Phe Arg Phe Gln
 65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
                100                 105                 110

Ala Arg Asn Ser Cys Trp Ser Lys Asp Ala Glu Tyr Gly Leu Tyr Ser
            115                 120                 125

Ile Tyr Gln Gly Gly Ile Phe Glu Leu Lys Glu Asn Asp Arg Ile Phe
            130                 135                 140

Val Ser Val Thr Asn Glu His Leu Ile Asp Met Asp His Glu Ala Ser
145                 150                 155                 160

Phe Phe Gly Ala Phe Leu Val Gly
                165

<210> SEQ ID NO 48
<211> LENGTH: 187
<212> TYPE: PRT
<213> ORGANISM: Homo sapiens

<400> SEQUENCE: 48

Thr Ser Glu Glu Thr Ile Ser Thr Val Gln Glu Lys Gln Gln Asn Ile
1               5                   10                  15
```

```
Ser Pro Leu Val Arg Glu Arg Gly Pro Gln Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
 50                  55                  60

Ser Gly His Ser Phe Leu Ser Asn Leu His Leu Arg Asn Gly Glu Leu
 65                  70                  75                  80

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
            115                 120                 125

Met Lys Ser Ala Arg Asn Ser Cys Trp Ser Lys Asp Ala Glu Tyr Gly
130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185

<210> SEQ ID NO 49
<211> LENGTH: 193
<212> TYPE: PRT
<213> ORGANISM: Mus musculus

<400> SEQUENCE: 49

Thr Phe Gln Asp Thr Ile Ser Thr Val Pro Glu Lys Gln Leu Ser Thr
 1               5                  10                  15

Pro Pro Leu Pro Arg Gly Gly Arg Pro Gln Lys Val Ala Ala His Ile
            20                  25                  30

Thr Gly Ile Thr Arg Arg Ser Asn Ser Ala Leu Ile Pro Ile Ser Lys
        35                  40                  45

Asp Gly Lys Thr Leu Gly Gln Lys Ile Glu Ser Trp Glu Ser Ser Arg
 50                  55                  60

Lys Gly His Ser Phe Leu Asn His Val Leu Phe Arg Asn Gly Glu Leu
 65                  70                  75                  80

Val Ile Glu Gln Glu Gly Leu Tyr Tyr Ile Tyr Ser Gln Thr Tyr Phe
                85                  90                  95

Arg Phe Gln Glu Ala Glu Asp Ala Ser Lys Met Val Ser Lys Asp Lys
            100                 105                 110

Val Arg Thr Lys Gln Leu Val Gln Tyr Ile Tyr Lys Tyr Thr Ser Tyr
            115                 120                 125

Pro Asp Pro Ile Val Leu Met Lys Ser Ala Arg Asn Ser Cys Trp Ser
        130                 135                 140

Arg Asp Ala Glu Tyr Gly Leu Tyr Ser Ile Tyr Gln Gly Gly Leu Phe
145                 150                 155                 160

Glu Leu Lys Lys Asn Asp Arg Ile Phe Val Ser Val Thr Asn Glu His
                165                 170                 175

Leu Met Asp Leu Asp Gln Glu Ala Ser Phe Phe Gly Ala Phe Leu Ile
            180                 185                 190

Asn
```

<210> SEQ ID NO 50
<211> LENGTH: 138
<212> TYPE: PRT
<213> ORGANISM: Homo sapiens

<400> SEQUENCE: 50

Arg Lys Val Ala His Leu Thr Gly Lys Ser Asn Ser Arg Ser Met Pro
1               5                   10                  15

Leu Glu Trp Glu Asp Thr Tyr Gly Ile Val Leu Leu Ser Gly Val Lys
            20                  25                  30

Tyr Lys Lys Gly Gly Leu Val Ile Asn Glu Thr Gly Leu Tyr Phe Val
        35                  40                  45

Tyr Ser Lys Val Tyr Phe Arg Gly Gln Ser Cys Asn Asn Leu Pro Leu
    50                  55                  60

Ser His Lys Val Tyr Met Arg Asn Ser Lys Tyr Pro Gln Asp Leu Val
65                  70                  75                  80

Met Met Glu Gly Lys Met Met Ser Tyr Cys Thr Thr Gly Gln Met Trp
                85                  90                  95

Ala Arg Ser Ser Tyr Leu Gly Ala Val Phe Asn Leu Thr Ser Ala Asp
            100                 105                 110

His Leu Tyr Val Asn Val Ser Glu Leu Ser Leu Val Asn Phe Glu Glu
        115                 120                 125

Ser Gln Thr Phe Phe Gly Leu Tyr Lys Leu
    130                 135

<210> SEQ ID NO 51
<211> LENGTH: 140
<212> TYPE: PRT
<213> ORGANISM: Homo sapiens

<400> SEQUENCE: 51

Glu Leu Arg Lys Val Ala His Leu Thr Gly Lys Ser Asn Ser Arg Ser
1               5                   10                  15

Met Pro Leu Glu Trp Glu Asp Thr Tyr Gly Ile Val Leu Leu Ser Gly
            20                  25                  30

Val Lys Tyr Lys Lys Gly Gly Leu Val Ile Asn Glu Thr Gly Leu Tyr
        35                  40                  45

Phe Val Tyr Ser Lys Val Tyr Phe Arg Gly Gln Ser Cys Asn Asn Leu
    50                  55                  60

Pro Leu Ser His Lys Val Tyr Met Arg Asn Ser Lys Tyr Pro Gln Asp
65                  70                  75                  80

Leu Val Met Met Glu Gly Lys Met Met Ser Tyr Cys Thr Thr Gly Gln
                85                  90                  95

Met Trp Ala Arg Ser Ser Tyr Leu Gly Ala Val Phe Asn Leu Thr Ser
            100                 105                 110

Ala Asp His Leu Tyr Val Asn Val Ser Glu Leu Ser Leu Val Asn Phe
        115                 120                 125

Glu Glu Ser Gln Thr Phe Phe Gly Leu Tyr Lys Leu
    130                 135                 140

<210> SEQ ID NO 52
<211> LENGTH: 145
<212> TYPE: PRT
<213> ORGANISM: Homo sapiens

<400> SEQUENCE: 52

Pro Pro Glu Lys Lys Glu Leu Arg Lys Val Ala His Leu Thr Gly Lys
1               5                   10                  15

Ser Asn Ser Arg Ser Met Pro Leu Glu Trp Glu Asp Thr Tyr Gly Ile
            20                  25                  30

Val Leu Leu Ser Gly Val Lys Tyr Lys Gly Gly Leu Val Ile Asn
        35                  40                  45

Glu Thr Gly Leu Tyr Phe Val Tyr Ser Lys Val Tyr Phe Arg Gly Gln
        50                  55                  60

Ser Cys Asn Asn Leu Pro Leu Ser His Lys Val Tyr Met Arg Asn Ser
65                  70                  75                  80

Lys Tyr Pro Gln Asp Leu Val Met Met Glu Gly Lys Met Met Ser Tyr
            85                  90                  95

Cys Thr Thr Gly Gln Met Trp Ala Arg Ser Ser Tyr Leu Gly Ala Val
            100                 105                 110

Phe Asn Leu Thr Ser Ala Asp His Leu Tyr Val Asn Val Ser Glu Leu
            115                 120                 125

Ser Leu Val Asn Phe Glu Glu Ser Gln Thr Phe Phe Gly Leu Tyr Lys
        130                 135                 140

Leu
145

<210> SEQ ID NO 53
<211> LENGTH: 152
<212> TYPE: PRT
<213> ORGANISM: Homo sapiens

<400> SEQUENCE: 53

Gln Ile Gly His Pro Ser Pro Pro Glu Lys Lys Glu Leu Arg Lys
1               5                   10                  15

Val Ala His Leu Thr Gly Lys Ser Asn Ser Arg Ser Met Pro Leu Glu
            20                  25                  30

Trp Glu Asp Thr Tyr Gly Ile Val Leu Leu Ser Gly Val Lys Tyr Lys
        35                  40                  45

Lys Gly Gly Leu Val Ile Asn Glu Thr Gly Leu Tyr Phe Val Tyr Ser
50                  55                  60

Lys Val Tyr Phe Arg Gly Gln Ser Cys Asn Asn Leu Pro Leu Ser His
65                  70                  75                  80

Lys Val Tyr Met Arg Asn Ser Lys Tyr Pro Gln Asp Leu Val Met Met
            85                  90                  95

Glu Gly Lys Met Met Ser Tyr Cys Thr Thr Gly Gln Met Trp Ala Arg
            100                 105                 110

Ser Ser Tyr Leu Gly Ala Val Phe Asn Leu Thr Ser Ala Asp His Leu
            115                 120                 125

Tyr Val Asn Val Ser Glu Leu Ser Leu Val Asn Phe Glu Glu Ser Gln
        130                 135                 140

Thr Phe Phe Gly Leu Tyr Lys Leu
145                 150

<210> SEQ ID NO 54
<211> LENGTH: 162
<212> TYPE: PRT
<213> ORGANISM: Homo sapiens

<400> SEQUENCE: 54

Gln Met His Thr Ala Ser Ser Leu Glu Lys Gln Ile Gly His Pro Ser
1               5                   10                  15

```
Pro Pro Pro Glu Lys Lys Glu Leu Arg Lys Val Ala His Leu Thr Gly
            20                  25                  30

Lys Ser Asn Ser Arg Ser Met Pro Leu Glu Trp Glu Asp Thr Tyr Gly
        35                  40                  45

Ile Val Leu Leu Ser Gly Val Lys Tyr Lys Lys Gly Gly Leu Val Ile
 50                  55                  60

Asn Glu Thr Gly Leu Tyr Phe Val Tyr Ser Lys Val Tyr Phe Arg Gly
 65                  70                  75                  80

Gln Ser Cys Asn Asn Leu Pro Leu Ser His Lys Val Tyr Met Arg Asn
                85                  90                  95

Ser Lys Tyr Pro Gln Asp Leu Val Met Met Glu Gly Lys Met Met Ser
               100                 105                 110

Tyr Cys Thr Thr Gly Gln Met Trp Ala Arg Ser Ser Tyr Leu Gly Ala
           115                 120                 125

Val Phe Asn Leu Thr Ser Ala Asp His Leu Tyr Val Asn Val Ser Glu
       130                 135                 140

Leu Ser Leu Val Asn Phe Glu Glu Ser Gln Thr Phe Phe Gly Leu Tyr
145                 150                 155                 160

Lys Leu

<210> SEQ ID NO 55
<211> LENGTH: 143
<212> TYPE: PRT
<213> ORGANISM: Mus musculus

<400> SEQUENCE: 55

Glu Lys Lys Glu Pro Arg Ser Val Ala His Leu Thr Gly Asn Pro His
 1               5                  10                  15

Ser Arg Ser Ile Pro Leu Glu Trp Glu Asp Thr Tyr Gly Thr Ala Leu
            20                  25                  30

Ile Ser Gly Val Lys Tyr Lys Lys Gly Gly Leu Val Ile Asn Glu Thr
        35                  40                  45

Gly Leu Tyr Phe Val Tyr Ser Lys Val Tyr Phe Arg Gly Gln Ser Cys
 50                  55                  60

Asn Asn Gln Pro Leu Asn His Lys Val Tyr Met Arg Asn Ser Lys Tyr
65                  70                  75                  80

Pro Glu Asp Leu Val Leu Met Glu Glu Lys Arg Leu Asn Tyr Cys Thr
                85                  90                  95

Thr Gly Gln Ile Trp Ala His Ser Ser Tyr Leu Gly Ala Val Phe Asn
           100                 105                 110

Leu Thr Ser Ala Asp His Leu Tyr Val Asn Ile Ser Gln Leu Ser Leu
       115                 120                 125

Ile Asn Phe Glu Glu Ser Lys Thr Phe Phe Gly Leu Tyr Lys Leu
130                 135                 140

<210> SEQ ID NO 56
<211> LENGTH: 147
<212> TYPE: PRT
<213> ORGANISM: Homo sapiens

<400> SEQUENCE: 56

Ser Asn Leu Lys Pro Ala Ala His Leu Ile Gly Asp Pro Ser Lys Gln
 1               5                  10                  15

Asn Ser Leu Leu Trp Arg Ala Asn Thr Asp Arg Ala Phe Leu Gln Asp
            20                  25                  30

Gly Phe Ser Leu Ser Asn Asn Ser Leu Leu Val Pro Thr Ser Gly Ile
```

```
            35                  40                  45
Tyr Phe Val Tyr Ser Gln Val Val Phe Ser Gly Lys Ala Tyr Ser Pro
 50                  55                  60

Lys Ala Thr Ser Ser Pro Leu Tyr Leu Ala His Glu Val Gln Leu Phe
 65                  70                  75                  80

Ser Ser Gln Tyr Pro Phe His Val Pro Leu Ser Ser Gln Lys Met
                 85                  90                  95

Val Tyr Pro Gly Leu Gln Glu Pro Trp Leu His Ser Met Tyr His Gly
                100                 105                 110

Ala Ala Phe Gln Leu Thr Gln Gly Asp Gln Leu Ser Thr His Thr Asp
                115                 120                 125

Gly Ile Pro His Leu Val Leu Ser Pro Ser Thr Val Phe Phe Gly Ala
                130                 135                 140

Phe Ala Leu
145
```

<210> SEQ ID NO 57
<211> LENGTH: 163
<212> TYPE: PRT
<213> ORGANISM: Homo sapiens

<400> SEQUENCE: 57

```
Asp Leu Ser Pro Gly Leu Pro Ala Ala His Leu Ile Gly Ala Pro Leu
 1               5                  10                  15

Lys Gly Gln Gly Leu Gly Trp Glu Thr Thr Lys Glu Gln Ala Phe Leu
                20                  25                  30

Thr Ser Gly Thr Gln Phe Ser Asp Ala Glu Gly Leu Ala Leu Pro Gln
                35                  40                  45

Asp Gly Leu Tyr Tyr Leu Tyr Cys Leu Val Gly Tyr Arg Gly Arg Ala
 50                  55                  60

Pro Pro Gly Gly Gly Asp Pro Gln Gly Arg Ser Val Thr Leu Arg Ser
 65                  70                  75                  80

Ser Leu Tyr Arg Ala Gly Gly Ala Tyr Gly Pro Gly Thr Pro Glu Leu
                85                  90                  95

Leu Leu Glu Gly Ala Glu Thr Val Thr Pro Val Leu Asp Pro Ala Arg
                100                 105                 110

Arg Gln Gly Tyr Gly Pro Leu Trp Tyr Thr Ser Val Gly Phe Gly Gly
                115                 120                 125

Leu Val Gln Leu Arg Arg Gly Glu Arg Val Tyr Val Asn Ile Ser His
                130                 135                 140

Pro Asp Met Val Asp Phe Ala Arg Gly Lys Thr Phe Phe Gly Ala Val
145                 150                 155                 160

Met Val Gly
```

<210> SEQ ID NO 58
<211> LENGTH: 159
<212> TYPE: PRT
<213> ORGANISM: Homo sapiens

<400> SEQUENCE: 58

```
Gly Leu Pro Ala Ala His Leu Ile Gly Ala Pro Leu Lys Gly Gln Gly
 1               5                  10                  15

Leu Gly Trp Glu Thr Thr Lys Glu Gln Ala Phe Leu Thr Ser Gly Thr
                20                  25                  30

Gln Phe Ser Asp Ala Glu Gly Leu Ala Leu Pro Gln Asp Gly Leu Tyr
                35                  40                  45
```

-continued

Tyr Leu Tyr Cys Leu Val Gly Tyr Arg Gly Arg Ala Pro Pro Gly Gly
    50                  55                  60

Gly Asp Pro Gln Gly Arg Ser Val Thr Leu Arg Ser Ser Leu Tyr Arg
65                  70                  75                  80

Ala Gly Gly Ala Tyr Gly Pro Gly Thr Pro Glu Leu Leu Leu Glu Gly
                85                  90                  95

Ala Glu Thr Val Thr Pro Val Leu Asp Pro Ala Arg Arg Gln Gly Tyr
            100                 105                 110

Gly Pro Leu Trp Tyr Thr Ser Val Gly Phe Gly Leu Val Gln Leu
        115                 120                 125

Arg Arg Gly Glu Arg Val Tyr Val Asn Ile Ser His Pro Asp Met Val
    130                 135                 140

Asp Phe Ala Arg Gly Lys Thr Phe Phe Gly Ala Val Met Val Gly
145                 150                 155

<210> SEQ ID NO 59
<211> LENGTH: 138
<212> TYPE: PRT
<213> ORGANISM: Homo sapiens

<400> SEQUENCE: 59

Lys Ser Trp Ala Tyr Leu Gln Val Ala Lys His Leu Asn Lys Thr Lys
1               5                   10                  15

Leu Ser Trp Asn Lys Asp Gly Ile Leu His Gly Val Arg Tyr Gln Asp
            20                  25                  30

Gly Asn Leu Val Ile Gln Phe Pro Gly Leu Tyr Phe Ile Ile Cys Gln
        35                  40                  45

Leu Gln Phe Leu Val Gln Cys Pro Asn Asn Ser Val Asp Leu Lys Leu
    50                  55                  60

Glu Leu Leu Ile Asn Lys His Ile Lys Lys Gln Ala Leu Val Thr Val
65                  70                  75                  80

Cys Glu Ser Gly Met Gln Thr Lys His Val Tyr Gln Asn Leu Ser Gln
                85                  90                  95

Phe Leu Leu Asp Tyr Leu Gln Val Asn Thr Thr Ile Ser Val Asn Val
            100                 105                 110

Asp Thr Phe Gln Tyr Ile Asp Thr Ser Thr Phe Pro Leu Glu Asn Val
        115                 120                 125

Leu Ser Ile Phe Leu Tyr Ser Asn Ser Asp
    130                 135

<210> SEQ ID NO 60
<211> LENGTH: 133
<212> TYPE: PRT
<213> ORGANISM: Homo sapiens

<400> SEQUENCE: 60

Leu Gln Val Ala Lys His Leu Asn Lys Thr Lys Leu Ser Trp Asn Lys
1               5                   10                  15

Asp Gly Ile Leu His Gly Val Arg Tyr Gln Asp Gly Asn Leu Val Ile
            20                  25                  30

Gln Phe Pro Gly Leu Tyr Phe Ile Ile Cys Gln Leu Gln Phe Leu Val
        35                  40                  45

Gln Cys Pro Asn Asn Ser Val Asp Leu Lys Leu Glu Leu Leu Ile Asn
    50                  55                  60

Lys His Ile Lys Lys Gln Ala Leu Val Thr Val Cys Glu Ser Gly Met
65                  70                  75                  80

Gln Thr Lys His Val Tyr Gln Asn Leu Ser Gln Phe Leu Leu Asp Tyr
                85                  90                  95

Leu Gln Val Asn Thr Thr Ile Ser Val Asn Val Asp Thr Phe Gln Tyr
            100                 105                 110

Ile Asp Thr Ser Thr Phe Pro Leu Glu Asn Val Leu Ser Ile Phe Leu
            115                 120                 125

Tyr Ser Asn Ser Asp
            130

<210> SEQ ID NO 61
<211> LENGTH: 146
<212> TYPE: PRT
<213> ORGANISM: Homo sapiens

<400> SEQUENCE: 61

Gly Asp Gln Asn Pro Gln Ile Ala Ala His Val Ile Ser Glu Ala Ser
1               5                   10                  15

Ser Lys Thr Thr Ser Val Leu Gln Trp Ala Glu Lys Gly Tyr Tyr Thr
            20                  25                  30

Met Ser Asn Asn Leu Val Thr Leu Glu Asn Gly Lys Gln Leu Thr Val
        35                  40                  45

Lys Arg Gln Gly Leu Tyr Tyr Ile Tyr Ala Gln Val Thr Phe Cys Ser
    50                  55                  60

Asn Arg Glu Ala Ser Ser Gln Ala Pro Phe Ile Ala Ser Leu Cys Leu
65                  70                  75                  80

Lys Ser Pro Gly Arg Phe Glu Arg Ile Leu Leu Arg Ala Ala Asn Thr
                85                  90                  95

His Ser Ser Ala Lys Pro Cys Gly Gln Gln Ser Ile His Leu Gly Gly
            100                 105                 110

Val Phe Glu Leu Gln Pro Gly Ala Ser Val Phe Val Asn Val Thr Asp
            115                 120                 125

Pro Ser Gln Val Ser His Gly Thr Gly Phe Thr Ser Phe Gly Leu Leu
            130                 135                 140

Lys Leu
145

<210> SEQ ID NO 62
<211> LENGTH: 149
<212> TYPE: PRT
<213> ORGANISM: Homo sapiens

<400> SEQUENCE: 62

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
            115                 120                 125

Val Thr Asp Pro Ser Gln Val Ser His Gly Thr Gly Phe Thr Ser Phe
        130                 135                 140

Gly Leu Leu Lys Leu
145

<210> SEQ ID NO 63
<211> LENGTH: 132
<212> TYPE: PRT
<213> ORGANISM: Homo sapiens

<400> SEQUENCE: 63

Val Ser His Arg Tyr Pro Arg Ile Gln Ser Ile Lys Val Gln Phe Thr
1               5                   10                  15

Glu Tyr Lys Lys Glu Lys Gly Phe Ile Leu Thr Ser Gln Lys Glu Asp
            20                  25                  30

Glu Ile Met Lys Val Gln Asn Asn Ser Val Ile Ile Asn Cys Asp Gly
        35                  40                  45

Phe Tyr Leu Ile Ser Leu Lys Gly Tyr Phe Ser Gln Glu Val Asn Ile
    50                  55                  60

Ser Leu His Tyr Gln Lys Asp Glu Glu Pro Leu Phe Gln Leu Lys Lys
65                  70                  75                  80

Val Arg Ser Val Asn Ser Leu Met Val Ala Ser Leu Thr Tyr Lys Asp
                85                  90                  95

Lys Val Tyr Leu Asn Val Thr Thr Asp Asn Thr Ser Leu Asp Asp Phe
            100                 105                 110

His Val Asn Gly Gly Glu Leu Ile Leu Ile His Gln Asn Pro Gly Glu
        115                 120                 125

Phe Cys Val Leu
    130

<210> SEQ ID NO 64
<211> LENGTH: 129
<212> TYPE: PRT
<213> ORGANISM: Homo sapiens

<400> SEQUENCE: 64

Arg Tyr Pro Arg Ile Gln Ser Ile Lys Val Gln Phe Thr Glu Tyr Lys
1               5                   10                  15

Lys Glu Lys Gly Phe Ile Leu Thr Ser Gln Lys Glu Asp Glu Ile Met
            20                  25                  30

Lys Val Gln Asn Asn Ser Val Ile Ile Asn Cys Asp Gly Phe Tyr Leu
        35                  40                  45

Ile Ser Leu Lys Gly Tyr Phe Ser Gln Glu Val Asn Ile Ser Leu His
    50                  55                  60

Tyr Gln Lys Asp Glu Glu Pro Leu Phe Gln Leu Lys Lys Val Arg Ser
65                  70                  75                  80

Val Asn Ser Leu Met Val Ala Ser Leu Thr Tyr Lys Asp Lys Val Tyr
                85                  90                  95

Leu Asn Val Thr Thr Asp Asn Thr Ser Leu Asp Asp Phe His Val Asn
            100                 105                 110

Gly Gly Glu Leu Ile Leu Ile His Gln Asn Pro Gly Glu Phe Cys Val
        115                 120                 125

Leu

<210> SEQ ID NO 65
<211> LENGTH: 157
<212> TYPE: PRT
<213> ORGANISM: Homo sapiens

<400> SEQUENCE: 65

```
Glu Ala Gln Pro Phe Ala His Leu Thr Ile Asn Ala Thr Asp Ile Pro
1               5                   10                  15

Ser Gly Ser His Lys Val Ser Leu Ser Ser Trp Tyr His Asp Arg Gly
            20                  25                  30

Trp Ala Lys Ile Ser Asn Met Thr Phe Ser Asn Gly Lys Leu Ile Val
        35                  40                  45

Asn Gln Asp Gly Phe Tyr Tyr Leu Tyr Ala Asn Ile Cys Phe Arg His
    50                  55                  60

His Glu Thr Ser Gly Asp Leu Ala Thr Glu Tyr Leu Gln Leu Met Val
65                  70                  75                  80

Tyr Val Thr Lys Thr Ser Ile Lys Ile Pro Ser Ser His Thr Leu Met
                85                  90                  95

Lys Gly Gly Ser Thr Lys Tyr Trp Ser Gly Asn Ser Glu Phe His Phe
            100                 105                 110

Tyr Ser Ile Asn Val Gly Gly Phe Lys Leu Arg Ser Gly Glu Glu
        115                 120                 125

Ile Ser Ile Glu Val Ser Asn Pro Ser Leu Leu Asp Pro Asp Gln Asp
    130                 135                 140

Ala Thr Tyr Phe Gly Ala Phe Lys Val Arg Asp Ile Asp
145                 150                 155
```

<210> SEQ ID NO 66
<211> LENGTH: 178
<212> TYPE: PRT
<213> ORGANISM: Homo sapiens

<400> SEQUENCE: 66

```
Ile Arg Ala Glu Lys Ala Met Val Asp Gly Ser Trp Leu Asp Leu Ala
1               5                   10                  15

Lys Arg Ser Lys Leu Glu Ala Gln Pro Phe Ala His Leu Thr Ile Asn
            20                  25                  30

Ala Thr Asp Ile Pro Ser Gly Ser His Lys Val Ser Leu Ser Ser Trp
        35                  40                  45

Tyr His Asp Arg Gly Trp Ala Lys Ile Ser Asn Met Thr Phe Ser Asn
    50                  55                  60

Gly Lys Leu Ile Val Asn Gln Asp Gly Phe Tyr Tyr Leu Tyr Ala Asn
65                  70                  75                  80

Ile Cys Phe Arg His His Glu Thr Ser Gly Asp Leu Ala Thr Glu Tyr
                85                  90                  95

Leu Gln Leu Met Val Tyr Val Thr Lys Thr Ser Ile Lys Ile Pro Ser
            100                 105                 110

Ser His Thr Leu Met Lys Gly Gly Ser Thr Lys Tyr Trp Ser Gly Asn
        115                 120                 125

Ser Glu Phe His Phe Tyr Ser Ile Asn Val Gly Gly Phe Phe Lys Leu
    130                 135                 140

Arg Ser Gly Glu Glu Ile Ser Ile Glu Val Ser Asn Pro Ser Leu Leu
145                 150                 155                 160

Asp Pro Asp Gln Asp Ala Thr Tyr Phe Gly Ala Phe Lys Val Arg Asp
                165                 170                 175
```

Ile Asp

<210> SEQ ID NO 67
<211> LENGTH: 156
<212> TYPE: PRT
<213> ORGANISM: Homo sapiens

<400> SEQUENCE: 67

Ser Ala Pro Lys Gly Arg Lys Thr Arg Ala Arg Arg Ala Ile Ala Ala
1               5                   10                  15

His Tyr Glu Val His Pro Arg Pro Gly Gln Asp Gly Ala Gln Ala Gly
            20                  25                  30

Val Asp Gly Thr Val Ser Gly Trp Glu Glu Ala Arg Ile Asn Ser Ser
        35                  40                  45

Ser Pro Leu Arg Tyr Asn Arg Gln Ile Gly Glu Phe Ile Val Thr Arg
    50                  55                  60

Ala Gly Leu Tyr Tyr Leu Tyr Cys Gln Val His Phe Asp Glu Gly Lys
65                  70                  75                  80

Ala Val Tyr Leu Lys Leu Asp Leu Leu Val Asp Gly Val Leu Ala Leu
                85                  90                  95

Arg Cys Leu Glu Glu Phe Ser Ala Thr Ala Ala Ser Ser Leu Gly Pro
            100                 105                 110

Gln Leu Arg Leu Cys Gln Val Ser Gly Leu Leu Ala Leu Arg Pro Gly
        115                 120                 125

Ser Ser Leu Arg Ile Arg Thr Leu Pro Trp Ala His Leu Lys Ala Ala
    130                 135                 140

Pro Phe Leu Thr Tyr Phe Gly Leu Phe Gln Val His
145                 150                 155

<210> SEQ ID NO 68
<211> LENGTH: 145
<212> TYPE: PRT
<213> ORGANISM: Homo sapiens

<400> SEQUENCE: 68

Arg Ala Ile Ala Ala His Tyr Glu Val His Pro Arg Pro Gly Gln Asp
1               5                   10                  15

Gly Ala Gln Ala Gly Val Asp Gly Thr Val Ser Gly Trp Glu Glu Ala
            20                  25                  30

Arg Ile Asn Ser Ser Ser Pro Leu Arg Tyr Asn Arg Gln Ile Gly Glu
        35                  40                  45

Phe Ile Val Thr Arg Ala Gly Leu Tyr Tyr Leu Tyr Cys Gln Val His
    50                  55                  60

Phe Asp Glu Gly Lys Ala Val Tyr Leu Lys Leu Asp Leu Leu Val Asp
65                  70                  75                  80

Gly Val Leu Ala Leu Arg Cys Leu Glu Glu Phe Ser Ala Thr Ala Ala
                85                  90                  95

Ser Ser Leu Gly Pro Gln Leu Arg Leu Cys Gln Val Ser Gly Leu Leu
            100                 105                 110

Ala Leu Arg Pro Gly Ser Ser Leu Arg Ile Arg Thr Leu Pro Trp Ala
        115                 120                 125

His Leu Lys Ala Ala Pro Phe Leu Thr Tyr Phe Gly Leu Phe Gln Val
    130                 135                 140

His
145

-continued

```
<210> SEQ ID NO 69
<211> LENGTH: 158
<212> TYPE: PRT
<213> ORGANISM: Homo sapiens

<400> SEQUENCE: 69

Leu Ile Gln Glu Arg Arg Ser His Glu Val Asn Pro Ala Ala His Leu
1               5                   10                  15

Thr Gly Ala Asn Ser Ser Leu Thr Gly Ser Gly Gly Pro Leu Leu Trp
            20                  25                  30

Glu Thr Gln Leu Gly Leu Ala Phe Leu Arg Gly Leu Ser Tyr His Asp
        35                  40                  45

Gly Ala Leu Val Val Thr Lys Ala Gly Tyr Tyr Ile Tyr Ser Lys
    50                  55                  60

Val Gln Leu Gly Gly Val Gly Cys Pro Leu Gly Leu Ala Ser Thr Ile
65                  70                  75                  80

Thr His Gly Leu Tyr Lys Arg Thr Pro Arg Tyr Pro Glu Glu Leu Glu
                85                  90                  95

Leu Leu Val Ser Gln Gln Ser Pro Cys Gly Arg Ala Thr Ser Ser Ser
            100                 105                 110

Arg Val Trp Trp Asp Ser Ser Phe Leu Gly Gly Val Val His Leu Glu
        115                 120                 125

Ala Gly Glu Lys Val Val Arg Val Leu Asp Glu Arg Leu Val Arg
    130                 135                 140

Leu Arg Asp Gly Thr Arg Ser Tyr Phe Gly Ala Phe Met Val
145                 150                 155

<210> SEQ ID NO 70
<211> LENGTH: 143
<212> TYPE: PRT
<213> ORGANISM: Homo sapiens

<400> SEQUENCE: 70

Glu Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile
        35                  40                  45

His Arg Asp Gly Ile Tyr Met Val His Ile Gln Val Thr Leu Ala Ile
    50                  55                  60

Cys Ser Ser Thr Thr Ala Ser Arg His His Pro Thr Thr Leu Ala Val
65                  70                  75                  80

Gly Ile Cys Ser Pro Ala Ser Arg Ser Ile Ser Leu Leu Arg Leu Ser
                85                  90                  95

Phe His Gln Gly Cys Thr Ile Ala Ser Gln Arg Leu Thr Pro Leu Ala
            100                 105                 110

Arg Gly Asp Thr Leu Cys Thr Asn Leu Thr Gly Thr Leu Leu Pro Ser
        115                 120                 125

Arg Asn Thr Asp Glu Thr Phe Phe Gly Val Gln Trp Val Arg Pro
    130                 135                 140

<210> SEQ ID NO 71
<211> LENGTH: 138
<212> TYPE: PRT
<213> ORGANISM: Homo sapiens

<400> SEQUENCE: 71
```

```
Asp Val Ala Glu Leu Gln Leu Asn His Thr Gly Pro Gln Gln Asp Pro
1               5                   10                  15

Arg Leu Tyr Trp Gln Gly Pro Ala Leu Gly Arg Ser Phe Leu His
            20                  25                  30

Gly Pro Glu Leu Asp Lys Gly Gln Leu Arg Ile His Arg Asp Gly Ile
                35                  40                  45

Tyr Met Val His Ile Gln Val Thr Leu Ala Ile Cys Ser Ser Thr Thr
        50                  55                  60

Ala Ser Arg His His Pro Thr Thr Leu Ala Val Gly Ile Cys Ser Pro
65                  70                  75                  80

Ala Ser Arg Ser Ile Ser Leu Leu Arg Leu Ser Phe His Gln Gly Cys
                85                  90                  95

Thr Ile Ala Ser Gln Arg Leu Thr Pro Leu Ala Arg Gly Asp Thr Leu
            100                 105                 110

Cys Thr Asn Leu Thr Gly Thr Leu Leu Pro Ser Arg Asn Thr Asp Glu
            115                 120                 125

Thr Phe Phe Gly Val Gln Trp Val Arg Pro
            130                 135
```

<210> SEQ ID NO 72
<211> LENGTH: 170
<212> TYPE: PRT
<213> ORGANISM: Homo sapiens

<400> SEQUENCE: 72

```
Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
                35                  40                  45

Leu Val Val Ala Lys Ala Gly Val Tyr Tyr Val Phe Phe Gln Leu Glu
        50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
            115                 120                 125

Gly Val His Leu His Thr Glu Ala Arg Ala Arg His Ala Trp Gln Leu
            130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170
```

<210> SEQ ID NO 73
<211> LENGTH: 128
<212> TYPE: PRT
<213> ORGANISM: Homo sapiens

<400> SEQUENCE: 73

```
Gln Leu Glu Thr Ala Lys Glu Pro Cys Met Ala Lys Phe Gly Pro Leu
1               5                   10                  15
```

```
Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
            35                  40                  45

Tyr Gly Gln Val Ala Pro Asn Ala Asn Tyr Asn Asp Val Ala Pro Phe
 50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
            115                 120                 125
```

<210> SEQ ID NO 74
<211> LENGTH: 139
<212> TYPE: PRT
<213> ORGANISM: Homo sapiens

<400> SEQUENCE: 74

```
Lys Lys Gln His Ser Val Leu His Leu Val Pro Ile Asn Ala Thr Ser
1               5                   10                  15

Lys Asp Asp Ser Asp Val Thr Glu Val Met Trp Gln Pro Ala Leu Arg
            20                  25                  30

Arg Gly Arg Gly Leu Gln Ala Gln Gly Tyr Gly Val Arg Ile Gln Asp
            35                  40                  45

Ala Gly Val Tyr Leu Leu Tyr Ser Gln Val Leu Phe Gln Asp Val Thr
 50                  55                  60

Phe Thr Met Gly Gln Val Val Ser Arg Glu Gly Gln Gly Arg Gln Glu
65                  70                  75                  80

Thr Leu Phe Arg Cys Ile Arg Ser Met Pro Ser His Pro Asp Arg Ala
                85                  90                  95

Tyr Asn Ser Cys Tyr Ser Ala Gly Val Phe His Leu His Gln Gly Asp
            100                 105                 110

Ile Leu Ser Val Ile Ile Pro Arg Ala Arg Ala Lys Leu Asn Leu Ser
            115                 120                 125

Pro His Gly Thr Phe Leu Gly Phe Val Lys Leu
            130                 135
```

<210> SEQ ID NO 75
<211> LENGTH: 147
<212> TYPE: PRT
<213> ORGANISM: Homo sapiens

<400> SEQUENCE: 75

```
Glu Asn Gln Pro Ala Val Val His Leu Gln Gly Gln Gly Ser Ala Ile
1               5                   10                  15

Gln Val Lys Asn Asp Leu Ser Gly Gly Val Leu Asn Asp Trp Ser Arg
            20                  25                  30

Ile Thr Met Asn Pro Lys Val Phe Lys Leu His Pro Arg Ser Gly Glu
            35                  40                  45

Leu Glu Val Leu Val Asp Gly Thr Tyr Phe Ile Tyr Ser Gln Val Glu
 50                  55                  60

Val Tyr Tyr Ile Asn Phe Thr Asp Phe Ala Ser Tyr Glu Val Val Val
65                  70                  75                  80
```

```
Asp Glu Lys Pro Phe Leu Gln Cys Thr Arg Ser Ile Glu Thr Gly Lys
                85                  90                  95

Thr Asn Tyr Asn Thr Cys Tyr Thr Ala Gly Val Cys Leu Leu Lys Ala
            100                 105                 110

Arg Gln Lys Ile Ala Val Lys Met Val His Ala Asp Ile Ser Ile Asn
        115                 120                 125

Met Ser Lys His Thr Thr Phe Phe Gly Ala Ile Arg Leu Gly Glu Ala
    130                 135                 140

Pro Ala Ser
145

<210> SEQ ID NO 76
<211> LENGTH: 145
<212> TYPE: PRT
<213> ORGANISM: Homo sapiens

<400> SEQUENCE: 76

Glu Asn Gln Pro Ala Val Val His Leu Gln Gly Gln Gly Ser Ala Ile
1               5                   10                  15

Gln Val Lys Asn Asp Leu Ser Gly Gly Val Leu Asn Asp Trp Ser Arg
            20                  25                  30

Ile Thr Met Asn Pro Lys Val Phe Lys Leu His Pro Arg Ser Gly Glu
        35                  40                  45

Leu Glu Val Leu Val Asp Gly Thr Tyr Phe Ile Tyr Ser Gln Val Tyr
    50                  55                  60

Tyr Ile Asn Phe Thr Asp Phe Ala Ser Tyr Glu Val Val Val Asp Glu
65                  70                  75                  80

Lys Pro Phe Leu Gln Cys Thr Arg Ser Ile Glu Thr Gly Lys Thr Asn
                85                  90                  95

Tyr Asn Thr Cys Tyr Thr Ala Gly Val Cys Leu Leu Lys Ala Arg Gln
            100                 105                 110

Lys Ile Ala Val Lys Met Val His Ala Asp Ile Ser Ile Asn Met Ser
        115                 120                 125

Lys His Thr Thr Phe Phe Gly Ala Ile Arg Leu Gly Glu Ala Pro Ala
    130                 135                 140

Ser
145

<210> SEQ ID NO 77
<211> LENGTH: 180
<212> TYPE: PRT
<213> ORGANISM: Homo sapiens

<400> SEQUENCE: 77

Leu Lys Gly Gln Glu Phe Ala Pro Ser His Gln Gln Val Tyr Ala Pro
1               5                   10                  15

Leu Arg Ala Asp Gly Asp Lys Pro Arg Ala His Leu Thr Val Val Arg
            20                  25                  30

Gln Thr Pro Thr Gln His Phe Lys Asn Gln Phe Pro Ala Leu His Trp
        35                  40                  45

Glu His Glu Leu Gly Leu Ala Phe Thr Lys Asn Arg Met Asn Tyr Thr
    50                  55                  60

Asn Lys Phe Leu Leu Ile Pro Glu Ser Gly Asp Tyr Phe Ile Tyr Ser
65                  70                  75                  80

Gln Val Thr Phe Arg Gly Met Thr Ser Glu Cys Ser Glu Ile Arg Gln
                85                  90                  95
```

```
Ala Gly Arg Pro Asn Lys Pro Asp Ser Ile Thr Val Ile Thr Lys
            100                 105                 110
Val Thr Asp Ser Tyr Pro Glu Pro Thr Gln Leu Leu Met Gly Thr Lys
115                 120                 125
Ser Val Cys Glu Val Gly Ser Asn Trp Phe Gln Pro Ile Tyr Leu Gly
    130                 135                 140
Ala Met Phe Ser Leu Gln Glu Gly Asp Lys Leu Met Val Asn Val Ser
145                 150                 155                 160
Asp Ile Ser Leu Val Asp Tyr Thr Lys Glu Asp Lys Thr Phe Phe Gly
                165                 170                 175
Ala Phe Leu Leu
            180

<210> SEQ ID NO 78
<211> LENGTH: 159
<212> TYPE: PRT
<213> ORGANISM: Homo sapiens

<400> SEQUENCE: 78

Asp Lys Pro Arg Ala His Leu Thr Val Val Arg Gln Thr Pro Thr Gln
1               5                   10                  15
His Phe Lys Asn Gln Phe Pro Ala Leu His Trp Glu His Glu Leu Gly
            20                  25                  30
Leu Ala Phe Thr Lys Asn Arg Met Asn Tyr Thr Asn Lys Phe Leu Leu
        35                  40                  45
Ile Pro Glu Ser Gly Asp Tyr Phe Ile Tyr Ser Gln Val Thr Phe Arg
    50                  55                  60
Gly Met Thr Ser Glu Cys Ser Glu Ile Arg Gln Ala Gly Arg Pro Asn
65                  70                  75                  80
Lys Pro Asp Ser Ile Thr Val Val Ile Thr Lys Val Thr Asp Ser Tyr
                85                  90                  95
Pro Glu Pro Thr Gln Leu Leu Met Gly Thr Lys Ser Val Cys Glu Val
            100                 105                 110
Gly Ser Asn Trp Phe Gln Pro Ile Tyr Leu Gly Ala Met Phe Ser Leu
        115                 120                 125
Gln Glu Gly Asp Lys Leu Met Val Asn Val Ser Asp Ile Ser Leu Val
    130                 135                 140
Asp Tyr Thr Lys Glu Asp Lys Thr Phe Phe Gly Ala Phe Leu Leu
145                 150                 155

<210> SEQ ID NO 79
<211> LENGTH: 152
<212> TYPE: PRT
<213> ORGANISM: Homo sapiens

<400> SEQUENCE: 79

Ala Val Gln Gly Pro Glu Glu Thr Val Thr Gln Asp Cys Leu Gln Leu
1               5                   10                  15
Ile Ala Asp Ser Glu Thr Pro Thr Ile Gln Lys Gly Ser Tyr Thr Phe
            20                  25                  30
Val Pro Trp Leu Leu Ser Phe Lys Arg Gly Ser Ala Leu Glu Glu Lys
        35                  40                  45
Glu Asn Lys Ile Leu Val Lys Glu Thr Gly Tyr Phe Phe Ile Tyr Gly
    50                  55                  60
Gln Val Leu Tyr Thr Asp Lys Thr Tyr Ala Met Gly His Leu Ile Gln
65                  70                  75                  80
```

```
Arg Lys Lys Val His Val Phe Gly Asp Glu Leu Ser Leu Val Thr Leu
                85                  90                  95

Phe Arg Cys Ile Gln Asn Met Pro Glu Thr Leu Pro Asn Asn Ser Cys
            100                 105                 110

Tyr Ser Ala Gly Ile Ala Lys Leu Glu Glu Gly Asp Glu Leu Gln Leu
        115                 120                 125

Ala Ile Pro Arg Glu Asn Ala Gln Ile Ser Leu Asp Gly Asp Val Thr
130                 135                 140

Phe Phe Gly Ala Leu Lys Leu Leu
145                 150

<210> SEQ ID NO 80
<211> LENGTH: 154
<212> TYPE: PRT
<213> ORGANISM: Homo sapiens

<400> SEQUENCE: 80

Ser Ser Arg Thr Pro Ser Asp Lys Pro Val Ala His Val Val Ala Asn
1               5                   10                  15

Pro Gln Ala Glu Gly Gln Leu Gln Trp Leu Asn Arg Arg Ala Asn Ala
            20                  25                  30

Leu Leu Ala Asn Gly Val Glu Leu Arg Asp Asn Gln Leu Val Val Pro
        35                  40                  45

Ser Glu Gly Leu Tyr Leu Ile Tyr Ser Gln Val Leu Phe Lys Gly Gln
    50                  55                  60

Gly Cys Pro Ser Thr His Val Leu Leu Thr His Thr Ile Ser Arg Ile
65                  70                  75                  80

Ala Val Ser Tyr Gln Thr Lys Val Asn Leu Leu Ser Ala Ile Lys Ser
                85                  90                  95

Pro Cys Gln Arg Glu Thr Pro Glu Gly Ala Glu Ala Lys Pro Trp Tyr
            100                 105                 110

Glu Pro Ile Tyr Leu Gly Gly Val Phe Gln Leu Glu Lys Gly Asp Arg
        115                 120                 125

Leu Ser Ala Glu Ile Asn Arg Pro Asp Tyr Leu Asn Phe Arg Glu Ser
130                 135                 140

Gly Gln Val Tyr Phe Gly Ile Ile Ala Leu
145                 150

<210> SEQ ID NO 81
<211> LENGTH: 472
<212> TYPE: PRT
<213> ORGANISM: Artificial Sequence
<220> FEATURE:
<223> OTHER INFORMATION: scTNFR2

<400> SEQUENCE: 81

Ser Ser Arg Thr Pro Ser Asp Lys Pro Val Ala His Val Val Ala Asn
1               5                   10                  15

Pro Gln Ala Glu Gly Gln Leu Gln Trp Leu Asn Arg Arg Ala Asn Ala
            20                  25                  30

Leu Leu Ala Asn Gly Val Glu Leu Arg Asp Asn Gln Leu Val Val Pro
        35                  40                  45

Ser Glu Gly Leu Tyr Leu Ile Tyr Ser Gln Val Leu Phe Lys Gly Gln
    50                  55                  60

Gly Cys Pro Ser Thr His Val Leu Leu Thr His Thr Ile Ser Arg Ile
65                  70                  75                  80
```

```
Ala Val Ser Tyr Gln Thr Lys Val Asn Leu Ser Ala Ile Lys Ser
                85                  90                  95

Pro Cys Gln Arg Glu Thr Pro Glu Gly Ala Glu Ala Lys Pro Trp Tyr
            100                 105                 110

Glu Pro Ile Tyr Leu Gly Gly Val Phe Gln Leu Glu Lys Gly Asp Arg
            115                 120                 125

Leu Ser Ala Glu Ile Asn Arg Pro Asp Tyr Leu Asn Phe Arg Glu Ser
130                 135                 140

Gly Gln Val Tyr Phe Gly Ile Ile Ala Leu Gly Gly Gly Ser Ser
145                 150                 155                 160

Ser Arg Thr Pro Ser Asp Lys Pro Val Ala His Val Val Ala Asn Pro
                165                 170                 175

Gln Ala Glu Gly Gln Leu Gln Trp Leu Asn Arg Arg Ala Asn Ala Leu
            180                 185                 190

Leu Ala Asn Gly Val Glu Leu Arg Asp Asn Gln Leu Val Val Pro Ser
            195                 200                 205

Glu Gly Leu Tyr Leu Ile Tyr Ser Gln Val Leu Phe Lys Gly Gln Gly
        210                 215                 220

Cys Pro Ser Thr His Val Leu Leu Thr His Thr Ile Ser Arg Ile Ala
225                 230                 235                 240

Val Ser Tyr Gln Thr Lys Val Asn Leu Leu Ser Ala Ile Lys Ser Pro
                245                 250                 255

Cys Gln Arg Glu Thr Pro Glu Gly Ala Glu Ala Lys Pro Trp Tyr Glu
            260                 265                 270

Pro Ile Tyr Leu Gly Gly Val Phe Gln Leu Glu Lys Gly Asp Arg Leu
            275                 280                 285

Ser Ala Glu Ile Asn Arg Pro Asp Tyr Leu Asn Phe Arg Glu Ser Gly
            290                 295                 300

Gln Val Tyr Phe Gly Ile Ile Ala Leu Gly Gly Gly Ser Ser Ser
305                 310                 315                 320

Arg Thr Pro Ser Asp Lys Pro Val Ala His Val Val Ala Asn Pro Gln
                325                 330                 335

Ala Glu Gly Gln Leu Gln Trp Leu Asn Arg Arg Ala Asn Ala Leu Leu
            340                 345                 350

Ala Asn Gly Val Glu Leu Arg Asp Asn Gln Leu Val Val Pro Ser Glu
            355                 360                 365

Gly Leu Tyr Leu Ile Tyr Ser Gln Val Leu Phe Lys Gly Gln Gly Cys
        370                 375                 380

Pro Ser Thr His Val Leu Leu Thr His Thr Ile Ser Arg Ile Ala Val
385                 390                 395                 400

Ser Tyr Gln Thr Lys Val Asn Leu Leu Ser Ala Ile Lys Ser Pro Cys
            405                 410                 415

Gln Arg Glu Thr Pro Glu Gly Ala Glu Ala Lys Pro Trp Tyr Glu Pro
            420                 425                 430

Ile Tyr Leu Gly Gly Val Phe Gln Leu Glu Lys Gly Asp Arg Leu Ser
            435                 440                 445

Ala Glu Ile Asn Arg Pro Asp Tyr Leu Asn Phe Arg Glu Ser Gly Gln
450                 455                 460

Val Tyr Phe Gly Ile Ile Ala Leu
465                 470

<210> SEQ ID NO 82
<211> LENGTH: 227
<212> TYPE: PRT
```

<213> ORGANISM: Homo sapiens

<400> SEQUENCE: 82

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 83
<211> LENGTH: 226
<212> TYPE: PRT
<213> ORGANISM: Homo sapiens

<400> SEQUENCE: 83

```
Asp Lys Thr His Thr Cys Pro Pro Cys Pro Ala Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Gly Leu Pro Ser Ser Ile Glu
            100                 105                 110

Lys Thr Ile Ser Lys Ala Lys Gly Gln Pro Arg Glu Pro Gln Val Tyr
```

```
                115                 120                 125
Thr Leu Pro Pro Ser Arg Asp Glu Leu Thr Lys Asn Gln Val Ser Leu
        130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Gly
225

<210> SEQ ID NO 84
<211> LENGTH: 40
<212> TYPE: PRT
<213> ORGANISM: Homo sapiens

<400> SEQUENCE: 84

Lys Lys Pro Leu Asp Gly Glu Tyr Phe Thr Leu Gln Ile Arg Gly Arg
1               5                   10                  15

Glu Arg Phe Glu Met Phe Arg Glu Leu Asn Glu Ala Leu Glu Leu Lys
            20                  25                  30

Asp Ala Gln Ala Gly Lys Glu Pro
        35                  40

<210> SEQ ID NO 85
<211> LENGTH: 33
<212> TYPE: PRT
<213> ORGANISM: Saccharomyces cerevisiae

<400> SEQUENCE: 85

Arg Leu Lys Gln Ile Glu Asp Lys Leu Glu Glu Ile Leu Ser Lys Leu
1               5                   10                  15

Tyr His Ile Glu Asn Glu Leu Ala Arg Ile Lys Lys Leu Leu Gly Glu
            20                  25                  30

Arg

<210> SEQ ID NO 86
<211> LENGTH: 45
<212> TYPE: PRT
<213> ORGANISM: Homo sapiens

<400> SEQUENCE: 86

Pro Ser Ser Ser Asp Tyr Ser Asp Leu Gln Arg Val Lys Gln Glu Leu
1               5                   10                  15

Leu Glu Glu Val Lys Lys Glu Leu Gln Lys Val Lys Glu Glu Ile Ile
            20                  25                  30

Glu Ala Phe Val Gln Glu Leu Arg Lys Arg Gly Ser Pro
        35                  40                  45

<210> SEQ ID NO 87
<211> LENGTH: 1190
<212> TYPE: PRT
<213> ORGANISM: Artificial Sequence
<220> FEATURE:
```

<223> OTHER INFORMATION: scTNFR2-Fc-scTNFR2

<400> SEQUENCE: 87

```
Ser Ser Arg Thr Pro Ser Asp Lys Pro Val Ala His Val Val Ala Asn
1               5                   10                  15

Pro Gln Ala Glu Gly Gln Leu Gln Trp Leu Asn Arg Arg Ala Asn Ala
            20                  25                  30

Leu Leu Ala Asn Gly Val Glu Leu Arg Asp Asn Gln Leu Val Val Pro
        35                  40                  45

Ser Glu Gly Leu Tyr Leu Ile Tyr Ser Gln Val Leu Phe Lys Gly Gln
    50                  55                  60

Gly Cys Pro Ser Thr His Val Leu Leu Thr His Thr Ile Ser Arg Ile
65                  70                  75                  80

Ala Val Ser Tyr Gln Thr Lys Val Asn Leu Leu Ser Ala Ile Lys Ser
                85                  90                  95

Pro Cys Gln Arg Glu Thr Pro Glu Gly Ala Glu Ala Lys Pro Trp Tyr
            100                 105                 110

Glu Pro Ile Tyr Leu Gly Gly Val Phe Gln Leu Glu Lys Gly Asp Arg
        115                 120                 125

Leu Ser Ala Glu Ile Asn Arg Pro Asp Tyr Leu Asn Phe Arg Glu Ser
    130                 135                 140

Gly Gln Val Tyr Phe Gly Ile Ile Ala Leu Gly Gly Gly Ser Ser
145                 150                 155                 160

Ser Arg Thr Pro Ser Asp Lys Pro Val Ala His Val Val Ala Asn Pro
                165                 170                 175

Gln Ala Glu Gly Gln Leu Gln Trp Leu Asn Arg Arg Ala Asn Ala Leu
            180                 185                 190

Leu Ala Asn Gly Val Glu Leu Arg Asp Asn Gln Leu Val Val Pro Ser
        195                 200                 205

Glu Gly Leu Tyr Leu Ile Tyr Ser Gln Val Leu Phe Lys Gly Gln Gly
    210                 215                 220

Cys Pro Ser Thr His Val Leu Leu Thr His Thr Ile Ser Arg Ile Ala
225                 230                 235                 240

Val Ser Tyr Gln Thr Lys Val Asn Leu Leu Ser Ala Ile Lys Ser Pro
                245                 250                 255

Cys Gln Arg Glu Thr Pro Glu Gly Ala Glu Ala Lys Pro Trp Tyr Glu
            260                 265                 270

Pro Ile Tyr Leu Gly Gly Val Phe Gln Leu Glu Lys Gly Asp Arg Leu
        275                 280                 285

Ser Ala Glu Ile Asn Arg Pro Asp Tyr Leu Asn Phe Arg Glu Ser Gly
    290                 295                 300

Gln Val Tyr Phe Gly Ile Ile Ala Leu Gly Gly Gly Ser Ser Ser
305                 310                 315                 320

Arg Thr Pro Ser Asp Lys Pro Val Ala His Val Val Ala Asn Pro Gln
                325                 330                 335

Ala Glu Gly Gln Leu Gln Trp Leu Asn Arg Arg Ala Asn Ala Leu Leu
            340                 345                 350

Ala Asn Gly Val Glu Leu Arg Asp Asn Gln Leu Val Val Pro Ser Glu
        355                 360                 365

Gly Leu Tyr Leu Ile Tyr Ser Gln Val Leu Phe Lys Gly Gln Gly Cys
    370                 375                 380

Pro Ser Thr His Val Leu Leu Thr His Thr Ile Ser Arg Ile Ala Val
385                 390                 395                 400
```

```
Ser Tyr Gln Thr Lys Val Asn Leu Leu Ser Ala Ile Lys Ser Pro Cys
            405                 410                 415

Gln Arg Glu Thr Pro Glu Gly Ala Glu Ala Lys Pro Trp Tyr Glu Pro
        420                 425                 430

Ile Tyr Leu Gly Gly Val Phe Gln Leu Glu Lys Gly Asp Arg Leu Ser
            435                 440                 445

Ala Glu Ile Asn Arg Pro Asp Tyr Leu Asn Phe Arg Glu Ser Gly Gln
    450                 455                 460

Val Tyr Phe Gly Ile Ile Ala Leu Gly Gly Ser Gly Gly Gly Gly Ser
465                 470                 475                 480

Gly Gly Asp Lys Thr His Thr Cys Pro Pro Cys Pro Ala Pro Pro Val
            485                 490                 495

Ala Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
            515                 520                 525

His Glu Asp Pro Glu Val Lys Phe Asn Trp Tyr Val Asp Gly Val Glu
    530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
            565                 570                 575

Gly Lys Glu Tyr Lys Cys Lys Val Ser Asn Lys Gly Leu Pro Ser Ser
            580                 585                 590

Ile Glu Lys Thr Ile Ser Lys Ala Lys Gly Gln Pro Arg Glu Pro Gln
            595                 600                 605

Val Tyr Thr Leu Pro Pro Ser Arg Asp Glu Leu Thr Lys Asn Gln Val
    610                 615                 620

Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
            645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
            675                 680                 685

Met His Glu Ala Leu His Asn His Tyr Thr Gln Lys Ser Leu Ser Leu
    690                 695                 700

Ser Pro Gly Gly Gly Gly Ser Gly Gly Gly Ser Ser Gly Gly Ser Ser
705                 710                 715                 720

Arg Thr Pro Ser Asp Lys Pro Val Ala His Val Val Ala Asn Pro Gln
            725                 730                 735

Ala Glu Gly Gln Leu Gln Trp Leu Asn Arg Arg Ala Asn Ala Leu Leu
            740                 745                 750

Ala Asn Gly Val Glu Leu Arg Asp Asn Gln Leu Val Val Pro Ser Glu
            755                 760                 765

Gly Leu Tyr Leu Ile Tyr Ser Gln Val Leu Phe Lys Gly Gln Gly Cys
            770                 775                 780

Pro Ser Thr His Val Leu Leu Thr His Thr Ile Ser Arg Ile Ala Val
785                 790                 795                 800

Ser Tyr Gln Thr Lys Val Asn Leu Leu Ser Ala Ile Lys Ser Pro Cys
            805                 810                 815

Gln Arg Glu Thr Pro Glu Gly Ala Glu Ala Lys Pro Trp Tyr Glu Pro
```

```
                820                 825                 830
Ile Tyr Leu Gly Gly Val Phe Gln Leu Glu Lys Gly Asp Arg Leu Ser
            835                 840                 845
Ala Glu Ile Asn Arg Pro Asp Tyr Leu Asn Phe Arg Glu Ser Gly Gln
        850                 855                 860
Val Tyr Phe Gly Ile Ile Ala Leu Gly Gly Gly Ser Ser Ser Arg
865                 870                 875                 880
Thr Pro Ser Asp Lys Pro Val Ala His Val Val Ala Asn Pro Gln Ala
                885                 890                 895
Glu Gly Gln Leu Gln Trp Leu Asn Arg Arg Ala Asn Ala Leu Leu Ala
            900                 905                 910
Asn Gly Val Glu Leu Arg Asp Asn Gln Leu Val Val Pro Ser Glu Gly
        915                 920                 925
Leu Tyr Leu Ile Tyr Ser Gln Val Leu Phe Lys Gly Gln Gly Cys Pro
    930                 935                 940
Ser Thr His Val Leu Leu Thr His Thr Ile Ser Arg Ile Ala Val Ser
945                 950                 955                 960
Tyr Gln Thr Lys Val Asn Leu Leu Ser Ala Ile Lys Ser Pro Cys Gln
                965                 970                 975
Arg Glu Thr Pro Glu Gly Ala Glu Ala Lys Pro Trp Tyr Glu Pro Ile
            980                 985                 990
Tyr Leu Gly Gly Val Phe Gln Leu  Glu Lys Gly Asp Arg  Leu Ser Ala
        995                 1000                1005
Glu Ile  Asn Arg Pro Asp Tyr  Leu Asn Phe Arg Glu  Ser Gly Gln
    1010                1015                1020
Val Tyr  Phe Gly Ile Ile Ala  Leu Gly Gly Gly  Ser Ser Ser
    1025                1030                1035
Arg Thr  Pro Ser Asp Lys  Pro Val Ala His Val Val  Ala Asn Pro
    1040                1045                1050
Gln Ala  Glu Gly Gln Leu Gln  Trp Leu Asn Arg Arg  Ala Asn Ala
    1055                1060                1065
Leu Leu  Ala Asn Gly Val Glu  Leu Arg Asp Asn Gln  Leu Val Val
    1070                1075                1080
Pro Ser  Glu Gly Leu Tyr Leu  Ile Tyr Ser Gln Val  Leu Phe Lys
    1085                1090                1095
Gly Gln  Gly Cys Pro Ser Thr  His Val Leu Leu Thr  His Thr Ile
    1100                1105                1110
Ser Arg  Ile Ala Val Ser Tyr  Gln Thr Lys Val Asn  Leu Leu Ser
    1115                1120                1125
Ala Ile  Lys Ser Pro Cys Gln  Arg Glu Thr Pro Glu  Gly Ala Glu
    1130                1135                1140
Ala Lys  Pro Trp Tyr Glu Pro  Ile Tyr Leu Gly Gly  Val Phe Gln
    1145                1150                1155
Leu Glu  Lys Gly Asp Arg Leu  Ser Ala Glu Ile Asn  Arg Pro Asp
    1160                1165                1170
Tyr Leu  Asn Phe Arg Glu Ser  Gly Gln Val Tyr Phe  Gly Ile Ile
    1175                1180                1185
Ala Leu
    1190

<210> SEQ ID NO 88
<211> LENGTH: 542
<212> TYPE: PRT
<213> ORGANISM: Artificial Sequence
```

<220> FEATURE:
<223> OTHER INFORMATION: p53-scTNFR2

<400> SEQUENCE: 88

Lys Lys Pro Leu Asp Gly Glu Tyr Phe Thr Leu Gln Ile Arg Gly Arg
1               5                   10                  15

Glu Arg Phe Glu Met Phe Arg Glu Leu Asn Glu Ala Leu Glu Leu Lys
            20                  25                  30

Asp Ala Gln Ala Gly Lys Glu Pro Gly Ala Pro Gly Gly Ser Gly
        35                  40                  45

Gly Gly Ser Gly Gly Gly Ser Gly Gly Gly Ser Gly Gly Gly Ser Gly
50                  55                  60

Gly Ser Glu Phe Leu Ala Ser Ser Arg Thr Pro Ser Asp Lys Pro Val
65                  70                  75                  80

Ala His Val Val Ala Asn Pro Gln Ala Glu Gly Gln Leu Gln Trp Leu
                85                  90                  95

Asn Arg Arg Ala Asn Ala Leu Leu Ala Asn Gly Val Glu Leu Arg Asp
            100                 105                 110

Asn Gln Leu Val Val Pro Ser Glu Gly Leu Tyr Leu Ile Tyr Ser Gln
        115                 120                 125

Val Leu Phe Lys Gly Gln Gly Cys Pro Ser Thr His Val Leu Leu Thr
130                 135                 140

His Thr Ile Ser Arg Ile Ala Val Ser Tyr Gln Thr Lys Val Asn Leu
145                 150                 155                 160

Leu Ser Ala Ile Lys Ser Pro Cys Gln Arg Glu Thr Pro Glu Gly Ala
                165                 170                 175

Glu Ala Lys Pro Trp Tyr Glu Pro Ile Tyr Leu Gly Gly Val Phe Gln
            180                 185                 190

Leu Glu Lys Gly Asp Arg Leu Ser Ala Glu Ile Asn Arg Pro Asp Tyr
        195                 200                 205

Leu Asn Phe Arg Glu Ser Gly Gln Val Tyr Phe Gly Ile Ile Ala Leu
210                 215                 220

Gly Gly Gly Gly Ser Ser Arg Thr Pro Ser Asp Lys Pro Val Ala
225                 230                 235                 240

His Val Val Ala Asn Pro Gln Ala Glu Gly Gln Leu Gln Trp Leu Asn
                245                 250                 255

Arg Arg Ala Asn Ala Leu Leu Ala Asn Gly Val Glu Leu Arg Asp Asn
            260                 265                 270

Gln Leu Val Val Pro Ser Glu Gly Leu Tyr Leu Ile Tyr Ser Gln Val
        275                 280                 285

Leu Phe Lys Gly Gln Gly Cys Pro Ser Thr His Val Leu Leu Thr His
290                 295                 300

Thr Ile Ser Arg Ile Ala Val Ser Tyr Gln Thr Lys Val Asn Leu Leu
305                 310                 315                 320

Ser Ala Ile Lys Ser Pro Cys Gln Arg Glu Thr Pro Glu Gly Ala Glu
                325                 330                 335

Ala Lys Pro Trp Tyr Glu Pro Ile Tyr Leu Gly Gly Val Phe Gln Leu
            340                 345                 350

Glu Lys Gly Asp Arg Leu Ser Ala Glu Ile Asn Arg Pro Asp Tyr Leu
        355                 360                 365

Asn Phe Arg Glu Ser Gly Gln Val Tyr Phe Gly Ile Ile Ala Leu Gly
370                 375                 380

Gly Gly Gly Ser Ser Arg Thr Pro Ser Asp Lys Pro Val Ala His
385                 390                 395                 400

```
Val Val Ala Asn Pro Gln Ala Glu Gly Gln Leu Gln Trp Leu Asn Arg
            405                 410                 415

Arg Ala Asn Ala Leu Leu Ala Asn Gly Val Glu Leu Arg Asp Asn Gln
        420                 425                 430

Leu Val Val Pro Ser Glu Gly Leu Tyr Leu Ile Tyr Ser Gln Val Leu
        435                 440                 445

Phe Lys Gly Gln Gly Cys Pro Ser Thr His Val Leu Leu Thr His Thr
    450                 455                 460

Ile Ser Arg Ile Ala Val Ser Tyr Gln Thr Lys Val Asn Leu Leu Ser
465                 470                 475                 480

Ala Ile Lys Ser Pro Cys Gln Arg Glu Thr Pro Glu Gly Ala Glu Ala
                485                 490                 495

Lys Pro Trp Tyr Glu Pro Ile Tyr Leu Gly Gly Val Phe Gln Leu Glu
                500                 505                 510

Lys Gly Asp Arg Leu Ser Ala Glu Ile Asn Arg Pro Asp Tyr Leu Asn
            515                 520                 525

Phe Arg Glu Ser Gly Gln Val Tyr Phe Gly Ile Ile Ala Leu
    530                 535                 540

<210> SEQ ID NO 89
<211> LENGTH: 535
<212> TYPE: PRT
<213> ORGANISM: Artificial Sequence
<220> FEATURE:
<223> OTHER INFORMATION: GCN4-sc-TNFR2

<400> SEQUENCE: 89

Arg Leu Lys Gln Ile Glu Asp Lys Leu Glu Glu Ile Leu Ser Lys Leu
1               5                   10                  15

Tyr His Ile Glu Asn Glu Leu Ala Arg Ile Lys Lys Leu Leu Gly Glu
            20                  25                  30

Arg Gly Ala Pro Gly Gly Gly Ser Gly Gly Gly Ser Gly Gly Gly Ser
        35                  40                  45

Gly Gly Gly Ser Gly Gly Gly Ser Gly Gly Ser Glu Phe Leu Ala Ser
    50                  55                  60

Ser Arg Thr Pro Ser Asp Lys Pro Val Ala His Val Val Ala Asn Pro
65                  70                  75                  80

Gln Ala Glu Gly Gln Leu Gln Trp Leu Asn Arg Arg Ala Asn Ala Leu
                85                  90                  95

Leu Ala Asn Gly Val Glu Leu Arg Asp Asn Gln Leu Val Val Pro Ser
            100                 105                 110

Glu Gly Leu Tyr Leu Ile Tyr Ser Gln Val Leu Phe Lys Gly Gln Gly
        115                 120                 125

Cys Pro Ser Thr His Val Leu Leu Thr His Thr Ile Ser Arg Ile Ala
    130                 135                 140

Val Ser Tyr Gln Thr Lys Val Asn Leu Leu Ser Ala Ile Lys Ser Pro
145                 150                 155                 160

Cys Gln Arg Glu Thr Pro Glu Gly Ala Glu Ala Lys Pro Trp Tyr Glu
                165                 170                 175

Pro Ile Tyr Leu Gly Gly Val Phe Gln Leu Glu Lys Gly Asp Arg Leu
            180                 185                 190

Ser Ala Glu Ile Asn Arg Pro Asp Tyr Leu Asn Phe Arg Glu Ser Gly
        195                 200                 205

Gln Val Tyr Phe Gly Ile Ile Ala Leu Gly Gly Gly Gly Ser Ser Ser
    210                 215                 220
```

```
Arg Thr Pro Ser Asp Lys Pro Val Ala His Val Ala Asn Pro Gln
225                 230                 235                 240

Ala Glu Gly Gln Leu Gln Trp Leu Asn Arg Arg Ala Asn Ala Leu Leu
            245                 250                 255

Ala Asn Gly Val Glu Leu Arg Asp Asn Gln Leu Val Val Pro Ser Glu
                260                 265                 270

Gly Leu Tyr Leu Ile Tyr Ser Gln Val Leu Phe Lys Gly Gln Gly Cys
            275                 280                 285

Pro Ser Thr His Val Leu Leu Thr His Thr Ile Ser Arg Ile Ala Val
        290                 295                 300

Ser Tyr Gln Thr Lys Val Asn Leu Leu Ser Ala Ile Lys Ser Pro Cys
305                 310                 315                 320

Gln Arg Glu Thr Pro Glu Gly Ala Glu Ala Lys Pro Trp Tyr Glu Pro
                325                 330                 335

Ile Tyr Leu Gly Gly Val Phe Gln Leu Glu Lys Gly Asp Arg Leu Ser
            340                 345                 350

Ala Glu Ile Asn Arg Pro Asp Tyr Leu Asn Phe Arg Glu Ser Gly Gln
        355                 360                 365

Val Tyr Phe Gly Ile Ile Ala Leu Gly Gly Gly Ser Ser Ser Arg
    370                 375                 380

Thr Pro Ser Asp Lys Pro Val Ala His Val Ala Asn Pro Gln Ala
385                 390                 395                 400

Glu Gly Gln Leu Gln Trp Leu Asn Arg Arg Ala Asn Ala Leu Leu Ala
                405                 410                 415

Asn Gly Val Glu Leu Arg Asp Asn Gln Leu Val Val Pro Ser Glu Gly
            420                 425                 430

Leu Tyr Leu Ile Tyr Ser Gln Val Leu Phe Lys Gly Gln Gly Cys Pro
        435                 440                 445

Ser Thr His Val Leu Leu Thr His Thr Ile Ser Arg Ile Ala Val Ser
    450                 455                 460

Tyr Gln Thr Lys Val Asn Leu Leu Ser Ala Ile Lys Ser Pro Cys Gln
465                 470                 475                 480

Arg Glu Thr Pro Glu Gly Ala Glu Ala Lys Pro Trp Tyr Glu Pro Ile
                485                 490                 495

Tyr Leu Gly Gly Val Phe Gln Leu Glu Lys Gly Asp Arg Leu Ser Ala
            500                 505                 510

Glu Ile Asn Arg Pro Asp Tyr Leu Asn Phe Arg Glu Ser Gly Gln Val
        515                 520                 525

Tyr Phe Gly Ile Ile Ala Leu
    530                 535
```

<210> SEQ ID NO 90
<211> LENGTH: 547
<212> TYPE: PRT
<213> ORGANISM: Artificial Sequence
<220> FEATURE:
<223> OTHER INFORMATION: VASP-scTNFR2

<400> SEQUENCE: 90

```
Pro Ser Ser Ser Asp Tyr Ser Asp Leu Gln Arg Val Lys Gln Glu Leu
1               5                   10                  15

Leu Glu Glu Val Lys Lys Glu Leu Gln Lys Val Lys Glu Glu Ile Ile
            20                  25                  30

Glu Ala Phe Val Gln Glu Leu Arg Lys Arg Gly Ser Pro Gly Ala Pro
        35                  40                  45
```

```
Gly Gly Gly Ser Gly Gly Ser Gly Gly Ser Gly Gly Gly Ser
    50              55              60
Gly Gly Gly Ser Gly Gly Ser Glu Phe Leu Ala Ser Ser Arg Thr Pro
65              70              75              80
Ser Asp Lys Pro Val Ala His Val Val Ala Asn Pro Gln Ala Glu Gly
                85              90              95
Gln Leu Gln Trp Leu Asn Arg Arg Ala Asn Ala Leu Leu Ala Asn Gly
            100             105             110
Val Glu Leu Arg Asp Asn Gln Leu Val Val Pro Ser Glu Gly Leu Tyr
        115             120             125
Leu Ile Tyr Ser Gln Val Leu Phe Lys Gly Gln Gly Cys Pro Ser Thr
    130             135             140
His Val Leu Leu Thr His Thr Ile Ser Arg Ile Ala Val Ser Tyr Gln
145             150             155             160
Thr Lys Val Asn Leu Leu Ser Ala Ile Lys Ser Pro Cys Gln Arg Glu
                165             170             175
Thr Pro Glu Gly Ala Glu Ala Lys Pro Trp Tyr Glu Pro Ile Tyr Leu
            180             185             190
Gly Gly Val Phe Gln Leu Glu Lys Gly Asp Arg Leu Ser Ala Glu Ile
        195             200             205
Asn Arg Pro Asp Tyr Leu Asn Phe Arg Glu Ser Gly Gln Val Tyr Phe
    210             215             220
Gly Ile Ile Ala Leu Gly Gly Gly Ser Ser Ser Arg Thr Pro Ser
225             230             235             240
Asp Lys Pro Val Ala His Val Val Ala Asn Pro Gln Ala Glu Gly Gln
                245             250             255
Leu Gln Trp Leu Asn Arg Arg Ala Asn Ala Leu Leu Ala Asn Gly Val
            260             265             270
Glu Leu Arg Asp Asn Gln Leu Val Val Pro Ser Glu Gly Leu Tyr Leu
        275             280             285
Ile Tyr Ser Gln Val Leu Phe Lys Gly Gln Gly Cys Pro Ser Thr His
    290             295             300
Val Leu Leu Thr His Thr Ile Ser Arg Ile Ala Val Ser Tyr Gln Thr
305             310             315             320
Lys Val Asn Leu Leu Ser Ala Ile Lys Ser Pro Cys Gln Arg Glu Thr
                325             330             335
Pro Glu Gly Ala Glu Ala Lys Pro Trp Tyr Glu Pro Ile Tyr Leu Gly
            340             345             350
Gly Val Phe Gln Leu Glu Lys Gly Asp Arg Leu Ser Ala Glu Ile Asn
        355             360             365
Arg Pro Asp Tyr Leu Asn Phe Arg Glu Ser Gly Gln Val Tyr Phe Gly
    370             375             380
Ile Ile Ala Leu Gly Gly Gly Ser Ser Ser Arg Thr Pro Ser Asp
385             390             395             400
Lys Pro Val Ala His Val Val Ala Asn Pro Gln Ala Glu Gly Gln Leu
                405             410             415
Gln Trp Leu Asn Arg Arg Ala Asn Ala Leu Leu Ala Asn Gly Val Glu
            420             425             430
Leu Arg Asp Asn Gln Leu Val Val Pro Ser Glu Gly Leu Tyr Leu Ile
        435             440             445
Tyr Ser Gln Val Leu Phe Lys Gly Gln Gly Cys Pro Ser Thr His Val
    450             455             460
```

```
Leu Leu Thr His Thr Ile Ser Arg Ile Ala Val Ser Tyr Gln Thr Lys
465                 470                 475                 480

Val Asn Leu Leu Ser Ala Ile Lys Ser Pro Cys Gln Arg Glu Thr Pro
                485                 490                 495

Glu Gly Ala Glu Ala Lys Pro Trp Tyr Glu Pro Ile Tyr Leu Gly Gly
            500                 505                 510

Val Phe Gln Leu Glu Lys Gly Asp Arg Leu Ser Ala Glu Ile Asn Arg
        515                 520                 525

Pro Asp Tyr Leu Asn Phe Arg Glu Ser Gly Gln Val Tyr Phe Gly Ile
    530                 535                 540

Ile Ala Leu
545

<210> SEQ ID NO 91
<211> LENGTH: 525
<212> TYPE: PRT
<213> ORGANISM: Artificial Sequence
<220> FEATURE:
<223> OTHER INFORMATION: p53-sc-mTNFR2

<400> SEQUENCE: 91

Lys Lys Pro Leu Asp Gly Glu Tyr Phe Thr Leu Gln Ile Arg Gly Arg
1               5                   10                  15

Glu Arg Phe Glu Met Phe Arg Glu Leu Asn Glu Ala Leu Glu Leu Lys
            20                  25                  30

Asp Ala Gln Ala Gly Lys Glu Pro Gly Ala Pro Gly Gly Gly Ser Gly
        35                  40                  45

Gly Gly Ser Gly Gly Gly Ser Gly Gly Gly Ser Gly Gly Gly Ser Gly
    50                  55                  60

Gly Ser Gly Ile Arg Ser Asp Lys Pro Val Ala His Val Val Ala Asn
65                  70                  75                  80

His Gln Val Glu Glu Gln Leu Glu Trp Leu Ser Gln Arg Ala Asn Ala
            85                  90                  95

Leu Leu Ala Asn Gly Met Asp Leu Lys Asp Asn Gln Leu Val Val Pro
        100                 105                 110

Ala Asp Gly Leu Tyr Leu Val Tyr Ser Gln Val Leu Phe Lys Gly Gln
    115                 120                 125

Gly Cys Pro Asp Tyr Val Leu Leu Thr His Thr Val Ser Arg Phe Ala
130                 135                 140

Ile Ser Tyr Gln Glu Lys Val Asn Leu Leu Ser Ala Val Lys Ser Pro
145                 150                 155                 160

Cys Pro Lys Asp Thr Pro Glu Gly Ala Glu Leu Lys Pro Trp Tyr Glu
                165                 170                 175

Pro Ile Tyr Leu Gly Gly Val Phe Gln Leu Glu Lys Gly Asp Gln Leu
            180                 185                 190

Ser Ala Glu Val Asn Leu Pro Lys Tyr Leu Asn Phe Arg Glu Ser Gly
        195                 200                 205

Gln Val Tyr Phe Gly Val Ile Ala Leu Gly Gly Gly Ser Ser Ser
    210                 215                 220

Asp Lys Pro Val Ala His Val Val Ala Asn His Gln Val Glu Glu Gln
225                 230                 235                 240

Leu Glu Trp Leu Ser Gln Arg Ala Asn Ala Leu Leu Ala Asn Gly Met
            245                 250                 255

Asp Leu Lys Asp Asn Gln Leu Val Val Pro Ala Asp Gly Leu Tyr Leu
        260                 265                 270
```

Val Tyr Ser Gln Val Leu Phe Lys Gly Gln Gly Cys Pro Asp Tyr Val
            275                 280                 285

Leu Leu Thr His Thr Val Ser Arg Phe Ala Ile Ser Tyr Gln Glu Lys
        290                 295                 300

Val Asn Leu Leu Ser Ala Val Lys Ser Pro Cys Pro Lys Asp Thr Pro
305                 310                 315                 320

Glu Gly Ala Glu Leu Lys Pro Trp Tyr Glu Pro Ile Tyr Leu Gly Gly
                325                 330                 335

Val Phe Gln Leu Glu Lys Gly Asp Gln Leu Ser Ala Glu Val Asn Leu
            340                 345                 350

Pro Lys Tyr Leu Asn Phe Arg Glu Ser Gly Gln Val Tyr Phe Gly Val
        355                 360                 365

Ile Ala Leu Gly Gly Gly Ser Ser Asp Lys Pro Val Ala His
        370                 375                 380

Val Val Ala Asn His Gln Val Glu Glu Gln Leu Glu Trp Leu Ser Gln
385                 390                 395                 400

Arg Ala Asn Ala Leu Leu Ala Asn Gly Met Asp Leu Lys Asp Asn Gln
                405                 410                 415

Leu Val Val Pro Ala Asp Gly Leu Tyr Leu Val Tyr Ser Gln Val Leu
            420                 425                 430

Phe Lys Gly Gln Gly Cys Pro Asp Tyr Val Leu Leu Thr His Thr Val
        435                 440                 445

Ser Arg Phe Ala Ile Ser Tyr Gln Glu Lys Val Asn Leu Leu Ser Ala
    450                 455                 460

Val Lys Ser Pro Cys Pro Lys Asp Thr Pro Glu Gly Ala Glu Leu Lys
465                 470                 475                 480

Pro Trp Tyr Glu Pro Ile Tyr Leu Gly Gly Val Phe Gln Leu Glu Lys
                485                 490                 495

Gly Asp Gln Leu Ser Ala Glu Val Asn Leu Pro Lys Tyr Leu Asn Phe
            500                 505                 510

Arg Glu Ser Gly Gln Val Tyr Phe Gly Val Ile Ala Leu
        515                 520                 525

<210> SEQ ID NO 92
<211> LENGTH: 518
<212> TYPE: PRT
<213> ORGANISM: Artificial Sequence
<220> FEATURE:
<223> OTHER INFORMATION: GCN4-sc-mTNFR2

<400> SEQUENCE: 92

Arg Leu Lys Gln Ile Glu Asp Lys Leu Glu Ile Leu Ser Lys Leu
1               5                   10                  15

Tyr His Ile Glu Asn Glu Leu Ala Arg Ile Lys Lys Leu Leu Gly Glu
            20                  25                  30

Arg Gly Ala Pro Gly Gly Gly Ser Gly Gly Gly Ser Gly Gly Gly Ser
        35                  40                  45

Gly Gly Gly Ser Gly Gly Gly Ser Gly Gly Ser Gly Ile Arg Ser Asp
    50                  55                  60

Lys Pro Val Ala His Val Val Ala Asn His Gln Val Glu Glu Gln Leu
65                  70                  75                  80

Glu Trp Leu Ser Gln Arg Ala Asn Ala Leu Leu Ala Asn Gly Met Asp
                85                  90                  95

Leu Lys Asp Asn Gln Leu Val Val Pro Ala Asp Gly Leu Tyr Leu Val
            100                 105                 110

```
Tyr Ser Gln Val Leu Phe Lys Gly Gln Gly Cys Pro Asp Tyr Val Leu
            115                 120                 125
Leu Thr His Thr Val Ser Arg Phe Ala Ile Ser Tyr Gln Glu Lys Val
        130                 135                 140
Asn Leu Leu Ser Ala Val Lys Ser Pro Cys Pro Lys Asp Thr Pro Glu
145                 150                 155                 160
Gly Ala Glu Leu Lys Pro Trp Tyr Glu Pro Ile Tyr Leu Gly Gly Val
                165                 170                 175
Phe Gln Leu Glu Lys Gly Asp Gln Leu Ser Ala Glu Val Asn Leu Pro
            180                 185                 190
Lys Tyr Leu Asn Phe Arg Glu Ser Gly Gln Val Tyr Phe Gly Val Ile
        195                 200                 205
Ala Leu Gly Gly Gly Ser Ser Ser Asp Lys Pro Val Ala His Val
    210                 215                 220
Val Ala Asn His Gln Val Glu Glu Gln Leu Glu Trp Leu Ser Gln Arg
225                 230                 235                 240
Ala Asn Ala Leu Leu Ala Asn Gly Met Asp Leu Lys Asp Asn Gln Leu
                245                 250                 255
Val Val Pro Ala Asp Gly Leu Tyr Leu Val Tyr Ser Gln Val Leu Phe
            260                 265                 270
Lys Gly Gln Gly Cys Pro Asp Tyr Val Leu Leu Thr His Thr Val Ser
        275                 280                 285
Arg Phe Ala Ile Ser Tyr Gln Glu Lys Val Asn Leu Leu Ser Ala Val
    290                 295                 300
Lys Ser Pro Cys Pro Lys Asp Thr Pro Glu Gly Ala Glu Leu Lys Pro
305                 310                 315                 320
Trp Tyr Glu Pro Ile Tyr Leu Gly Gly Val Phe Gln Leu Glu Lys Gly
                325                 330                 335
Asp Gln Leu Ser Ala Glu Val Asn Leu Pro Lys Tyr Leu Asn Phe Arg
            340                 345                 350
Glu Ser Gly Gln Val Tyr Phe Gly Val Ile Ala Leu Gly Gly Gly
        355                 360                 365
Ser Ser Ser Asp Lys Pro Val Ala His Val Val Ala Asn His Gln Val
    370                 375                 380
Glu Glu Gln Leu Glu Trp Leu Ser Gln Arg Ala Asn Ala Leu Leu Ala
385                 390                 395                 400
Asn Gly Met Asp Leu Lys Asp Asn Gln Leu Val Val Pro Ala Asp Gly
                405                 410                 415
Leu Tyr Leu Val Tyr Ser Gln Val Leu Phe Lys Gly Gln Gly Cys Pro
            420                 425                 430
Asp Tyr Val Leu Leu Thr His Thr Val Ser Arg Phe Ala Ile Ser Tyr
        435                 440                 445
Gln Glu Lys Val Asn Leu Leu Ser Ala Val Lys Ser Pro Cys Pro Lys
    450                 455                 460
Asp Thr Pro Glu Gly Ala Glu Leu Lys Pro Trp Tyr Glu Pro Ile Tyr
465                 470                 475                 480
Leu Gly Gly Val Phe Gln Leu Glu Lys Gly Asp Gln Leu Ser Ala Glu
                485                 490                 495
Val Asn Leu Pro Lys Tyr Leu Asn Phe Arg Glu Ser Gly Gln Val Tyr
            500                 505                 510
Phe Gly Val Ile Ala Leu
            515
```

```
<210> SEQ ID NO 93
<211> LENGTH: 456
<212> TYPE: PRT
<213> ORGANISM: Artificial Sequence
<220> FEATURE:
<223> OTHER INFORMATION: sc-mTNFR2

<400> SEQUENCE: 93

Ser Asp Lys Pro Val Ala His Val Val Ala Asn His Gln Val Glu Glu
1               5                   10                  15

Gln Leu Glu Trp Leu Ser Gln Arg Ala Asn Ala Leu Leu Ala Asn Gly
            20                  25                  30

Met Asp Leu Lys Asp Asn Gln Leu Val Val Pro Ala Asp Gly Leu Tyr
        35                  40                  45

Leu Val Tyr Ser Gln Val Leu Phe Lys Gly Gln Gly Cys Pro Asp Tyr
    50                  55                  60

Val Leu Leu Thr His Thr Val Ser Arg Phe Ala Ile Ser Tyr Gln Glu
65                  70                  75                  80

Lys Val Asn Leu Leu Ser Ala Val Lys Ser Pro Cys Pro Lys Asp Thr
                85                  90                  95

Pro Glu Gly Ala Glu Leu Lys Pro Trp Tyr Glu Pro Ile Tyr Leu Gly
            100                 105                 110

Gly Val Phe Gln Leu Glu Lys Gly Asp Gln Leu Ser Ala Glu Val Asn
        115                 120                 125

Leu Pro Lys Tyr Leu Asn Phe Arg Glu Ser Gly Gln Val Tyr Phe Gly
    130                 135                 140

Val Ile Ala Leu Gly Gly Gly Ser Ser Asp Lys Pro Val Ala
145                 150                 155                 160

His Val Val Ala Asn His Gln Val Glu Glu Gln Leu Glu Trp Leu Ser
                165                 170                 175

Gln Arg Ala Asn Ala Leu Leu Ala Asn Gly Met Asp Leu Lys Asp Asn
            180                 185                 190

Gln Leu Val Val Pro Ala Asp Gly Leu Tyr Leu Val Tyr Ser Gln Val
        195                 200                 205

Leu Phe Lys Gly Gln Gly Cys Pro Asp Tyr Val Leu Leu Thr His Thr
    210                 215                 220

Val Ser Arg Phe Ala Ile Ser Tyr Gln Glu Lys Val Asn Leu Leu Ser
225                 230                 235                 240

Ala Val Lys Ser Pro Cys Pro Lys Asp Thr Pro Glu Gly Ala Glu Leu
                245                 250                 255

Lys Pro Trp Tyr Glu Pro Ile Tyr Leu Gly Gly Val Phe Gln Leu Glu
            260                 265                 270

Lys Gly Asp Gln Leu Ser Ala Glu Val Asn Leu Pro Lys Tyr Leu Asn
        275                 280                 285

Phe Arg Glu Ser Gly Gln Val Tyr Phe Gly Val Ile Ala Leu Gly Gly
    290                 295                 300

Gly Gly Ser Ser Asp Lys Pro Val Ala His Val Val Ala Asn His
305                 310                 315                 320

Gln Val Glu Glu Gln Leu Glu Trp Leu Ser Gln Arg Ala Asn Ala Leu
                325                 330                 335

Leu Ala Asn Gly Met Asp Leu Lys Asp Asn Gln Leu Val Val Pro Ala
            340                 345                 350

Asp Gly Leu Tyr Leu Val Tyr Ser Gln Val Leu Phe Lys Gly Gln Gly
        355                 360                 365

Cys Pro Asp Tyr Val Leu Leu Thr His Thr Val Ser Arg Phe Ala Ile
```

```
                370                 375                 380
Ser Tyr Gln Glu Lys Val Asn Leu Leu Ser Ala Val Lys Ser Pro Cys
385                 390                 395                 400

Pro Lys Asp Thr Pro Glu Gly Ala Glu Leu Lys Pro Trp Tyr Glu Pro
                405                 410                 415

Ile Tyr Leu Gly Gly Val Phe Gln Leu Glu Lys Gly Asp Gln Leu Ser
                420                 425                 430

Ala Glu Val Asn Leu Pro Lys Tyr Leu Asn Phe Arg Glu Ser Gly Gln
                435                 440                 445

Val Tyr Phe Gly Val Ile Ala Leu
                450                 455

<210> SEQ ID NO 94
<211> LENGTH: 106
<212> TYPE: PRT
<213> ORGANISM: Homo sapiens

<400> SEQUENCE: 94

Asp Phe Thr Pro Pro Thr Val Lys Ile Leu Gln Ser Ser Cys Asp Gly
1               5                   10                  15

Gly Gly His Phe Pro Pro Thr Ile Gln Leu Leu Cys Leu Val Ser Gly
                20                  25                  30

Tyr Thr Pro Gly Thr Ile Asn Ile Thr Trp Leu Glu Asp Gly Gln Val
            35                  40                  45

Met Asp Val Asp Leu Ser Thr Ala Ser Thr Thr Gln Glu Gly Glu Leu
        50                  55                  60

Ala Ser Thr Gln Ser Glu Leu Thr Leu Ser Gln Lys His Trp Leu Ser
65                  70                  75                  80

Asp Arg Thr Tyr Thr Cys Gln Val Thr Tyr Gln Gly His Thr Phe Glu
                85                  90                  95

Asp Ser Thr Lys Lys Cys Ala Asp Ser Asn
                100                 105

<210> SEQ ID NO 95
<211> LENGTH: 27
<212> TYPE: PRT
<213> ORGANISM: Artificial Sequence
<220> FEATURE:
<223> OTHER INFORMATION: Peptide linker

<400> SEQUENCE: 95

Gly Gly Gly Ser Gly Gly Gly Ser Gly Gly Gly Ser Gly Gly Gly Ser
1               5                   10                  15

Gly Gly Gly Ser Gly Gly Ser Glu Phe Leu Ala
                20                  25

<210> SEQ ID NO 96
<211> LENGTH: 26
<212> TYPE: PRT
<213> ORGANISM: Artificial Sequence
<220> FEATURE:
<223> OTHER INFORMATION: Peptide linker

<400> SEQUENCE: 96

Gly Gly Gly Ser Gly Gly Gly Ser Gly Gly Gly Ser Gly Gly Gly Ser
1               5                   10                  15

Gly Gly Gly Ser Gly Gly Ser Gly Ile Arg
                20                  25
```

<210> SEQ ID NO 97
<211> LENGTH: 605
<212> TYPE: PRT
<213> ORGANISM: Artificial Sequence
<220> FEATURE:
<223> OTHER INFORMATION: EHD2-scTNFR2

<400> SEQUENCE: 97

```
Asp Phe Thr Pro Pro Thr Val Lys Ile Leu Gln Ser Ser Cys Asp Gly
1               5                   10                  15

Gly Gly His Phe Pro Pro Thr Ile Gln Leu Leu Cys Leu Val Ser Gly
            20                  25                  30

Tyr Thr Pro Gly Thr Ile Asn Ile Thr Trp Leu Glu Asp Gly Gln Val
        35                  40                  45

Met Asp Val Asp Leu Ser Thr Ala Ser Thr Thr Gln Glu Gly Glu Leu
50                  55                  60

Ala Ser Thr Gln Ser Glu Leu Thr Leu Ser Gln Lys His Trp Leu Ser
65                  70                  75                  80

Asp Arg Thr Tyr Thr Cys Gln Val Thr Tyr Gln Gly His Thr Phe Glu
                85                  90                  95

Asp Ser Thr Lys Lys Cys Ala Asp Ser Asn Gly Gly Gly Ser Gly Gly
            100                 105                 110

Gly Ser Gly Gly Gly Ser Gly Gly Ser Gly Gly Ser Gly Gly
        115                 120                 125

Ser Glu Phe Leu Ala Ser Ser Arg Thr Pro Ser Asp Lys Pro Val Ala
    130                 135                 140

His Val Val Ala Asn Pro Gln Ala Glu Gly Gln Leu Gln Trp Leu Asn
145                 150                 155                 160

Arg Arg Ala Asn Ala Leu Leu Ala Asn Gly Val Glu Leu Arg Asp Asn
                165                 170                 175

Gln Leu Val Val Pro Ser Glu Gly Leu Tyr Leu Ile Tyr Ser Gln Val
            180                 185                 190

Leu Phe Lys Gly Gln Gly Cys Pro Ser Thr His Val Leu Leu Thr His
        195                 200                 205

Thr Ile Ser Arg Ile Ala Val Ser Tyr Gln Thr Lys Val Asn Leu Leu
210                 215                 220

Ser Ala Ile Lys Ser Pro Cys Gln Arg Glu Thr Pro Glu Gly Ala Glu
225                 230                 235                 240

Ala Lys Pro Trp Tyr Glu Pro Ile Tyr Leu Gly Gly Val Phe Gln Leu
                245                 250                 255

Glu Lys Gly Asp Arg Leu Ser Ala Glu Ile Asn Arg Pro Asp Tyr Leu
            260                 265                 270

Asn Phe Arg Glu Ser Gly Gln Val Tyr Phe Gly Ile Ile Ala Leu Gly
        275                 280                 285

Gly Gly Gly Ser Ser Ser Arg Thr Pro Ser Asp Lys Pro Val Ala His
    290                 295                 300

Val Val Ala Asn Pro Gln Ala Glu Gly Gln Leu Gln Trp Leu Asn Arg
305                 310                 315                 320

Arg Ala Asn Ala Leu Leu Ala Asn Gly Val Glu Leu Arg Asp Asn Gln
                325                 330                 335

Leu Val Val Pro Ser Glu Gly Leu Tyr Leu Ile Tyr Ser Gln Val Leu
            340                 345                 350

Phe Lys Gly Gln Gly Cys Pro Ser Thr His Val Leu Leu Thr His Thr
        355                 360                 365

Ile Ser Arg Ile Ala Val Ser Tyr Gln Thr Lys Val Asn Leu Leu Ser
```

```
                370                 375                 380
Ala Ile Lys Ser Pro Cys Gln Arg Glu Thr Pro Glu Gly Ala Glu Ala
385                 390                 395                 400

Lys Pro Trp Tyr Glu Pro Ile Tyr Leu Gly Gly Val Phe Gln Leu Glu
                405                 410                 415

Lys Gly Asp Arg Leu Ser Ala Glu Ile Asn Arg Pro Asp Tyr Leu Asn
                420                 425                 430

Phe Arg Glu Ser Gly Gln Val Tyr Phe Gly Ile Ile Ala Leu Gly Gly
                435                 440                 445

Gly Gly Ser Ser Ser Arg Thr Pro Ser Asp Lys Pro Val Ala His Val
        450                 455                 460

Val Ala Asn Pro Gln Ala Glu Gly Gln Leu Gln Trp Leu Asn Arg Arg
465                 470                 475                 480

Ala Asn Ala Leu Leu Ala Asn Gly Val Glu Leu Arg Asp Asn Gln Leu
                485                 490                 495

Val Val Pro Ser Glu Gly Leu Tyr Leu Ile Tyr Ser Gln Val Leu Phe
                500                 505                 510

Lys Gly Gln Gly Cys Pro Ser Thr His Val Leu Leu Thr His Thr Ile
                515                 520                 525

Ser Arg Ile Ala Val Ser Tyr Gln Thr Lys Val Asn Leu Leu Ser Ala
                530                 535                 540

Ile Lys Ser Pro Cys Gln Arg Glu Thr Pro Glu Gly Ala Glu Ala Lys
545                 550                 555                 560

Pro Trp Tyr Glu Pro Ile Tyr Leu Gly Gly Val Phe Gln Leu Glu Lys
                565                 570                 575

Gly Asp Arg Leu Ser Ala Glu Ile Asn Arg Pro Asp Tyr Leu Asn Phe
                580                 585                 590

Arg Glu Ser Gly Gln Val Tyr Phe Gly Ile Ile Ala Leu
                595                 600                 605

<210> SEQ ID NO 98
<211> LENGTH: 588
<212> TYPE: PRT
<213> ORGANISM: Artificial Sequence
<220> FEATURE:
<223> OTHER INFORMATION: EHD2-sc-mTNFR2

<400> SEQUENCE: 98

Asp Phe Thr Pro Pro Thr Val Lys Ile Leu Gln Ser Ser Cys Asp Gly
1               5                   10                  15

Gly Gly His Phe Pro Pro Thr Ile Gln Leu Leu Cys Leu Val Ser Gly
                20                  25                  30

Tyr Thr Pro Gly Thr Ile Asn Ile Thr Trp Leu Glu Asp Gly Gln Val
            35                  40                  45

Met Asp Val Asp Leu Ser Thr Ala Ser Thr Thr Gln Glu Gly Glu Leu
50                  55                  60

Ala Ser Thr Gln Ser Glu Leu Thr Leu Ser Gln Lys His Trp Leu Ser
65                  70                  75                  80

Asp Arg Thr Tyr Thr Cys Gln Val Thr Tyr Gln Gly His Thr Phe Glu
                85                  90                  95

Asp Ser Thr Lys Lys Cys Ala Asp Ser Asn Gly Gly Ser Gly Gly
                100                 105                 110

Gly Ser Gly Gly Gly Ser Gly Gly Ser Gly Gly Gly Ser Gly Gly
            115                 120                 125

Ser Gly Ile Arg Ser Asp Lys Pro Val Ala His Val Val Ala Asn His
```

```
              130                 135                 140
Gln Val Glu Glu Gln Leu Glu Trp Leu Ser Gln Arg Ala Asn Ala Leu
145                 150                 155                 160

Leu Ala Asn Gly Met Asp Leu Lys Asp Asn Gln Leu Val Val Pro Ala
                165                 170                 175

Asp Gly Leu Tyr Leu Val Tyr Ser Gln Val Leu Phe Lys Gly Gln Gly
            180                 185                 190

Cys Pro Asp Tyr Val Leu Leu Thr His Thr Val Ser Arg Phe Ala Ile
                195                 200                 205

Ser Tyr Gln Glu Lys Val Asn Leu Leu Ser Ala Val Lys Ser Pro Cys
        210                 215                 220

Pro Lys Asp Thr Pro Glu Gly Ala Glu Leu Lys Pro Trp Tyr Glu Pro
225                 230                 235                 240

Ile Tyr Leu Gly Gly Val Phe Gln Leu Glu Lys Gly Asp Gln Leu Ser
                245                 250                 255

Ala Glu Val Asn Leu Pro Lys Tyr Leu Asn Phe Arg Glu Ser Gly Gln
                260                 265                 270

Val Tyr Phe Gly Val Ile Ala Leu Gly Gly Gly Ser Ser Ser Asp
        275                 280                 285

Lys Pro Val Ala His Val Val Ala Asn His Gln Val Glu Glu Gln Leu
        290                 295                 300

Glu Trp Leu Ser Gln Arg Ala Asn Ala Leu Leu Ala Asn Gly Met Asp
305                 310                 315                 320

Leu Lys Asp Asn Gln Leu Val Val Pro Ala Asp Gly Leu Tyr Leu Val
                325                 330                 335

Tyr Ser Gln Val Leu Phe Lys Gly Gln Gly Cys Pro Asp Tyr Val Leu
                340                 345                 350

Leu Thr His Thr Val Ser Arg Phe Ala Ile Ser Tyr Gln Glu Lys Val
            355                 360                 365

Asn Leu Leu Ser Ala Val Lys Ser Pro Cys Pro Lys Asp Thr Pro Glu
        370                 375                 380

Gly Ala Glu Leu Lys Pro Trp Tyr Glu Pro Ile Tyr Leu Gly Gly Val
385                 390                 395                 400

Phe Gln Leu Glu Lys Gly Asp Gln Leu Ser Ala Glu Val Asn Leu Pro
                405                 410                 415

Lys Tyr Leu Asn Phe Arg Glu Ser Gly Gln Val Tyr Phe Gly Val Ile
                420                 425                 430

Ala Leu Gly Gly Gly Ser Ser Ser Asp Lys Pro Val Ala His Val
            435                 440                 445

Val Ala Asn His Gln Val Glu Glu Gln Leu Glu Trp Leu Ser Gln Arg
        450                 455                 460

Ala Asn Ala Leu Leu Ala Asn Gly Met Asp Leu Lys Asp Asn Gln Leu
465                 470                 475                 480

Val Val Pro Ala Asp Gly Leu Tyr Leu Val Tyr Ser Gln Val Leu Phe
                485                 490                 495

Lys Gly Gln Gly Cys Pro Asp Tyr Val Leu Leu Thr His Thr Val Ser
            500                 505                 510

Arg Phe Ala Ile Ser Tyr Gln Glu Lys Val Asn Leu Leu Ser Ala Val
        515                 520                 525

Lys Ser Pro Cys Pro Lys Asp Thr Pro Glu Gly Ala Glu Leu Lys Pro
        530                 535                 540

Trp Tyr Glu Pro Ile Tyr Leu Gly Gly Val Phe Gln Leu Glu Lys Gly
545                 550                 555                 560
```

```
Asp Gln Leu Ser Ala Glu Val Asn Leu Pro Lys Tyr Leu Asn Phe Arg
                565                 570                 575
Glu Ser Gly Gln Val Tyr Phe Gly Val Ile Ala Leu
            580                 585

<210> SEQ ID NO 99
<211> LENGTH: 10
<212> TYPE: PRT
<213> ORGANISM: Artificial Sequence
<220> FEATURE:
<223> OTHER INFORMATION: Peptide linker

<400> SEQUENCE: 99

Gly Gly Ser Gly Gly Gly Gly Ser Gly Gly
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Peptide linker

<400> SEQUENCE: 100

Gly Gly Ser Gly Gly Gly Ser Ser Gly Gly
1               5                   10
```